United States Patent
O'Donnell et al.

(10) Patent No.: US 10,378,066 B2
(45) Date of Patent: *Aug. 13, 2019

(54) MOLECULAR DIAGNOSTIC TEST FOR CANCER

(71) Applicant: Almac Diagnostics Limited, Craigavon (GB)

(72) Inventors: Jude O'Donnell, Galbally (GB); Max Bylesjo, Glasgow (GB); Fionnuala Patterson, Greenlsland (GB); Steve Deharo, Hillsborough (GB); Laura A. Hill, Lisburn (GB); Katherine E. Keating, Magherafelt (GB); Timothy Davison, Hillsborough (GB); Vitali Proutski, Hillsborough (GB); Denis Paul Harkin, Dromore (GB); Richard Kennedy, Belfast (GB); Nicolas Goffard, Belfast (GB)

(73) Assignee: Almac Diagnostic Services Limited, Craigavon (GB)

(*) Notice: Subject to any disclaimer, the term of this patent is extended or adjusted under 35 U.S.C. 154(b) by 260 days.

This patent is subject to a terminal disclaimer.

(21) Appl. No.: 15/426,923

(22) Filed: Feb. 7, 2017

(65) Prior Publication Data
US 2017/0198360 A1 Jul. 13, 2017

Related U.S. Application Data

(62) Division of application No. 13/821,404, filed as application No. PCT/US2011/051803 on Sep. 15, 2011, now Pat. No. 9,670,547.

(60) Provisional application No. 61/383,201, filed on Sep. 15, 2010, provisional application No. 61/490,039, filed on May 25, 2011.

(51) Int. Cl.
| | | |
|---|---|---|
| C12Q 1/6886 | (2018.01) | |
| C12Q 1/6876 | (2018.01) | |
| G16B 25/00 | (2019.01) | |
| G16B 40/00 | (2019.01) | |
| G16H 50/30 | (2018.01) | |
| C40B 30/04 | (2006.01) | |
| A61K 33/24 | (2019.01) | |

(52) U.S. Cl.
CPC ............ C12Q 1/6886 (2013.01); A61K 33/24 (2013.01); C12Q 1/6876 (2013.01); G16B 25/00 (2019.02); G16B 40/00 (2019.02); G16H 50/30 (2018.01); C12Q 2600/106 (2013.01); C12Q 2600/112 (2013.01); C12Q 2600/158 (2013.01); C40B 30/04 (2013.01)

(58) Field of Classification Search
None
See application file for complete search history.

(56) References Cited

U.S. PATENT DOCUMENTS

| | | |
|---|---|---|
| 5,143,854 A | 9/1992 | Pirrung et al. |
| 5,288,644 A | 2/1994 | Beavis et al. |
| 5,324,633 A | 6/1994 | Fodor et al. |
| 5,432,049 A | 7/1995 | Fischer et al. |
| 5,470,710 A | 11/1995 | Weiss et al. |
| 5,492,806 A | 2/1996 | Drmanac et al. |
| 5,503,980 A | 4/1996 | Cantor |
| 5,510,270 A | 4/1996 | Fodor et al. |
| 5,525,464 A | 6/1996 | Drmanac et al. |
| 5,547,839 A | 8/1996 | Dower et al. |
| 5,580,732 A | 12/1996 | Grossman et al. |
| 5,661,028 A | 8/1997 | Foote |
| 5,800,992 A | 9/1998 | Fodor et al. |
| 6,228,575 B1 | 5/2001 | Gingeras et al. |
| 6,308,170 B1 | 10/2001 | Balaban |
| 7,695,913 B2 | 4/2010 | Cowens et al. |
| 2003/0073083 A1 | 4/2003 | Tamayo et al. |
| 2004/0146921 A1 | 7/2004 | Eveleigh et al. |
| 2006/0142231 A1 | 6/2006 | Ashworth et al. |
| 2007/0218512 A1 | 9/2007 | Strongin et al. |
| 2009/0023149 A1 | 1/2009 | Knudsen |

(Continued)

FOREIGN PATENT DOCUMENTS

| | | |
|---|---|---|
| CN | 1839205 A1 | 9/2006 |
| CN | 1922490 A | 2/2007 |

(Continued)

OTHER PUBLICATIONS

Korean Office Action for co-pending Korean Patent Application No. 10-2013-7009145, dated Nov. 29, 2017, 21 pages, English translation included.

(Continued)

*Primary Examiner* — Kaijiang Zhang
(74) *Attorney, Agent, or Firm* — Finnegan, Henderson, Farabow, Garrett & Dunner, LLP

(57) ABSTRACT

Methods and compositions are provided for the identification of a molecular diagnostic test for cancer. The test defines a novel DNA damage repair deficient molecular subtype and enables classification of a patient within this subtype. The present invention can be used to determine whether patients with cancer are clinically responsive or non-responsive to a therapeutic regimen prior to administration of any chemotherapy. This test may be used in different cancer types and with different drugs that directly or indirectly affect DNA damage or repair, such as many of the standard cytotoxic chemotherapeutic drugs currently in use. In particular, the present invention is directed to the use of certain combinations of predictive markers, wherein the expression of the predictive markers correlates with responsiveness or non-responsiveness to a therapeutic regimen.

31 Claims, 13 Drawing Sheets

Specification includes a Sequence Listing.

(56) References Cited

U.S. PATENT DOCUMENTS

| | | |
|---|---|---|
| 2009/0062196 A1 | 3/2009 | D'Andrea et al. |
| 2010/0304989 A1 | 12/2010 | Von Hoff et al. |

FOREIGN PATENT DOCUMENTS

| | | |
|---|---|---|
| EP | 0373203 B2 | 6/1990 |
| EP | 0785280 B1 | 7/1997 |
| WO | WO 95/21265 | 8/1995 |
| WO | WO 96/31622 | 10/1996 |
| WO | WO 97/10365 | 3/1997 |
| WO | WO 97/27317 | 7/1997 |
| WO | WO 2004/106495 A2 | 12/2004 |
| WO | WO 2005/026735 A2 | 3/2005 |
| WO | WO 2005/054508 A2 | 6/2005 |
| WO | WO 2005/083128 A2 | 9/2005 |
| WO | WO 2005/083440 A2 | 9/2005 |
| WO | WO 2006/048291 A2 | 5/2006 |
| WO | WO 2006/093507 A2 | 9/2006 |
| WO | WO 2007/038792 A2 | 4/2007 |
| WO | WO 2007/045996 A1 | 4/2007 |
| WO | WO 2007/084992 A2 | 7/2007 |
| WO | WO 2007/112330 A2 | 10/2007 |
| WO | WO 2008/005281 A2 | 1/2008 |
| WO | WO 2008/089465 A2 | 7/2008 |
| WO | WO 2008/104543 A2 | 9/2008 |
| WO | WO 2008/132176 A2 | 11/2008 |
| WO | WO 2010/006048 A2 | 1/2010 |
| WO | WO 2010/040083 A2 | 4/2010 |
| WO | WO 2010/045463 A2 | 4/2010 |
| WO | WO 2010/060055 A1 | 5/2010 |
| WO | WO 2011/109440 A1 | 9/2011 |
| WO | WO 2011/153545 A2 | 12/2011 |
| WO | WO 2012/037378 A2 | 3/2012 |

OTHER PUBLICATIONS

Lord et al., "Targeted therapy for cancer using PARP inhibitors," Curr Opin Pharmacol, 8(4):363-369, (2008).

Japanese Office Action for co-pending Japanese Patent Application No. 2016-238969, dated Nov. 7, 2017, 9 pages, English translation included.

Vilmar et al., "Customising chemotherapy in advanced nonsmall cell lung cancer: daily practice and perspectives," Eur Respir Rev, 20(119):45-52, (2011).

Wang et al., "Negative feedback regulation of IFN-gamma pathway by IFN regulatory factor 2 in esophageal cancers," Cancer Res, 68(4):1136-1143, (2008).

Oberthuer et al., "The tumor-associated antigen PRAME is universally expressed in high-stage neuroblastoma and associated with poor outcome," Clin Cancer Res, 10(13):4307-4313, (2004).

Summons to attend oral proceedings pursuant to Rule 115(1) EPC for Application No. 11825959.7-1118 / 2619574, dated Aug. 9, 2018.

American Cancer Society: Cancer Facts and Figures, (2010).

Arun et al., "Visual inspection Versus Quantitative Flow Cytometry to Detect Aberrant C Expression in Malignant T Cells", Cytometry B Clin Cytom, 78(3):169-175, (2010).

Benjamini et al., "Controlling the False Discovery Rate: a Practical and Powerful Approach to Multiple Testing", J R Stat Soc, 57:289:300, (1995).

Bonnefoi et al, "Validation of gene signatures that predict the response of breast cancer to neoadjuvant chemotherapy: a substudy of the EORTC 10994/BIG 00-01 clinical trial", Lancet Oncol, 8:1071-1078, (2007).

Burlingame et al., "Mass Spectrometry", Anal Chem, 70:647 R-716R, (1998).

Cleator et al., "Gene Expression Patterns for Doxorubicin (Adriamycin) and Cyclophosphamide (Cytoxan) (AC) Response and Resistance", Breast Cancer Research and Treatment, 95(3):229-233, (2006).

ClinicalTrials.gov, "AzD2281 and Carboplatin in Treating Patients with BRCA1/BRCA2-Associated or Hereditary Metastic or Unresectable Breast and/or Ovarian Cancer", [online] Mar. 28, 2008 (retrieved Mar. 19, 2012), available on the Internet: <URL: http://clinicaltrials.gov/archive/NCT00647062/2008_03_28>.

Doolan et al., "Prevalence and Prognostic and Predictive Relevance of PRAME in Breast Cancer", Breast Cancer Res Treat, 109(2):359-365, (2008).

Dudoit et al., "Comparison of Discrimination Methods for the Classification of Tumors Using Gene Expression Data", J Am Statist Assoc, 97(457):77-87, (2002).

Farmer et al., "A Stroma-Related Gene Signature Predicts Resistance to Epirubicin-Containing Neoadjuvant Chemotherapy in Breast Cancer", Breast Cancer Research and Treatment, 106(Suppl 1):S11, (2007).

Hess et al., "Pharmacogenomic Predictor of Sensitivity to Preoperative Chemotherapy with Paclitaxel and Fluorouracil, Doxorubicin, and Cyclophosphamide in Breast Cancer", J Clin Oncol, 24(26):4236-4244, (2006).

Hsu et al., "Pharmacogenomic strategies provide a rational approach to the treatment of cisplatin-resistant patients with advanced cancer", J Clin Oncol, 25(28):4350-4357, (2007). Retracted as of Nov. 16, 2010.

Ino et al., "Indoleamine 2,3-dioxygenase is a novel prognostic indicator for endometrial cancer", British Journal of Cancer, vol. 95:1555-1561, (2006).

Iwamoto et al., "Gene Pathways Associated with Prognosis and Chemotherapy Sensitivity in Molecular Subtypes of Breast Cancer", J Natl Cancer Inst, 103:264-272, (2011).

Jackson et al., "The DNA-damage response in human biology and disease", Nature, 461(22):1071-1078, (2009).

Jiang et al., "CXCL10 Expression and Prognostic Significance in Stage II and III Colorectal Cancer", Mol Biol Rep, 37(6):3029-3036, (2010).

Kawano et al., "Oncogene Associated cDNA Microarray Analysis Shows PRAME Gene Expression is a Marker for Response to Anthracycline Containing Chemotherapy in Patients with Diffuse Large B-Cell Lymphoma", Journal of Clinical and Experimental Hematopathology, 49(1):1-7, (2009).

Kennedy et al., "The Fanconi Anemia/BRCA Pathway: New Faces in the Crowd", Genes Dev, 19:2925-2940, (2005).

Kennedy et al., "DNA Repair Pathways in Clinical Practice: Lessons From Pediatric Cancer Susceptibility Syndromes", J Clin Onco, 24(23):3799-3808, (2006).

Kerr et al., "Expression profiling of BRCA1 and BRCA2 deficient human tumors and cell-lines using a breast specific platform to identify a biomarker of DNA repair deficiency", European Journal of Cancer, 7(4):Supplement p. 21, Abstract No. PP128, (2009).

Kim et al., "Analysis of Chromosomal Changes in Serous Ovarian Carcinoma by Microarray Comparative Genomic Hybridization: Potential Predictive Markers for Chemoresistant Disease", Acta Obstetrica et Gynaecologica Japonica, 58(2):794(S-646), P-IS-41, (2006).

Korrat et al., "Gene Signature-Based Prediction of Tumor Response to Cyclophosphamide", Cancer Genomics & Protemics, 4(3), 187-195, (2007).

Lee et al., "Prospective Comparison of Clinical and Genomic Multivariate Predictors of Response to Neoadjuvant Chemotherapy in Breast Cancer", Clin Cancer Res, 16:711-718, (2010).

Liang et al., "DNA Damage Response Pathways in Tumor Suppression and Cancer Treatment", World J Surg, 33:661-666, (2009).

Linn et al., "Clinical relevance of the triple negative breast cancer concept: Genetic basis and clinical utility of the concept", J Eur J Cancer, 45(Suppl 1):11-26, (2009).

Miyoshi et al., "Predictive factors for response to chemotherapy in breast cancers", Japanese Journal of Clinical Medicine, 65(Suppl. 6):154-159, (2007).

Nagasaki et al., "Identification of drug-responsiveness genes towards personalized medicine for breast cancer", Proceedings of the Japanese Cancer Association, 63:486-486, P-13, (2004).

Nguyen et al., "Tumor classification by partial least squares using microarray gene expression data", Bioinformatics, 18:39-50, (2002).

O'Shaughnessy et al., "Iniparib plus Chemotherapy in Metastatic Triple-Negative Breast Cancer", N Engl J Med, 364(3):205-214, (2011).

(56) References Cited

OTHER PUBLICATIONS

Ooyama et al., "Gene Expression Analysis Using Human Cancer Xenografts to Identify Novel Predictive Marker Genes for the Efficacy of 5-Fluorouracil-Based Drugs", Cancer Science, 97(6):510-522, (2006).
Raitman et al., "Characterizing the role of CXCL10 in basal and luminal breast cancer subtypes", 100th annual meeting of the American association for cancer research, 50:806, (2009).
Rodier et al., "Persistent DNA damage signaling triggers senescence-associated inflammatory cytokine secretion", Nat Cell Biol, 11(8):973-979, (2009).
Rodriguez et al., "DNA Repair Signature is Associated with Anthracycline Response in Triple Negative Breast Cancer Patients", Breast Cancer Research and Treatment, 123(1):189-196, (2010).
Schena et al., "Parallel human genome analysis: Microarray-based expression monitoring of 1000 genes", Proc Natl Acad Sci USA, 93:10614-10619, (1996).
Stahle et al., "Partial least squares analysis with cross-validation for the two-class problem: A Monto Carlo study", J Chemom, 1:185-196, (1987).
Tabchy et al., "Evaluation of a 30-Gene Paclitaxel, Fluorouracil, Doxorubicin, and Cyclophosphamide Chemotherapy Response Predictor in a Multicenter Randomized Trial in Breast Cancer", Clin Cancer Res, 16(21):5351-5361, (2010).
Tibshirani et al., "Estimating the number of clusters in a data set via the gap statistic", J R Stat Soc, 63(2):411-423, (2002).
Tibshirani et al., "Diagnosis of multiple cancer types by shrunken centroids of gene expression", Proc Natl Acad Sci USA, 99(10):6567-6572, (2002).
Tsao et al., "Gene Expression Profiles for Predicting the Efficacy of the Anticancer Drug 5-Fluorouracil in Breast Cancer", DNA and Cell Biology, pp. 285-296, (2010).
Vanderwerf et al., "TLR8-dependent TNF-α overexpression in Fanconi anemia group C cells," Blood, 114(26):5290-5298, (2009).
Van't Veer et al., "Gene expression profiling predicts clinical outcome of breast cancer", Nature, 415:530, (2002).
Wold, "Pattern recognition by means of disjoint principal components models", Pattern Recogn, 8:127-139, (1976).
Wray et. al., "The Genetic Interpretation of Area under the ROC Curve in Genomic Profiling", PLoS Genetics, 6(2):e1000864, (2010).
Xu, "DNA damage: a trigger of innate immunity but a requirement for adaptive immune homeostasis", Nat Rev Immuno, 16:261-270, (2006).
Australian First Office Action dated Mar. 21, 2014 in counterpart Australian Patent Application No. 2011302004.
Chinese Office Action and Search Report dated Jan. 14, 2014 in counterpart Chinese Patent Application No. 201180047116.5.
Chinese Second Office Action in counterpart Chinese Patent Application No. 201180047116.5, dated Oct. 14, 2014.
Chinese Notification of the Third Office Action for counterpart Chinese Patent Application No. 201180047116.5, dated Jun. 18, 2015. 23 pages. English excerpt included.
Chinese Notification of the Fourth Office Action for counterpart Chinese Patent Application No. 201180047116.5, dated Feb. 22, 2016. 21 pages. English excerpt included.
Notice of Reasons of Rejection of Japanese Patent Application No. 2013-529331, dated Sep. 15, 2015.
Decision of Rejection of Japanese Patent Application No. 2013-529331, dated Aug. 9, 2016.

Eurasian First Office Action in counterpart Eurasian Patent Application No. 201390370, dated Oct. 27, 2014.
European Supplemental Search Report dated Feb. 7, 2014 in counterpart European Patent Application No. 11825959.7.
Non-Final Office Action in U.S. Appl. No. 14/047,949 dated Mar. 10, 2014.
Final Office Action in U.S. Appl. No. 14/047,949 dated Aug. 20, 2014.
Non-Final Office Action in U.S. Appl. No. 13/821,404, dated Jan. 29, 2015.
Non-Final Office Action in U.S. Appl. No. 14/047,949, dated Nov. 3, 2015.
Final Office Action in U.S. Appl. No. 13/821,404, dated Nov. 3, 2015.
Final Office Action in U.S. Appl. No. 14/047,949, dated Jul. 29, 2016.
International Search Report and Written Opinion for PCT/US2011/051803, dated Apr. 18, 2012.
International Preliminary Report on Patentability for International Application No. PCT/US2011/051803, dated Mar. 19, 2013.
International Search Report for International Application No. PCT/GB2014/052727, dated Dec. 16, 2014. (U.S. Appl. No. 14/917,925).
International Search Report for International Application No. PCT/GB2014/052728, dated Dec. 18, 2014. (U.S. Appl. No. 14/917,913).
Office Action for Israeli Application No. 225076, dated Sep. 24, 2015.
Office Action for Israeli Application No. 225076, dated Dec. 18, 2016.
Substantive Examination Report Stage I for Indonesian Application No. W-00201301459. 4 pages. English excerpt included.
Written Opinion of Singaporean Application No. 2013016175, dated Aug. 7, 2014.
Written Opinion of the International Searching Authority for International Application No. PCT/GB2014/052727, dated Dec. 16, 2014. (U.S. Appl. No. 14/917,925).
Written Opinion of the International Searching Authority for International Application No. PCT/GB2014/052728, dated Dec. 18, 2014. (U.S. Appl. No. 14/917,913).
New Zealand Office Action dated Jul. 29, 2013 in counterpart New Zealand Patent Application No. 608459.
New Zealand Second Office Action dated Feb. 10, 2014 in counterpart New Zealand Patent Application No. 608459.
New Zealand Third Office Action in counterpart New Zealand Patent Application No. 608459, dated Jan. 23, 2015.
New Zealand First Office Action dated Feb. 10, 2014 in counterpart New Zealand Patent Application No. 620799.
Co-pending U.S. Appl. No. 14/917,925.
Co-pending U.S. Appl. No. 14/917,913.
Bouwman et al., "The effects of deregulated DNA damage signalling on cancer chemotherapy response and resistance," Nat Rev Cancer 12(9):587-598, (2012).
Communication pursuant to Article 94(3) EPC for Application No. 16 745 140.0-1111, dated Mar. 29, 2019.
Mulligan et al., "Identification of a novel breast cancer molecular subgroup associated with a deficiency in DNA-damage response," J Clin Oncol 29 (2011) (suppl; abstr 10511).
Mulligan et al., "Identification and validation of an anthracycline/cyclophosphamide-based chemotherapy response assay in breast cancer," Breast Diseases: A Year Book® Quarterly, 25(3):235-237 (2014).

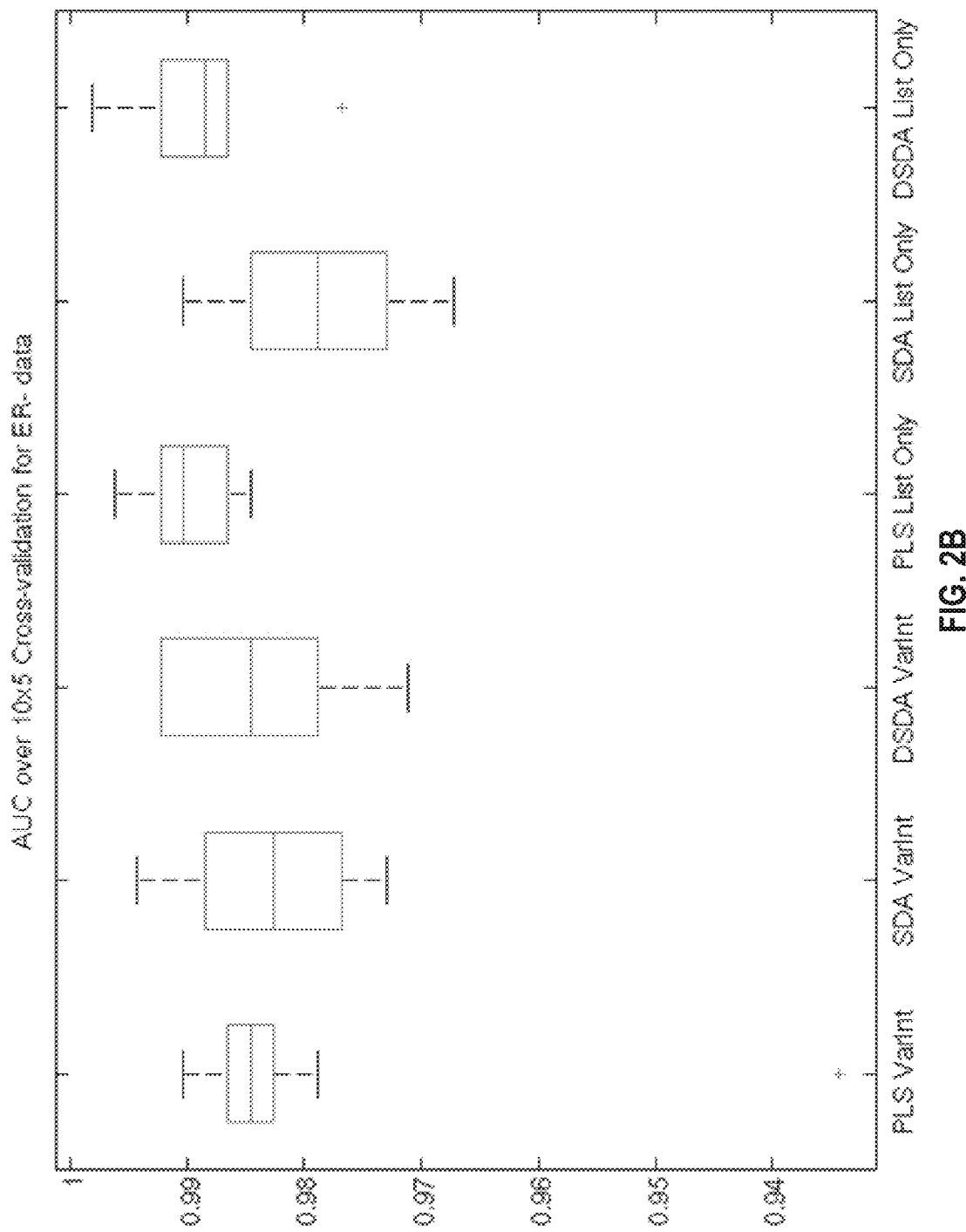

MOLECULAR DIAGNOSTIC TEST FOR CANCER

CROSS-REFERENCE TO RELATED APPLICATIONS

This application is a division of U.S. patent application Ser. No. 13/821,404, which is a 35 U.S.C. § 371 national stage application of International Patent Application No. PCT/US2011/051803, filed on Sep. 15, 2011, which claims the benefit of priority to U.S. Provisional Patent Application No. 61/383,201 filed Sep. 15, 2010 and U.S. Provisional Patent Application No. 61/490,039 filed May 25, 2011, all of which are incorporated herein by reference in their entirety.

FIELD OF THE INVENTION

The present invention relates to a molecular diagnostic test useful for diagnosing cancers from different anatomical sites that includes the use of a common DNA damage repair deficiency subtype. The invention includes the use of a 44-gene classification model that is used to identify this DNA damage repair deficiency molecular subtype. One application is the stratification of response to, and selection of patients for breast cancer therapeutic drug classes, including DNA damage causing agents and DNA repair targeted therapies. Another application is the stratification of ovarian cancer patients into those that respond and those that do not respond to DNA damage causing agents. The present invention provides a test that can guide conventional therapy selection as well as selecting patient groups for enrichment strategies during clinical trial evaluation of novel therapeutics. DNA repair deficient subtypes can be identified from fresh/frozen (FF) or formalin fixed paraffin embedded (FFPE) patient samples.

BACKGROUND

The pharmaceutical industry continuously pursues new drug treatment options that are more effective, more specific or have fewer adverse side effects than currently administered drugs. Drug therapy alternatives are constantly being developed because genetic variability within the human population results in substantial differences in the effectiveness of many drugs. Therefore, although a wide variety of drug therapy options are currently available, more therapies are always needed in the event that a patient fails to respond.

Traditionally, the treatment paradigm used by physicians has been to prescribe a first-line drug therapy that results in the highest success rate possible for treating a disease. Alternative drug therapies are then prescribed if the first is ineffective. This paradigm is clearly not the best treatment method for certain diseases. For example, in diseases such as cancer, the first treatment is often the most important and offers the best opportunity for successful therapy, so there exists a heightened need to chose an initial drug that will be the most effective against that particular patient's disease.

It is anticipated that there will be 207,090 new female breast cancer diagnoses in the US this year and 39,840 female breast cancer related deaths (American Cancer Society: Cancer Facts and Figures 2010). Standard chemotherapy typically includes direct DNA damaging agents such as anthracyclines and alkylating agents as well as antimetabolites and antimicrotubule agents.

Ovarian cancer is the leading cause of death among all gynecological cancers in western countries. This high death rate is due to the diagnosis at an advanced stage in most patients. Epithelial ovarian cancer (EOC) constitutes 90% of ovarian malignancies and is classified into distinct histologic categories including serous, mucinous, endometrioid, clear cell, transitional, mixed, and undifferentiated subtypes. There is increasing evidence that these differed histologies arise from different aetiologies. The current standard treatment for ovarian cancer is debulking surgery and standard platinum taxane based cytotoxic chemotherapy. However, not all patients respond to this, and of those that do, approximately 70% will experience a recurrence. Specific targeted therapies for ovarian cancer based on histological or molecular classification have not yet reached the marketplace. Similarly for other types of cancer, there is still no accurate way of selecting appropriate cytotoxic chemotherapeutic agents.

The advent of microarrays and molecular genomics has the potential for a significant impact on the diagnostic capability and prognostic classification of disease, which may aid in the prediction of the response of an individual patient to a defined therapeutic regimen. Microarrays provide for the analysis of large amounts of genetic information, thereby providing a genetic fingerprint of an individual. There is much enthusiasm that this technology will ultimately provide the necessary tools for custom-made drug treatment regimens.

Currently, healthcare professionals have few mechanisms to help them identify cancer patients who will benefit from chemotherapeutic agents. Identification of the optimal first-line drug has been difficult because methods are not available for accurately predicting which drug treatment would be the most effective for a particular cancer's physiology. This deficiency results in relatively poor single agent response rates and increased cancer morbidity and death. Furthermore, patients often needlessly undergo ineffective, toxic drug therapy.

Molecular markers have been used to select appropriate treatments, for example, in breast cancer. Breast tumors that do not express the estrogen and progesterone hormone receptors as well as the HER2 growth factor receptor, called "triple negative", appear to be responsive to PARP-1 inhibitor therapy (Linn, S. C., and Van't Veer, L., J. Eur J Cancer 45 Suppl 1, 11-26 (2009); O'Shaughnessy, J., et al. N Engl J Med 364, 205-214 (2011). Recent studies indicate that the triple negative status of a breast tumor may indicate responsiveness to combination therapy including PARP-1 inhibitors, but may not be sufficient to indicate responsiveness to individual PARP-1 inhibitors. (O'Shaughnessy et al., 2011).

Furthermore, there have been other studies that have attempted to identify gene classifiers associated with molecular subtypes to indicate responsiveness of chemotherapeutic agents (Farmer et al. Nat Med 15, 68-74 (2009); Konstantinopoulos, P. A., et al., J Clin Oncol 28, 3555-3561 (2010)). However, to date there does not exist a diagnostic test that works across cancer diseases to accurately define a molecular subtype that demonstrates a deficiency in DNA damage repair, that can also predict sensitivity to any drug that directly or indirectly targets DNA damage repair across diseases.

What is therefore needed is a test that identifies DNA repair deficient tumors with sufficient accuracy to allow the stratification of patients into those who are likely to respond to chemotherapeutic agents that damage DNA, and those who should receive alternative therapies.

What is also needed is a molecular subtype classifier that is predictive of therapeutic responsiveness across different cancer types with sufficient accuracy.

SUMMARY OF THE INVENTION

The invention is directed to methods of using a collection of gene product markers expressed in cancer such that when some or all of the transcripts are over or under-expressed, they identify a subtype of cancer that has a deficiency in DNA damage repair. Designation of this subtype can be considered a diagnostic test as it is not related to any specific drug but rather describes the biology of the cancer in a manner that has utility in screening and selecting appropriate cancer therapies. The invention also provides methods for indicating responsiveness or resistance to DNA-damage therapeutic agents. In different aspects, this gene or gene product list may form the basis of a single parameter or a multiparametric predictive test that could be delivered using methods known in the art such as microarray, Q-PCR, immunohistochemistry, ELISA or other technologies that can quantify mRNA or protein expression.

In addition, the biological pathway described herein is a feature of cancer itself, similar to grade and stage, and as such, is not limited to a single cancer disease type. Therefore, the collection of genes or gene products may be used to predict responsiveness of cancer therapeutics across different cancer types in different tissues. In one embodiment of the invention, these genes or gene products are useful for evaluating both breast and ovarian cancer tumors.

The invention described herein is not limited to any one drug; it can be used to identify responders and non responders to any of a range of drugs that directly or indirectly affect DNA damage and/or DNA damage repair e.g. neoadjuvant 5-fluorouracil, anthracycline and cyclophosphamide based regimens such as FEC (5-fluorouracil/epirubicin/cyclophosphamide) and FAC (5-fluorouracil/Adriamycin/cyclophosphamide). In specific aspects this invention, it is useful for evaluating paclitaxel, fluorouracil, doxorubicin (Adriamycin), and cyclophosphamide (T/FAC) neoadjuvant treatment in breast cancer. In other aspects this invention, it is useful for evaluating platinum or platinum plus taxol treatment in ovarian cancer.

The present invention relates to prediction of response to drugs using different classifications of response, such as overall survival, progression free survival, radiological response, as defined by RECIST, complete response, partial response, stable disease and serological markers such as, but not limited to, PSA, CEA, CA125, CA15-3 and CA19-9. In specific embodiments this invention can be used to evaluate pathological complete response in breast cancer treated with FEC or FAC either alone or in the context of standard treatment, or RECIST and serum CA125 levels in ovarian cancer.

In another aspect, the present invention relates to the identification of a DNA damage response deficiency (DDRD) molecular subtype in breast and ovarian cancer. This molecular subtype can be detected by the use of two different gene classifiers—one being 40 genes in length and one being 44 genes in length. The DDRD classifier was first defined by a classifier consisting of 53 probesets on the Almac Breast Disease Specific Array (DSA™). So as to validate the functional relevance of this classifier in the context of its ability to predict response to DNA-damaging containing chemotherapy regimens, the classifier needed to be re-defined at a gene level. This would facilitate evaluation of the DDRD classifier using microarray data from independent datasets that were profiled on microarray platforms other than the Almac Breast DSA™. In order to facilitate defining the classifier at a gene level, the genes to which the Almac Breast DSA™ probesets map to needed to be defined. This involved the utilization of publicly available genome browser databases such as Ensembl and NCBI Reference Sequence. Results are provided only for the 44-gene DDRD classifier model, as this model supersedes that of the 40-gene DDRD classifier model. These results demonstrate that the classifier model is an effective and significant predictor of response to chemotherapy regimens that contain DNA damaging therapeutics.

The identification of the subtype by both the 40-gene classifier model and the 44-gene classifier model can be used to predict response to, and select patients for, standard breast and ovarian cancer therapeutic drug classes, including DNA damage causing agents and DNA repair targeted therapies.

In another aspect, the present invention relates to kits for conventional diagnostic uses listed above such as qPCR, microarray, and immunoassays such as immunohistochemistry, ELISA, Western blot and the like. Such kits include appropriate reagents and directions to assay the expression of the genes or gene products and quantify mRNA or protein expression.

The invention also provides methods for identifying DNA damage response-deficient (DDRD) human tumors. It is likely that this invention can be used to identify patients that are sensitive to and respond, or are resistant to and do not respond, to drugs that damage DNA directly, damage DNA indirectly or inhibit normal DNA damage signaling and/or repair processes.

The invention also relates to guiding conventional treatment of patients. The invention also relates to selecting patients for clinical trials where novel drugs of the classes that directly or indirectly affect DNA damage and/or DNA damage repair.

The present invention and methods accommodate the use of archived formalin fixed paraffin-embedded (FFPE) biopsy material, as well as fresh/frozen (FF) tissue, for assay of all transcripts in the invention, and are therefore compatible with the most widely available type of biopsy material. The expression level may be determined using RNA obtained from FFPE tissue, fresh frozen tissue or fresh tissue that has been stored in solutions such as RNAlater®.

BRIEF DESCRIPTION OF DRAWINGS

FIG. 2A, FIG. 2B, FIG. 2C, and FIG. 2D provide a diagramofbox plots comparing the AUC performance of each classification model under a 10 repeats of 5-fold cross validation for (FIG. 1A) the combined sample set, (FIG. 1B) the ER-negative sample set and (FIG. 1C) the ER-positive sample set. (FIG. 1D) Sensitivity plus specificity plot of the cross validation predictions used to select threshold. The maximum sensitivity plus specificity is 1.682 with a corresponding signature score of ~0.37.

(FIG. 8A) Western blot analysis confirming increased expression of BRCA1 in the HCC1937-BR cells compared with the HCC1937-EV cells. (FIG. 8B) Mean 44-gene model (DDRD) classifier score (±SEM) within the control vector-only transfected HCC1937 (HCC1937-EV) and HCC1937 with returned exogenous expression of BRCA1 (HCC1937-BR) cell-lines. Histogram representation of cell-viability of HCC1937 parental and HCC1937-BR cells under constant exposure to a range of concentrations of PARP inhibitor KU0058948 (FIG. 8C) and cisplatin (FIG. 8D).

DETAILED DESCRIPTION OF THE INVENTION

Figure 1A:
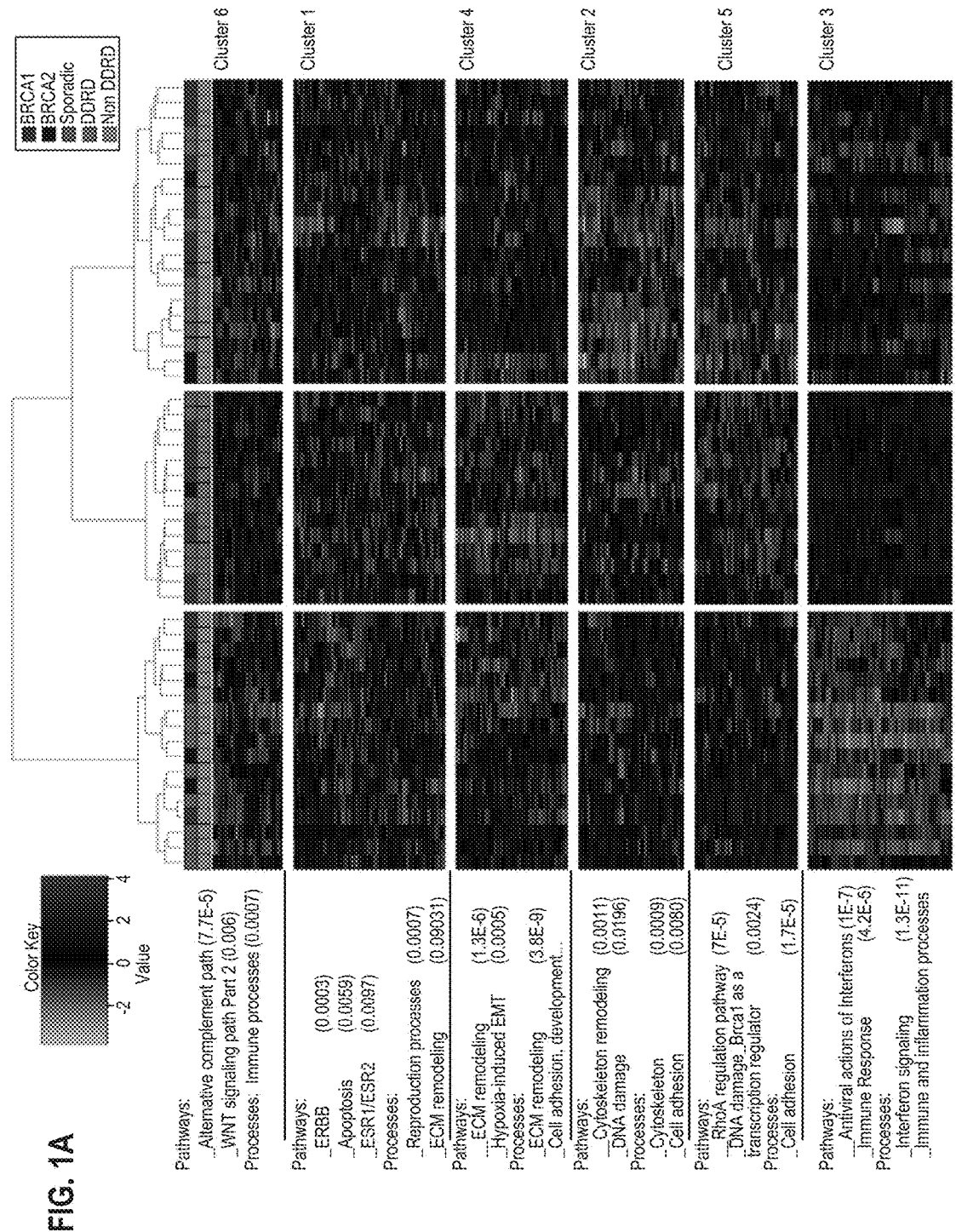
FIG. 1A and FIG. 1B provide a diagram representing the hierarchical analysis of ER-negative (FIG. 1A) and ER-positive (FIG. 1B) BRCA1/2 mutant and sporadic wildtype control breast samples. Probeset cluster groups are annotated on the right-hand side and pathway analysis of each probeset cluster group is annotated on the left-hand side of each image. The legend for each image indicates a sample's mutational status as well as the signature group each sample was assigned to for classifier generation.

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

The articles "a" and "an" are used herein to refer to one or to more than one (i.e., to at least one) of the grammatical object of the article. By way of example, "an element" means one element or more than one element, unless explicitly indicated to the contrary.

A major goal of current research efforts in cancer is to increase the efficacy of perioperative systemic therapy in patients by incorporating molecular parameters into clinical therapeutic decisions. Pharmacogenetics/genomics is the study of genetic/genomic factors involved in an individual's response to a foreign compound or drug. Agents or modulators which have a stimulatory or inhibitory effect on expression of a marker of the invention can be administered to individuals to treat (prophylactically or therapeutically) cancer in a patient. It is ideal to also consider the pharmacogenomics of the individual in conjunction with such treatment. Differences in metabolism of therapeutics may possibly lead to severe toxicity or therapeutic failure by altering the relationship between dose and blood concentration of the pharmacologically active drug. Thus, understanding the pharmacogenomics of an individual permits the selection of effective agents (e.g., drugs) for prophylactic or therapeutic treatments. Such pharmacogenomics can further be used to determine appropriate dosages and therapeutic regimens. Accordingly, the level of expression of a marker of the invention in an individual can be determined to thereby select appropriate agent(s) for therapeutic or prophylactic treatment of the individual.

The invention is directed to a unique collection of gene or gene product markers (hereinafter referred to as "biomarkers") expressed in a cancer tissue. In different aspects, this biomarker list may form the basis of a single parameter or multiparametric predictive test that could be delivered using methods known in the art such as microarray, Q-PCR, immunohistochemistry, ELISA or other technologies that can quantify mRNA or protein expression.

The present invention also relates to kits and methods that are useful for prognosis following cytotoxic chemotherapy or selection of specific treatments for cancer. Methods are provided such that when some or all of the transcripts are over or under-expressed, the expression profile indicates responsiveness or resistance to DNA-damage therapeutic agents. These kits and methods employ gene or gene product markers that are differentially expressed in tumors of patients with cancer. In one embodiment of the invention, the expression profiles of these biomarkers are correlated with clinical outcome (response or survival) in archival tissue samples under a statistical method or a correlation model to create a database or model correlating expression profile with responsiveness to one or more DNA-damage therapeutic agents. The predictive model may then be used to predict the responsiveness in a patient whose responsiveness to the DNA-damage therapeutic agent(s) is unknown. In many other embodiments, a patient population can be divided into at least two classes based on patients' clinical outcome, prognosis, or responsiveness to DNA-damage therapeutic agents, and the biomarkers are substantially correlated with a class distinction between these classes of patients. The biological pathways described herein are common to cancer as a disease, similar to grade and stage, and as such, the classifiers and methods are not limited to a single cancer disease type.

Predictive Marker Panels/Expression Classifiers

A unique collection of biomarkers as a genetic classifier expressed in a cancer tissue is provided that is useful in determining responsiveness or resistance to therapeutic agents, such as DNA-damage therapeutic agents, used to treat cancer. Such a collection may be termed a "marker panel", "expression classifier", or "classifier".

The biomarkers useful in the present methods are identified in Table 1. These biomarkers are identified as having predictive value to determine a patient response to a therapeutic agent, or lack thereof. Their expression correlates with the response to an agent, and more specifically, a DNA-damage therapeutic agent. By examining the expression of a collection of the identified biomarkers in a tumor, it is possible to determine which therapeutic agent or combination of agents will be most likely to reduce the growth rate of a cancer, and in some embodiments, breast or ovarian cancer cells. By examining a collection of identified transcript gene or gene product markers, it is also possible to determine which therapeutic agent or combination of agents will be the least likely to reduce the growth rate of a cancer. By examining the expression of a collection of biomarkers, it is therefore possible to eliminate ineffective or inappropriate therapeutic agents. Importantly, in certain embodiments, these determinations can be made on a patient-by-patient basis or on an agent-by-agent basis. Thus, one can determine whether or not a particular therapeutic regimen is likely to benefit a particular patient or type of patient, and/or whether a particular regimen should be continued.

TABLE 1A

| Sense genes (166) | | | | |
|---|---|---|---|---|
| Gene Symbol | EntrezGene ID | Almac Gene ID | Antisense of known genes (24) Almac Gene symbol | SEQ. ID NO: |
| ABCA12 | 26154 | | N/A | |
| ALDH3B2 | 222 | | N/A | |
| APOBEC3G | 60489 | | N/A | |
| APOC1 | 341 | | N/A | |
| APOL6 | 80830 | | N/A | |
| ARHGAP9 | 64333 | | N/A | |
| BAMBI | 25805 | | N/A | |
| BIK | 638 | | N/A | |
| BIRC3 | 330 | AS1_BIRC3 | Hs127799.0C7n9_at | 1 |
| BTN3A3 | 10384 | | N/A | |
| C12orf48 | 55010 | | N/A | |
| C17orf28 | 283987 | | N/A | |
| C1orf162 | 128346 | | N/A | |
| C1orf64 | 149563 | | N/A | |
| C1QA | 712 | | N/A | |
| C21orf70 | 85395 | | N/A | |
| C22orf32 | 91689 | | N/A | |
| C6orf211 | 79624 | | N/A | |
| CACNG4 | 27092 | | N/A | |
| CCDC69 | 26112 | | N/A | |
| CCL5 | 6352 | | N/A | |
| CCNB2 | 9133 | | N/A | |
| CCND1 | 595 | | N/A | |
| CCR7 | 1236 | | N/A | |
| CD163 | 9332 | | N/A | |
| CD2 | 914 | | N/A | |
| CD22 | 933 | | N/A | |
| CD24 | 100133941 | | N/A | |
| CD274 | 29126 | | N/A | |
| CD3D | 915 | | N/A | |
| CD3E | 916 | | N/A | |
| CD52 | 1043 | | N/A | |
| CD53 | 963 | | N/A | |
| CD79A | 973 | | N/A | |
| CDH1 | 999 | | N/A | |
| CDKN3 | 1033 | | N/A | |
| CECR1 | 51816 | | N/A | |
| CHEK1 | 1111 | | N/A | |
| CKMT1B | 1159 | | N/A | |
| CMPK2 | 129607 | | N/A | |
| CNTNAP2 | 26047 | | N/A | |
| COX16 | 51241 | | N/A | |
| CRIP1 | 1396 | | N/A | |
| CXCL10 | 3627 | | N/A | |
| CXCL9 | 4283 | | N/A | |
| CYBB | 1536 | | N/A | |
| CYP2B6 | 1555 | | N/A | |
| DDX58 | 23586 | | N/A | |
| DDX60L | 91351 | | N/A | |
| ERBB2 | 2064 | | N/A | |
| ETV7 | 51513 | | N/A | |
| FADS2 | 9415 | | N/A | |
| FAM26F | 441168 | | N/A | |
| FAM46C | 54855 | | N/A | |
| FASN | 2194 | | N/A | |
| FBP1 | 2203 | | N/A | |
| FBXO2 | 26232 | | N/A | |
| FKBP4 | 2288 | | N/A | |
| FLJ40330 | 645784 | | N/A | |

TABLE 1A-continued

| Sense genes (166) | | | | |
|---|---|---|---|---|
| Gene Symbol | EntrezGene ID | Almac Gene ID | Antisense of known genes (24) Almac Gene symbol | SEQ. ID NO: |
| FYB | 2533 | | N/A | |
| GBP1 | 2633 | | N/A | |
| GBP4 | 115361 | | N/A | |
| GBP5 | 115362 | AS1_GBP5 | BRMX.5143C1n2_at | 2 |
| GIMAP4 | 55303 | | N/A | |
| GLRX | 2745 | | N/A | |
| GLUL | 2752 | | N/A | |
| GVIN1 | 387751 | | N/A | |
| H2AFJ | 55766 | | N/A | |
| HGD | 3081 | | N/A | |
| HIST1H2BK | 85236 | | N/A | |
| HIST3H2A | 92815 | | N/A | |
| HLA-DOA | 3111 | | N/A | |
| HLA-DPB1 | 3115 | | N/A | |
| HMGB2 | 3148 | | N/A | |
| HMGB3 | 3149 | | N/A | |
| HSP90AA1 | 3320 | | N/A | |
| IDO1 | 3620 | | N/A | |
| IFI27 | 3429 | | N/A | |
| IFI44 | 10561 | | N/A | |
| IFI44L | 10964 | AS1_IFI44L | BRSA.1606C1n4_at | 3 |
| IFI6 | 2537 | | N/A | |
| IFIH1 | 64135 | | N/A | |
| IGJ | 3512 | AS1_IGJ | BRIH.1231C2n2_at | 4 |
| IKZF1 | 10320 | | N/A | |
| IL10RA | 3587 | | N/A | |
| IL2RG | 3561 | | N/A | |
| IL7R | 3575 | | N/A | |
| IMPAD1 | 54928 | | N/A | |
| IQGAP3 | 128239 | AS1_IQGAP3 | BRAD.30779_s_at | 5 |
| IRF1 | 3659 | | N/A | |
| ISG15 | 9636 | | N/A | |
| ITGAL | 3683 | | N/A | |
| KIAA1467 | 57613 | | N/A | |
| KIF20A | 10112 | | N/A | |
| KITLG | 4254 | | N/A | |
| KLRK1 | 22914 | | N/A | |
| KRT19 | 3880 | | N/A | |
| LAIR1 | 3903 | | N/A | |
| LCP1 | 3936 | | N/A | |
| LOC100289702 | 100289702 | | N/A | |
| LOC100294459 | 100294459 | AS1_LOC100294459 | BRSA.396C1n2_at | 6 |
| LOC150519 | 150519 | | N/A | |
| LOC439949 | 439949 | | N/A | |
| LYZ | 4069 | | N/A | |
| MAL2 | 114569 | | N/A | |
| MGC29506 | 51237 | | N/A | |
| MIAT | 440823 | | N/A | |
| MS4A1 | 931 | | N/A | |
| MX1 | 4599 | AS1_MX1 | BRMX.2948C3n7_at | 7 |
| NAPSB | 256236 | | N/A | |
| NCKAP1L | 3071 | | N/A | |
| NEK2 | 4751 | | N/A | |
| NLRC3 | 197358 | | N/A | |
| NLRC5 | 84166 | | N/A | |
| NPNT | 255743 | | N/A | |
| NQO1 | 1728 | | N/A | |
| OAS2 | 4939 | | N/A | |
| OAS3 | 4940 | | N/A | |
| PAQR4 | 124222 | | N/A | |
| PARP14 | 54625 | | N/A | |
| PARP9 | 83666 | | N/A | |
| PIK3CG | 5294 | | N/A | |
| PIM2 | 11040 | | N/A | |
| PLEK | 5341 | | N/A | |
| POU2AF1 | 5450 | | N/A | |
| PP14571 | 100130449 | | N/A | |
| PPP2R2C | 5522 | | N/A | |
| PSMB9 | 5698 | | N/A | |
| PTPRC | 5788 | | N/A | |
| RAC2 | 5880 | | N/A | |
| RAMP1 | 10267 | | N/A | |
| RARA | 5914 | | N/A | |
| RASSF7 | 8045 | | N/A | |

TABLE 1A-continued

Sense genes (166)

| Gene Symbol | EntrezGene ID | Almac Gene ID | Antisense of known genes (24) Almac Gene symbol | SEQ. ID NO: |
|---|---|---|---|---|
| RSAD2 | 91543 | | N/A | |
| RTP4 | 64108 | | N/A | |
| SAMD9 | 54809 | | N/A | |
| SAMD9L | 219285 | | N/A | |
| SASH3 | 54440 | | N/A | |
| SCD | 6319 | | N/A | |
| SELL | 6402 | | N/A | |
| SIX1 | 6495 | AS1_SIX1 | Hs539969.0C4n3_at | 8 |
| SLAMF7 | 57823 | | N/A | |
| SLC12A2 | 6558 | | N/A | |
| SLC9A3R1 | 9368 | AS1_SLC9A3R1 | Hs396783.3C1n4_at | 9 |
| SPOCK2 | 9806 | | N/A | |
| SQLE | 6713 | | N/A | |
| ST20 | 400410 | | N/A | |
| ST6GALNAC2 | 10610 | | N/A | |
| STAT1 | 6772 | AS1_STAT1 | BRMX.13670C1n2_at | 10 |
| STRA13 | 201254 | | N/A | |
| SUSD4 | 55061 | | N/A | |
| SYT12 | 91683 | | N/A | |
| TAP1 | 6890 | | N/A | |
| TBC1D10C | 374403 | | N/A | |
| TNFRSF13B | 23495 | | N/A | |
| TNFSF10 | 8743 | | N/A | |
| TOB1 | 10140 | AS1_TOB1 | BRAD.30243_at | 11 |
| TOM1L1 | 10040 | | N/A | |
| TRIM22 | 10346 | | N/A | |
| UBD | 10537 | AS1_UBD | BRMX.941C2n2_at | 12 |
| UBE2T | 29089 | | N/A | |
| UCK2 | 7371 | | N/A | |
| USP18 | 11274 | | N/A | |
| VNN2 | 8875 | | N/A | |
| XAF1 | 54739 | | N/A | |
| ZWINT | 11130 | | N/A | |
| | | AS1_C1QC | BRMX.4154C1n3_s_at | 13 |
| | | AS1_C2orf14 | BRAD.39498_at | 14 |
| | | AS1_EPSTI1 | BRAD.34868_s_at | 15 |
| | | AS1_GALNT6 | 5505575.0C1n42_at | 16 |
| | | AS1_HIST1H4H | BREM.1442_at | 17 |
| | | AS1_HIST2H4B | BRHP.827_s_at | 18 |
| | | AS2_HIST2H4B | BRRS.18322_s_at | 19 |
| | | AS3_HIST2H4B | BRRS.18792_s_at | 20 |
| | | AS1_KIAA1244 | Hs632609.0C1n37_at | 21 |
| | | AS1_LOC100287927 | Hs449575.0C1n22_at | 22 |
| | | AS1_LOC100291682 | BRAD.18827_s_at | 23 |
| | | AS1_LOC100293679 | BREM.2466_s_at | 24 |

TABLE 1B

Novel genes

| Gene symbol | SEQ ID NO |
|---|---|
| BRAD.2605_at | 25 |
| BRAD.33618_at | 26 |
| BRAD.36579_s_at | 27 |
| BRAD1_5440961_s_at | 28 |
| BRAD1_66786229_s_at | 29 |
| BREM.2104_at | 30 |
| BRAG_AK097020.1_at | 31 |
| BRAD.20415_at | 32 |
| BRAD.29668_at | 33 |
| BRAD.30228_at | 34 |
| BRAD.34830_at | 35 |
| BRAD.37011_s_at | 36 |
| BRAD.37762_at | 37 |
| BRAD.40217_at | 38 |
| BRAD1_4307876_at | 39 |
| BREM.2505_at | 40 |
| Hs149363.0CB4n5_s_at | 41 |
| Hs172587.9C1n9_at | 42 |
| Hs271955.16C1n9_at | 43 |
| Hs368433.18C1n6_at | 44 |
| Hs435736.0C1n27_s_at | 45 |
| Hs493096.15C1n6_at | 46 |
| Hs493096.2C1n15_s_at | 47 |
| Hs592929.0CB2n8_at | 48 |
| Hs79953.0C1n23_at | 49 |
| BRMX.2377C1n3_at | 50 |

All or a portion of the biomarkers recited in Table 1 may be used in a predictive biomarker panel. For example, biomarker panels selected from the biomarkers in Table 1 can be generated using the methods provided herein and can comprise between one, and all of the biomarkers set forth in Table 1 and each and every combination in between (e.g., four selected biomarkers, 16 selected biomarkers, 74 selected biomarkers, etc.). In some embodiments, the predictive biomarker set comprises at least 5, 10, 20, 40, 60, 100, 150, 200, or 300 or more biomarkers. In other embodiments, the predictive biomarker set comprises no more than 5, 10, 20, 40, 60, 100, 150, 200, 300, 400, 500, 600 or 700 biomarkers. In some embodiments, the predictive biomarker set includes a plurality of biomarkers listed in Table 1. In some embodiments the predictive biomarker set includes at least about 1%, about 5%, about 10%, about 20%, about 30%, about 40%, about 50%, about 60%, about 70%, about 80%, about 90%, about 95%, about 96%, about 97%, about 98%, or about 99% of the biomarkers listed in Table 1. Selected predictive biomarker sets can be assembled from the predictive biomarkers provided using methods described herein and analogous methods known in the art. In one embodiment, the biomarker panel contains all 203 biomarkers in Table 1. In another embodiment, the biomarker panel contains 40 or 44 biomarkers in Table 1 or 2.

Predictive biomarker sets may be defined in combination with corresponding scalar weights on the real scale with varying magnitude, which are further combined through linear or non-linear, algebraic, trigonometric or correlative means into a single scalar value via an algebraic, statistical learning, Bayesian, regression, or similar algorithms which together with a mathematically derived decision function on the scalar value provide a predictive model by which expression profiles from samples may be resolved into discrete classes of responder or non-responder, resistant or non-resistant, to a specified drug or drug class. Such predictive models, including biomarker membership, are developed by learning weights and the decision threshold, optimized for sensitivity, specificity, negative and positive predictive values, hazard ratio or any combination thereof, under cross-validation, bootstrapping or similar sampling techniques, from a set of representative expression profiles from historical patient samples with known drug response and/or resistance.

In one embodiment, the biomarkers are used to form a weighted sum of their signals, where individual weights can be positive or negative. The resulting sum ("decisive function") is compared with a pre-determined reference point or value. The comparison with the reference point or value may be used to diagnose, or predict a clinical condition or outcome.

As described above, one of ordinary skill in the art will appreciate that the biomarkers included in the classifier provided in Table 1 will carry unequal weights in a classifier for responsiveness or resistance to a therapeutic agent. Therefore, while as few as one sequence may be used to diagnose or predict an outcome such as responsiveness to therapeutic agent, the specificity and sensitivity or diagnosis or prediction accuracy may increase using more sequences.

As used herein, the term "weight" refers to the relative importance of an item in a statistical calculation. The weight of each biomarker in a gene expression classifier may be determined on a data set of patient samples using analytical methods known in the art.

In one embodiment the biomarker panel is directed to the 40 biomarkers detailed in Table 2A with corresponding ranks and weights detailed in the table or alternative rankings and weightings, depending, for example, on the disease setting. In another embodiment, the biomarker panel is directed to the 44 biomarkers detailed in Table 2B with corresponding ranks and weights detailed in the table or alternative rankings and weightings, depending, for example, on the disease setting. Tables 2A and 2B rank the biomarkers in order of decreasing weight in the classifier, defined as the rank of the average weight in the compound decision score function measured under cross-validation. Table 2C present the probe sets that represent the genes in Table 2A and 2B with reference to their sequence ID numbers. Table 2D presents the antisense probe sequences that were present on the array for the genes in the signatures.

TABLE 2A

Gene IDs and EntrezGene IDs for 40-gene DDRD classifier model with associated ranking and weightings
DDRD clissifier 40 gene model

| Rank | Genes Symbol | EntrezGene ID | Weights |
|---|---|---|---|
| 1 | GBP5 | 115362 | 0.022389581 |
| 2 | CXCL10 | 3627 | 0.021941734 |
| 3 | IDO1 | 3620 | 0.020991115 |
| 4 | MX1 | 4599 | 0.020098675 |
| 5 | IFI44L | 10964 | 0.018204957 |
| 6 | CD2 | 914 | 0.018080661 |
| 7 | PRAME | 23532 | 0.016850837 |
| 8 | ITGAL | 3683 | 0.016783359 |
| 9 | LRP4 | 4038 | −0.015129969 |
| 10 | SP140L | 93349 | 0.014646025 |
| 11 | APOL3 | 80833 | 0.014407174 |
| 12 | FOSB | 2354 | −0.014310521 |
| 13 | CDR1 | 1038 | −0.014209848 |
| 14 | RSAD2 | 91543 | 0.014177132 |
| 15 | TSPAN7 | 7102 | −0.014111562 |
| 16 | RAC2 | 5880 | 0.014093627 |
| 17 | FYB | 2533 | 0.01400475 |
| 18 | KLHDC7B | 113730 | 0.013298413 |
| 19 | GRB14 | 2888 | 0.013031204 |
| 20 | KIF26A | 26153 | −0.012942351 |
| 21 | CD274 | 29126 | 0.012651964 |
| 22 | CD109 | 135228 | −0.012239425 |
| 23 | ETV7 | 51513 | 0.011787297 |
| 24 | MFAP5 | 8076 | −0.011480443 |
| 25 | OLFM4 | 10562 | −0.011130113 |
| 26 | PI15 | 51050 | −0.010904326 |
| 27 | FAM19A5 | 25817 | −0.010500936 |
| 28 | NLRC5 | 84166 | 0.009593449 |
| 29 | EGR1 | 1958 | −0.008947963 |
| 30 | ANXA1 | 301 | −0.008373991 |
| 31 | CLDN10 | 9071 | −0.008165127 |
| 32 | ADAMTS4 | 9507 | −0.008109892 |
| 33 | ESR1 | 2099 | 0.007524594 |
| 34 | PTPRC | 5788 | 0.007258669 |
| 35 | EGFR | 1956 | −0.007176203 |
| 36 | NAT1 | 9 | 0.006165534 |
| 37 | LATS2 | 26524 | −0.005951091 |
| 38 | CYP2B6 | 1555 | 0.005838391 |
| 39 | PPP1R1A | 5502 | −0.003898835 |
| 40 | TERF1P1 | 348567 | 0.002706847 |

TABLE 2B

Gene IDs and EntrezGene IDs for 44-gene DDRD classifier model with associated ranking and weightings
DDRD Classifier-44 Gene Model (NA: genomic sequence)

| Rank | Gene symbol | EntrezGene ID | Weight |
|---|---|---|---|
| 1 | CXCL10 | 3627 | 0.023 |
| 2 | MX1 | 4599 | 0.0226 |
| 3 | IDO1 | 3620 | 0.0221 |
| 4 | IFI44L | 10964 | 0.0191 |
| 5 | CD2 | 914 | 0.019 |
| 6 | GBP5 | 115362 | 0.0181 |
| 7 | PRAME | 23532 | 0.0177 |
| 8 | ITGAL | 3683 | 0.0176 |
| 9 | LRP4 | 4038 | −0.0159 |
| 10 | APOL3 | 80833 | 0.0151 |
| 11 | CDR1 | 1038 | −0.0149 |
| 12 | FYB | 2533 | −0.0149 |
| 13 | TSPAN7 | 7102 | 0.0148 |
| 14 | RAC2 | 5880 | −0.0148 |
| 15 | KLHDC7B | 113730 | 0.014 |
| 16 | GRB14 | 2888 | 0.0137 |
| 17 | AC138128.1 | N/A | −0.0136 |

TABLE 2B-continued

Gene IDs and EntrezGene IDs for 44-gene DDRD classifier model with associated ranking and weightings
DDRD Classifier-44 Gene Model (NA: genomic sequence)

| Rank | Gene symbol | EntrezGene ID | Weight |
|---|---|---|---|
| 18 | KIF26A | 26153 | −0.0136 |
| 19 | CD274 | 29126 | 0.0133 |
| 20 | CD109 | 135228 | −0.0129 |
| 21 | ETV7 | 51513 | 0.0124 |
| 22 | MFAP5 | 8076 | −0.0121 |
| 23 | OLFM4 | 10562 | −0.0117 |
| 24 | PI15 | 51050 | −0.0115 |
| 25 | FOSB | 2354 | −0.0111 |
| 26 | FAM19A5 | 25817 | 0.0101 |
| 27 | NLRC5 | 84166 | −0.011 |
| 28 | PRICKLE1 | 144165 | −0.0089 |
| 29 | EGR1 | 1958 | −0.0086 |
| 30 | CLDN10 | 9071 | −0.0086 |
| 31 | ADAMTS4 | 9507 | −0.0085 |
| 32 | SP140L | 93349 | 0.0084 |
| 33 | ANXA1 | 301 | −0.0082 |
| 34 | RSAD2 | 91543 | 0.0081 |
| 35 | ESR1 | 2099 | 0.0079 |
| 36 | IKZF3 | 22806 | 0.0073 |
| 37 | OR2I1P | 442197 | 0.007 |
| 38 | EGFR | 1956 | −0.0066 |
| 39 | NAT1 | 9 | 0.0065 |
| 40 | LATS2 | 26524 | −0.0063 |
| 41 | CYP2B6 | 1555 | 0.0061 |
| 42 | PTPRC | 5788 | 0.0051 |
| 43 | PPP1R1A | 5502 | −0.0041 |
| 44 | AL137218.1 | N/A | −0.0017 |

TABLE 2C

Probe set IDs and SEQ Numbers for genes contained in 40- and 44-gene signature
Probe set IDs and SEQ Numbers for genes contained in 40 and 44 gene signature

| Gene Symbol | Probe Set ID | SEQ ID NO. |
|---|---|---|
| FYB | BRAD.10849_at | 83 |
| CLDN10 | BRAD.10890_at | 84 |
| PPP1R1A | BRAD.11026_at | 85 |
| PI15 | BRAD.12809_at | 86 |
| MFAP5 | BRAD.14326_s_at | 87 |
| ESR1 | BRAD.15436_s_at | 88 |
| FYB | BRAD.15833_s_at | 89 |
| ESR1 | BRAD.19080_s_at | 90 |
| TERF1P1 | BRAD.2707_at | 91 |
| PRICKLE1 | BRAD.27716_s_at | 92 |
| LATS2 | BRAD.28628_s_at | 93 |
| IKZF3 | BRAD.28643_at | 94 |
| MX1 | BRAD.28663_s_at | 95 |
| CD274 | BRAD.29038_at | 96 |
| FAM19A5 | BRAD.30917_at | 97 |
| LATS2 | BRAD.31470_at | 98 |
| EGFR | BRAD.32716_at | 99 |
| EGFR | BRAD.33042_at | 100 |
| EGFR | BRAD.33341_at | 101 |
| ANXA1 | BRAD.33405_at | 102 |
| EGFR | BRAD.33431_at | 103 |
| KLHDC7B | BRAD.35695_at | 104 |
| IKZF3 | BRAD.35710_at | 105 |
| PTPRC | BRAD.37907_at | 106 |
| TERF1P1 | BRAD.40353_at | 107 |
| EGFR | BRAD.40654_s_at | 108 |
| FYB | BRAD.4701_at | 109 |
| PTPRC | BRAD.5967_at | 110 |
| EGFR | BRAD.7701_at | 111 |
| ESR1 | BREM.1048_at | 112 |
| EGFR | BREM.1129_at | 113 |
| NAT1 | BREM.1226_at | 114 |

TABLE 2C-continued

Probe set IDs and SEQ Numbers for genes contained in 40- and 44-gene signature
Probe set IDs and SEQ Numbers for genes contained in 40 and 44 gene signature

| Gene Symbol | Probe Set ID | SEQ ID NO. |
|---|---|---|
| FOSB | BREM.1262_at | 115 |
| OR2I1P | BREM.130_at | 116 |
| ADAMTS4 | BREM.1689_s_at | 117 |
| CYP2B6 | BREM.2334_at | 118 |
| EGFR | BREM.2382_at | 119 |
| ETV7 | BREM.532_at | 120 |
| ANXA1 | BRHP.106_s_at | 121 |
| ESR1 | BRIH.10647C1n2_at | 122 |
| EGFR | BRIH.1453C1n2_at | 123 |
| EGR1 | BRIH.1518C1n4_at | 124 |
| ANXA1 | BRIH.2770C3n31_at | 125 |
| NAT1 | BRIH.365C1n2_at | 126 |
| IFI44L | BRIH.5410C1n7_at | 127 |
| MX1 | BRIH.5478C1n2_s_at | 128 |
| ESR1 | BRIH.5650C1n2_at | 129 |
| CD109 | BRIH.5952C1n2_s_at | 130 |
| CXCL10 | BRIH.7359C1n3_s_at | 131 |
| FYB | BRIHRC.10930C1n2_s_at | 132 |
| AC138128.1 | BRMX.13731C1n18_at | 133 |
| TERF1P1 | BRMX.25436C1n2_at | 134 |
| GBP5 | BRMX.25712C1n2_at | 135 |
| EGR1 | BRMX.3079C1n3_at | 136 |
| EGR1 | BRMX.3079C2n3_at | 137 |
| ESR1 | BRPD.10690C1n5_at | 138 |
| FYB | BRPD.4019C1n3_s_at | 139 |
| GBP5 | BRPD.5301C1n2_s_at | 140 |
| NLRC5 | BRRS.12588_at | 141 |
| GBP5 | BRRS.13369_s_at | 142 |
| RSAD2 | BRRS.13576_at | 143 |
| PTPRC | BRRS.13647_at | 144 |
| PTPRC | BRRS.13648_s_at | 145 |
| CD109 | BRRS.13767_at | 146 |
| SP140L | BRRS.13859_at | 147 |
| KLHDC7B | BRRS.13881_at | 148 |
| APOL3 | BRRS.14465_s_at | 149 |
| PRICKLE1 | BRRS.15053_at | 150 |
| CLDN10 | BRRS.16228_s_at | 151 |
| EGFR | BRRS.16746_s_at | 152 |
| EGFR | BRRS.16747_at | 153 |
| PRAME | BRRS.16948_s_at | 154 |
| TERF1P1 | BRRS.17863_s_at | 155 |
| TERF1P1 | BRRS.17909_s_at | 156 |
| AL137218.1 | BRRS.18137_at | 157 |
| KIF26A | BRRS.18652_s_at | 158 |
| FYB | BRRS.2573_s_at | 159 |
| CXCL10 | BRRS.2644_at | 160 |
| CD2 | BRRS.2783_s_at | 161 |
| EGR1 | BRRS.2935_at | 162 |
| IDO1 | BRRS.3099_at | 163 |
| ITGAL | BRRS.3131_at | 164 |
| LRP4 | BRRS.3220_at | 165 |
| MX1 | BRRS.3319_at | 166 |
| MX1 | BRRS.3319_s_at | 167 |
| RAC2 | BRRS.3645_s_at | 168 |
| MFAP5 | BRRS.4126_s_at | 169 |
| NAT1 | BRRS.455_at | 170 |
| CDR1 | BRRS.4562_at | 171 |
| ANXA1 | BRRS.487_s_at | 172 |
| GRB14 | BRRS.4891_s_at | 173 |
| TSPAN7 | BRRS.4996_at | 174 |
| CYP2B6 | BRRS.524_s_at | 175 |
| ADAMTS4 | BRRS.5356_at | 176 |
| EGFR | BRRS.5451_at | 177 |
| OLFM4 | BRRS.6371_at | 178 |
| FOSB | BRRS.6611_at | 179 |
| PPP1R1A | BRRS.6619_at | 180 |
| PPP1R1A | BRRS.6619-22_at | 181 |
| IFI44L | BRRS.6684_at | 182 |
| CD274 | BRRS.7616_at | 183 |
| LATS2 | BRRS.7901_at | 184 |
| ESR1 | BRRS.81_at | 185 |
| ESR1 | BRRS.81-22_at | 186 |

TABLE 2C-continued

Probe set IDs and SEQ Numbers for genes contained in 40- and 44-gene signature
Probe set IDs and SEQ Numbers for genes contained in 40 and 44 gene signature

| Gene Symbol | Probe Set ID | SEQ ID NO. |
|---|---|---|
| FAM19A5 | BRRS.8480_s_at | 187 |
| PI15 | BRRS.8711_at | 188 |
| ETV7 | BRRS.8900_s_at | 189 |
| EGR1 | BRSA.1686C1n5_at | 190 |
| RAC2 | BRSA.8072C1n2_s_at | 191 |
| SP140L | Hs369056.20C1n2_at | 192 |
| EGFR | Hs488293.0CB1n69_at | 193 |
| ANXA1 | Hs494173.0CB4n15_at | 194 |
| GBP5 | Hs513726.0C2n39_s_at | 195 |
| TERF1P1 | Hs514006.0C1n8_at | 196 |
| TERF1P1 | Hs522202.0C1n6_at | 197 |
| PRICKLE1 | Hs524348.0CB1n97_at | 198 |
| PRICKLE1 | Hs524348.2C1n5_s_at | 199 |
| NLRC5 | Hs528836.0C1n3_s_at | 200 |
| TERF1P1 | Hs591893.1C1n4_s_at | 201 |
| RSAD2 | Hs7155.0CB1n102_at | 202 |

TABLE 2D

Almac IDs and Almac Gene symbol and SEQ ID numbers for antisense probe sets in 40-gene signature
(D) Almac IDs and Almac Gene symbol and SEQ ID numbers for antisense probe sets in 40 gene signature

| Gene Symbol | EntrezGene ID (40) | Almac Gene ID (32) | Almac Gene symbol | SEQ ID NO: |
|---|---|---|---|---|
| ADAMTS4 | 9507 | | | |
| ANXA1 | 301 | | | |
| ANXA1 | 301 | AS1_ANXA1 | BRAD.33405_at | 51 |
| APOL3 | 80833 | | | |
| CD109 | 135228 | | | |
| CD2 | 914 | | | |
| CD274 | 29126 | | | |
| CD274 | 29126 | AS1_CD274 | Hs584242.2C1n64_at | 52 |
| CDR1 | 1038 | | | |
| CDR1 | 1038 | AS1_CDR1 | BRRS1RC_NM_004065_at | 53 |
| CLDN10 | 9071 | | | |
| CLDN10 | 9071 | AS1_CLDN10 | BRRS.8182_at | 54 |
| CXCL10 | 3627 | | | |
| CXCL10 | 3627 | AS1_CXCL10 | BRMX.13815C1n5_at | 55 |
| CYP2B6 | 1555 | | | |
| EGFR | 1956 | | | |
| EGFR | 1956 | AS1_EGFR | BRMX.2637C1n26_at | 56 |
| EGFR | 1956 | AS2_EGFR | BRAD.36737_at | 57 |
| EGFR | 1956 | AS3_EGFR | BRAD.3853_at | 58 |
| EGFR | 1956 | AS4_EGFR | BRAD1_19760734_at | 59 |
| EGR1 | 1958 | | | |
| EGR1 | 1958 | AS1_EGR1 | BRMX.2797C4n2_at | 60 |
| ESR1 | 2099 | | | |
| ESR1 | 2099 | AS1_ESR1 | BRMX.10399C1n5_at | 61 |
| ESR1 | 2099 | AS2_ESR1 | BRMX.8912C1n3_at | 62 |
| ETV7 | 51513 | | | |
| FAM19A5 | 25817 | | | |
| FOSB | 2354 | | | |
| FOSB | 2354 | AS1_FOSB | BRMX.13731C1n18_at | 63 |
| FYB | 2533 | | | |
| FYB | 2533 | AS1_FYB | BRAD.25947_at | 64 |
| GBP5 | 115362 | | | |
| GBP5 | 115362 | AS1_GBP5 | BRMX.5143C1n2(2)_at | 65 |
| GRB14 | 2888 | | | |
| IDO1 | 3620 | | | |
| IFI44L | 10964 | | | |
| IFI44L | 10964 | AS1_IFI44L | Hs633116.0C1n30_at | 66 |
| IFI44L | 10964 | AS2_IFI44L | BRSA.1606C1n4(2)_at | 67 |
| ITGAL | 3683 | | | |
| ITGAL | 3683 | AS1_ITGAL | BRAD.41047_at | 68 |
| ITGAL | 3683 | AS2_ITGAL | BRAD.4420_at | 69 |
| KIF26A | 26153 | | | |
| KLHDC7B | 113730 | | | |
| KLHDC7B | 113730 | AS1_KLHDC7B | Hs137007.0C1n9_at | 70 |
| LATS2 | 26524 | | | |
| LATS2 | 26524 | AS1_LATS2 | BRSA.18050C1n3_at | 71 |
| LRP4 | 4038 | | | |
| MFAP5 | 8076 | | | |
| MX1 | 4599 | | | |
| MX1 | 4599 | AS1_MX1 | BRMX.2948C3n7(2)_at | 72 |

TABLE 2D-continued

Almac IDs and Almac Gene symbol and SEQ ID numbers
for antisense probe sets in 40-gene signature
(D) Almac IDs and Almac Gene symbol and SEQ ID numbers for antisense probe
sets in 40 gene signature

| Gene Symbol | EntrezGene ID (40) | Almac Gene ID (32) | Almac Gene symbol | SEQ ID NO: |
|---|---|---|---|---|
| MX1 | 4599 | AS2_MX1 | Hs43047.0C4n40_at | 73 |
| MX1 | 4599 | AS2_MX1 | Hs926.1C10n7_at | 74 |
| NAT1 | 9 | | | |
| NLRC5 | 84166 | | | |
| NLRC5 | 84166 | AS1_NLRC5 | Hs528836.0CB6n98_s_at | 75 |
| OLFM4 | 10562 | | | |
| OLFM4 | 10562 | AS1_OLFM4 | BRMX.7284C1n6_at | 76 |
| PI15 | 51050 | | | |
| PI15 | 51050 | AS1_PI15 | BRAD1_19751014_at | 77 |
| PPP1R1A | 5502 | | | |
| PRAME | 23532 | | | |
| PTPRC | 5788 | | | |
| RAC2 | 5880 | | | |
| RAC2 | 5880 | AS1_RAC2 | BRMX.13502C1n6_at | 78 |
| RSAD2 | 91543 | | | |
| SP140L | 93349 | | | |
| SP140L | 93349 | AS1_SP140L | BRMX.1111C4n3_at | 79 |
| SP140L | 93349 | AS2_SP140L | Hs369056.9C26n3_at | 80 |
| TERF1P1 | 348567 | | | |
| TERF1P1 | 348567 | AS1_TERF1P1 | BRMX.24432C1n2_at | 81 |
| TERF1P1 | 348567 | AS2_TERF1P1 | BRRS.17773_at | 82 |
| TSPAN7 | 7102 | | | |

In different embodiments, subsets of the biomarkers listed in Table 2A and Table 2B may be used in the methods described herein. These subsets include but are not limited to biomarkers ranked 1-2, 1-3, 1-4, 1-5, 1-10, 1-20, 1-30, 1-40, 1-44, 6-10, 11-15, 16-20, 21-25, 26-30, 31-35, 36-40, 36-44, 11-20, 21-30, 31-40, and 31-44 in Table 2A or Table 2B. In one aspect, therapeutic responsiveness is predicted in an individual by conducting an assay on a biological sample from the individual and detecting biomarker values that each correspond to at least one of the biomarkers GBP5, CXCL10, IDO1 and MX1 and at least N additional biomarkers selected from the list of biomarkers in Table 2B, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36. As used herein, the term "biomarker" can refer to a gene, an mRNA, cDNA, an antisense transcript, a miRNA, a polypeptide, a protein, a protein fragment, or any other nucleic acid sequence or polypeptide sequence that indicates either gene expression levels or protein production levels. In some embodiments, when referring to a biomarker of CXCL10, IDO1, CD2, GBP5, PRAME, ITGAL, LRP4, APOL3, CDR1, FYB, TSPAN7, RAC2, KLHDC7B, GRB14, AC138128.1, KIF26A, CD274, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, or AL137218.1, the biomarker comprises an mRNA of CXCL10, IDO1, CD2, GBP5, PRAME, ITGAL, LRP4, APOL3, CDR1, FYB, TSPAN7, RAC2, KLHDC7B, GRB14, AC138128.1, KIF26A, CD274, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, or AL137218.1, respectively. In further or other embodiments, when referring to a biomarker of MX1, GBP5, IFI44L, BIRC3, IGJ, IQGAP3, LOC100294459, SIX1, SLC9A3R1, STAT1, TOB1, UBD, C1QC, C2orf14, EPSTI, GALNT6, HIST1H4H, HIST2H4B, KIAA1244, LOC100287927, LOC100291682, or LOC100293679, the biomarker comprises an antisense transcript of MX1, IFI44L, GBP5, BIRC3, IGJ, IQGAP3, LOC100294459, SIX1, SLC9A3R1, STAT1, TOB1, UBD, C1QC, C2orf14, EPSTI, GALNT6, HIST1H4H, HIST2H4B, KIAA1244, LOC100287927, LOC100291682, or LOC100293679, respectively.

In a further aspect, therapeutic responsiveness is predicted, or a cancer diagnosis is indicated, in an individual by conducting an assay on a biological sample from the individual and detecting biomarker values that each correspond to the biomarkers GBP5, CXCL10, IDO1 and MX1 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36. In a further aspect, therapeutic responsiveness is predicted, or a cancer diagnosis is indicated, in an individual by conducting an assay on a biological sample from the individual and detecting biomarker values that each correspond to the biomarker GBP5 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39. In a further aspect, therapeutic responsiveness is predicted, or a cancer diagnosis is indicated, in an individual by conducting an assay on a biological sample from the individual and detecting biomarker values that each correspond to the biomarker CXCL10 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39. In a further aspect, therapeutic responsiveness is predicted, or a cancer diagnosis is indicated, in an individual by conducting an assay on a biological sample from the individual and detecting biomarker values that each correspond to the biomarker IDO1 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39. In a further aspect, therapeutic responsiveness is predicted, or a cancer diagnosis is indicated, in an individual by conducting an assay on a biological sample from the individual and detecting biomarker values that each correspond to the biomarker MX-1 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39.

In a further aspect, therapeutic responsiveness is predicted, or a cancer diagnosis is indicated, in an individual by conducting an assay on a biological sample from the individual and detecting biomarker values that each correspond to at least two of the biomarkers CXCL10, MX1, IDO1 and IFI44L and at least N additional biomarkers selected from the list of biomarkers in Table 2B, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In a further aspect, therapeutic responsiveness is predicted, or a cancer diagnosis is indicated, in an individual by conducting an assay on a biological sample from the individual and detecting biomarker values that each correspond to the biomarkers CXCL10, MX1, IDO1 and IFI44L and one of at least N additional biomarkers selected from the list of biomarkers in Table 2B, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In a further aspect, therapeutic responsiveness is predicted, or a cancer diagnosis is indicated, in an individual by conducting an assay on a biological sample from the individual and detecting biomarker values that each correspond to the biomarker CXCL10 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43. In a further aspect, therapeutic responsiveness is predicted, or a cancer diagnosis is indicated, in an individual by conducting an assay on a biological sample from the individual and detecting biomarker values that each correspond to the biomarker MX1 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43. In a further aspect, therapeutic responsiveness is predicted, or a cancer diagnosis is indicated, in an individual by conducting an assay on a biological sample from the individual and detecting biomarker values that each correspond to the biomarker IDO1 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43. In a further aspect, therapeutic responsiveness is predicted, or a cancer diagnosis is indicated, in an individual by conducting an assay on a biological sample from the individual and detecting biomarker values that each correspond to the biomarker IFI44L and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43.

In other embodiments, the probes listed in Table 2C (SEQ ID NOs:83-202), or subsets thereof, may be used in the methods described herein. These subsets include but are not limited to a subset of SEQ ID NOs corresponding to one or more of GBP5, CXCL10, IDO1, MX1, IF1441, CD2, PRAME, ITGAL, LRP4, and APOL3. In other embodiments, the probes correspond to all of the biomarkers CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR211P, EGFR, NAT1, LATS2, CYP2B6, PTPRC, PPP1R1A, and AL137218.1. It should be understood that each subset can include multiple probes directed to the same biomarker. For example, the probes represented by SEQ ID NOs: 135, 140, 142 and 195 are all directed to GBP5. Accordingly, a subset containing probes directed or corresponding to GBP5 includes one or more of SEQ ID NOs: 135, 140, 142 and 195. A subset containing probes directed to or corresponding to CXCL10 includes one or more of SEQ ID NOs: 131 and 160.

Measuring Gene Expression Using Classifier Models

A variety of methods have been utilized in an attempt to identify biomarkers and diagnose disease. For protein-based markers, these include two-dimensional electrophoresis, mass spectrometry, and immunoassay methods. For nucleic acid markers, these include mRNA expression profiles, microRNA profiles, FISH, serial analysis of gene expression (SAGE), methylation profiles, and large-scale gene expression arrays.

When a biomarker indicates or is a sign of an abnormal process, disease or other condition in an individual, that biomarker is generally described as being either over-expressed or under-expressed as compared to an expression level or value of the biomarker that indicates or is a sign of a normal process, an absence of a disease or other condition in an individual. "Up-regulation", "up-regulated", "over-expression", "over-expressed", and any variations thereof are used interchangeably to refer to a value or level of a biomarker in a biological sample that is greater than a value or level (or range of values or levels) of the biomarker that is typically detected in similar biological samples from healthy or normal individuals. The terms may also refer to a value or level of a biomarker in a biological sample that is greater than a value or level (or range of values or levels) of the biomarker that may be detected at a different stage of a particular disease.

"Down-regulation", "down-regulated", "under-expression", "under-expressed", and any variations thereof are used interchangeably to refer to a value or level of a biomarker in a biological sample that is less than a value or level (or range of values or levels) of the biomarker that is typically detected in similar biological samples from healthy or normal individuals. The terms may also refer to a value or level of a biomarker in a biological sample that is less than a value or level (or range of values or levels) of the biomarker that may be detected at a different stage of a particular disease.

Further, a biomarker that is either over-expressed or under-expressed can also be referred to as being "differentially expressed" or as having a "differential level" or "differential value" as compared to a "normal" expression level or value of the biomarker that indicates or is a sign of a normal process or an absence of a disease or other condition in an individual. Thus, "differential expression" of a biomarker can also be referred to as a variation from a "normal" expression level of the biomarker.

The terms "differential biomarker expression" and "differential expression" are used interchangeably to refer to a biomarker whose expression is activated to a higher or lower level in a subject suffering from a specific disease, relative to its expression in a normal subject, or relative to its expression in a patient that responds differently to a particular therapy or has a different prognosis. The terms also include biomarkers whose expression is activated to a higher or lower level at different stages of the same disease. It is also understood that a differentially expressed biomarker may be either activated or inhibited at the nucleic acid level or protein level, or may be subject to alternative splicing to result in a different polypeptide product. Such differences may be evidenced by a variety of changes including mRNA levels, miRNA levels, antisense transcript levels, or protein surface expression, secretion or other partitioning of a polypeptide. Differential biomarker expression may include a comparison of expression between two or more genes or their gene products; or a comparison of the ratios of the expression between two or more genes or their gene products; or even a comparison of two differently processed products of the same gene, which differ between normal subjects and subjects suffering from a disease; or between various stages of the same disease. Differential expression includes both quantitative, as well as qualitative, differences in the temporal or cellular expression pattern in a biomarker among, for example, normal and diseased cells, or among cells which have undergone different disease events or disease stages.

In certain embodiments, the expression profile obtained is a genomic or nucleic acid expression profile, where the amount or level of one or more nucleic acids in the sample is determined. In these embodiments, the sample that is assayed to generate the expression profile employed in the diagnostic or prognostic methods is one that is a nucleic acid sample. The nucleic acid sample includes a population of nucleic acids that includes the expression information of the phenotype determinative biomarkers of the cell or tissue being analyzed. In some embodiments, the nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as isolated, amplified, or employed to prepare cDNA, cRNA, etc., as is known in the field of differential gene expression. Accordingly, determining the level of mRNA in a sample includes preparing cDNA or cRNA from the mRNA and subsequently measuring the cDNA or cRNA. The sample is typically prepared from a cell or tissue harvested from a subject in need of treatment, e.g., via biopsy of tissue, using standard protocols, where cell types or tissues from which such nucleic acids may be generated include any tissue in which the expression pattern of the to be determined phenotype exists, including, but not limited to, disease cells or tissue, body fluids, etc.

The expression profile may be generated from the initial nucleic acid sample using any convenient protocol. While a variety of different manners of generating expression profiles are known, such as those employed in the field of differential gene expression/biomarker analysis, one representative and convenient type of protocol for generating expression profiles is array-based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Creating a Biomarker Expression Classifier

In one embodiment, the relative expression levels of biomarkers in a cancer tissue are measured to form a gene expression profile. The gene expression profile of a set of biomarkers from a patient tissue sample is summarized in the form of a compound decision score and compared to a score threshold that is mathematically derived from a training set of patient data. The score threshold separates a patient group based on different characteristics such as, but not limited to, responsiveness/non-responsiveness to treatment. The patient training set data is preferably derived from cancer tissue samples having been characterized by prognosis, likelihood of recurrence, long term survival, clinical outcome, treatment response, diagnosis, cancer classification, or personalized genomics profile. Expression profiles, and corresponding decision scores from patient samples may be correlated with the characteristics of patient samples in the training set that are on the same side of the mathematically derived score decision threshold. The threshold of the linear classifier scalar output is optimized to maximize the sum of sensitivity and specificity under cross-validation as observed within the training dataset.

The overall expression data for a given sample is normalized using methods known to those skilled in the art in order to correct for differing amounts of starting material, varying efficiencies of the extraction and amplification reactions, etc. Using a linear classifier on the normalized data to make a diagnostic or prognostic call (e.g. responsiveness or resistance to therapeutic agent) effectively means to split the data space, i.e. all possible combinations of expression values for all genes in the classifier, into two disjoint halves by means of a separating hyperplane. This split is empirically derived on a large set of training examples, for example from patients showing responsiveness or resistance to a therapeutic agent. Without loss of generality, one can assume a certain fixed set of values for all but one biomarker, which would automatically define a threshold value for this remaining biomarker where the decision would change from, for example, responsiveness or resistance to a therapeutic agent. Expression values above this dynamic threshold would then either indicate resistance (for a biomarker with a negative weight) or responsiveness (for a biomarker with a positive weight) to a therapeutic agent. The precise value of this threshold depends on the actual measured expression profile of all other biomarkers within the classifier, but the general indication of certain biomarkers remains fixed, i.e. high values or "relative over-expression" always contributes to either a responsiveness (genes with a positive weight) or resistance (genes with a negative weights). Therefore, in the context of the overall gene expression classifier, relative expression can indicate if either up- or down-regulation of a certain biomarker is indicative of responsiveness or resistance to a therapeutic agent.

In one embodiment, the biomarker expression profile of a patient tissue sample is evaluated by a linear classifier. As used herein, a linear classifier refers to a weighted sum of the individual biomarker intensities into a compound decision score ("decision function"). The decision score is then compared to a pre-defined cut-off score threshold, corresponding to a certain set-point in terms of sensitivity and specificity which indicates if a sample is above the score threshold (decision function positive) or below (decision function negative).

Effectively, this means that the data space, i.e. the set of all possible combinations of biomarker expression values, is split into two mutually exclusive halves corresponding to different clinical classifications or predictions, e.g. one corresponding to responsiveness to a therapeutic agent and the other to resistance. In the context of the overall classifier, relative over-expression of a certain biomarker can either increase the decision score (positive weight) or reduce it (negative weight) and thus contribute to an overall decision of, for example, responsiveness or resistance to a therapeutic agent.

The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., ovarian cancer samples and normal or control samples). ROC curves are useful for plotting the performance of a particular feature (e.g., any of the biomarkers described herein and/or any item of additional biomedical information) in distinguishing between two populations (e.g., individuals responding and not responding to a therapeutic agent). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

The interpretation of this quantity, i.e. the cut-off threshold responsiveness or resistance to a therapeutic agent, is derived in the development phase ("training") from a set of patients with known outcome. The corresponding weights and the responsiveness/resistance cut-off threshold for the decision score are fixed a priori from training data by methods known to those skilled in the art. In a preferred embodiment of the present method, Partial Least Squares Discriminant Analysis (PLS-DA) is used for determining the weights. (L. Ståhle, S. Wold, J. Chemom. 1 (1987) 185-196; D. V. Nguyen, D. M. Rocke, Bioinformatics 18 (2002) 39-50). Other methods for performing the classification, known to those skilled in the art, may also be with the methods described herein when applied to the transcripts of a cancer classifier.

Different methods can be used to convert quantitative data measured on these biomarkers into a prognosis or other predictive use. These methods include, but not limited to methods from the fields of pattern recognition (Duda et al. Pattern Classification, $2^{nd}$ ed., John Wiley, New York 2001), machine learning (Schölkopf et al. Learning with Kernels, MIT Press, Cambridge 2002, Bishop, Neural Networks for Pattern Recognition, Clarendon Press, Oxford 1995), statistics (Hastie et al. The Elements of Statistical Learning, Springer, New York 2001), bioinformatics (Dudoit et al., 2002, J. Am. Statist. Assoc. 97:77-87, Tibshirani et al., 2002, Proc. Natl. Acad. Sci. USA 99:6567-6572) or chemometrics (Vandeginste, et al., Handbook of Chemometrics and Qualimetrics, Part B, Elsevier, Amsterdam 1998).

In a training step, a set of patient samples for both responsiveness/resistance cases are measured and the prediction method is optimised using the inherent information from this training data to optimally predict the training set or a future sample set. In this training step, the used method is trained or parameterised to predict from a specific intensity pattern to a specific predictive call. Suitable transformation or pre-processing steps might be performed with the measured data before it is subjected to the prognostic method or algorithm.

In a preferred embodiment of the invention, a weighted sum of the pre-processed intensity values for each transcript is formed and compared with a threshold value optimised on the training set (Duda et al. Pattern Classification, $2^{nd}$ ed., John Wiley, New York 2001). The weights can be derived by a multitude of linear classification methods, including but not limited to Partial Least Squares (PLS, (Nguyen et al., 2002, Bioinformatics 18 (2002) 39-50)) or Support Vector Machines (SVM, (Schölkopf et al. Learning with Kernels, MIT Press, Cambridge 2002)).

In another embodiment of the invention, the data is transformed non-linearly before applying a weighted sum as described above. This non-linear transformation might include increasing the dimensionality of the data. The non-linear transformation and weighted summation might also be performed implicitly, e.g. through the use of a kernel function. (Schölkopf et al. Learning with Kernels, MIT Press, Cambridge 2002).

In another embodiment of the invention, a new data sample is compared with two or more class prototypes, being either real measured training samples or artificially created prototypes. This comparison is performed using suitable similarity measures, for example, but not limited to Euclidean distance (Duda et al. Pattern Classification, $2^{nd}$ ed., John Wiley, New York 2001), correlation coefficient (Van't Veer, et al. 2002, Nature 415:530) etc. A new sample is then assigned to the prognostic group with the closest prototype or the highest number of prototypes in the vicinity.

In another embodiment of the invention, decision trees (Hastie et al., The Elements of Statistical Learning, Springer, New York 2001) or random forests (Breiman, Random Forests, Machine Learning 45:5 2001) are used to make a prognostic call from the measured intensity data for the transcript set or their products.

In another embodiment of the invention neural networks (Bishop, Neural Networks for Pattern Recognition, Clarendon Press, Oxford 1995) are used to make a prognostic call from the measured intensity data for the transcript set or their products.

In another embodiment of the invention, discriminant analysis (Duda et al., Pattern Classification, $2^{nd}$ ed., John Wiley, New York 2001), comprising but not limited to linear, diagonal linear, quadratic and logistic discriminant analysis, is used to make a prognostic call from the measured intensity data for the transcript set or their products.

In another embodiment of the invention, Prediction Analysis for Microarrays (PAM, (Tibshirani et al., 2002, Proc. Natl. Acad. Sci. USA 99:6567-6572)) is used to make a prognostic call from the measured intensity data for the transcript set or their products.

In another embodiment of the invention, Soft Independent Modelling of Class Analogy (SIMCA, (Wold, 1976, Pattern Recogn. 8:127-139)) is used to make a predictive call from the measured intensity data for the transcript set or their products.

Therapeutic Agents

As described above, the methods described herein permit the classification of a patient as responsive or non-responsive to a therapeutic agent that targets tumors with abnormal DNA repair (hereinafter referred to as a "DNA-damage therapeutic agent"). As used herein "DNA-damage therapeutic agent" includes agents known to damage DNA directly, agents that prevent DNA damage repair, agents that inhibit DNA damage signaling, agents that inhibit DNA damage induced cell cycle arrest, and agents that inhibit processes indirectly leading to DNA damage. Some current such therapeutics used to treat cancer include, but are not limited to, the following DNA-damage therapeutic agents.

1) DNA Damaging Agents:
   a. Alkylating agents (platinum containing agents such as cisplatin, carboplatin, and oxaliplatin; cyclophosphamide; busulphan).
   b. Topoisomerase I inhibitors (irinotecan; topotecan)
   c. Topisomerase II inhibitors (etoposide; anthracyclines such as doxorubicin and epirubicin)
   d. Ionising radiation
2) DNA Repair Targeted Therapies
   a. Inhibitors of Non-homologous end-joining (DNA-PK inhibitors, Nu7441, NU7026)
   b. Inhibitors of homologous recombination
   c. Inhibitors of nucleotide excision repair
   d. Inhibitors of base excision repair (PARP inhibitors, AG014699, AZD2281, ABT-888, MK4827, BSI-201, INO-1001, TRC-102, APEX 1 inhibitors, APEX 2 inhibitors, Ligase III inhibitors
   e. Inhibitors of the Fanconi anemia pathway
3) Inhibitors of DNA Damage Signalling
   a. ATM inhibitors (CP466722, KU-55933)
   b. CHK 1 inhibitors (XL-844, UCN-01, AZD7762, PF00477736)
   c. CHK 2 inhibitors (XL-844, AZD7762, PF00477736)
4) Inhibitors of DNA Damage Induced Cell Cycle Arrest
   a. Wee1 kinase inhibitors
   b. CDC25a, b or c inhibitors
5) Inhibition of Processes Indirectly Leading to DNA Damage
   a. Histone deacetylase inhibitors
   b. Heat shock protein inhibitors (geldanamycin, AUY922), Diseases and Tissue Sources The predictive classifiers described herein are useful for determining responsiveness or resistance to a therapeutic agent for treating cancer. The biological pathway described herein is a feature of cancer itself, similar to grade and stage, and as such, is not limited to a single cancer disease type. Therefore, the collection of genes or gene products may be used to predict responsiveness of cancer therapeutics across different cancer types in different tissues. In one embodiment, this collection of genes or gene products is useful for evaluating both breast and ovarian cancer tumors.

As used herein, cancer includes, but is not limited to, leukemia, brain cancer, prostate cancer, liver cancer, ovarian cancer, stomach cancer, colorectal cancer, throat cancer, breast cancer, skin cancer, melanoma, lung cancer, sarcoma, cervical cancer, testicular cancer, bladder cancer, endocrine cancer, endometrial cancer, esophageal cancer, glioma, lymphoma, neuroblastoma, osteosarcoma, pancreatic cancer, pituitary cancer, renal cancer, and the like.

In one embodiment, the methods described herein refer to cancers that are treated with chemotherapeutic agents of the classes DNA damaging agents, DNA repair target therapies, inhibitors of DNA damage signalling, inhibitors of DNA damage induced cell cycle arrest and inhibition of processes indirectly leading to DNA damage, but not limited to these classes. Each of these chemotherapeutic agents is considered a "DNA-damage therapeutic agent" as the term is used herein.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, breath, urine, semen, saliva, meningeal fluid, amniotic fluid, glandular fluid, lymph fluid, nipple aspirate, bronchial aspirate, synovial fluid, joint aspirate, ascites, cells, a cellular extract, and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual.

In such cases, the target cells may be tumor cells, for example colon cancer cells or stomach cancer cells. The target cells are derived from any tissue source, including human and animal tissue, such as, but not limited to, a newly obtained sample, a frozen sample, a biopsy sample, a sample of bodily fluid, a blood sample, preserved tissue such as a paraffin-embedded fixed tissue sample (i.e., a tissue block), or cell culture.

Methods and Kits

Kits for Gene Expression Analysis

Reagents, tools, and/or instructions for performing the methods described herein can be provided in a kit. For example, the kit can contain reagents, tools, and instructions for determining an appropriate therapy for a cancer patient. Such a kit can include reagents for collecting a tissue sample from a patient, such as by biopsy, and reagents for processing the tissue. The kit can also include one or more reagents for performing a biomarker expression analysis, such as reagents for performing RT-PCR, qPCR, northern blot, proteomic analysis, or immunohistochemistry to determine expression levels of biomarkers in a sample of a patient. For example, primers for performing RT-PCR, probes for performing northern blot analyses, and/or antibodies for performing proteomic analysis such as Western blot, immunohistochemistry and ELISA analyses can be included in such kits. Appropriate buffers for the assays can also be included. Detection reagents required for any of these assays can also be included. The appropriate reagents and methods are described in further detail below.

The kits featured herein can also include an instruction sheet describing how to perform the assays for measuring biomarker expression. The instruction sheet can also include instructions for how to determine a reference cohort, including how to determine expression levels of biomarkers in the reference cohort and how to assemble the expression data to establish a reference for comparison to a test patient. The instruction sheet can also include instructions for assaying biomarker expression in a test patient and for comparing the expression level with the expression in the reference cohort to subsequently determine the appropriate chemotherapy for the test patient. Methods for determining the appropriate chemotherapy are described above and can be described in detail in the instruction sheet.

Informational material included in the kits can be descriptive, instructional, marketing or other material that relates to the methods described herein and/or the use of the reagents for the methods described herein. For example, the informational material of the kit can contain contact information, e.g., a physical address, email address, website, or telephone number, where a user of the kit can obtain substantive information about performing a gene expression analysis and interpreting the results, particularly as they apply to a human's likelihood of having a positive response to a specific therapeutic agent.

The kits featured herein can also contain software necessary to infer a patient's likelihood of having a positive response to a specific therapeutic agent from the biomarker expression.

a) Gene Expression Profiling Methods

Measuring mRNA in a biological sample may be used as a surrogate for detection of the level of the corresponding protein in the biological sample. Thus, any of the biomarkers or biomarker panels described herein can also be detected by detecting the appropriate RNA. Methods of gene expression profiling include, but are not limited to, microarray, RT-PCT, qPCR, northern blots, SAGE, mass spectrometry.

mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

miRNA molecules are small RNAs that are non-coding but may regulate gene expression. Any of the methods suited to the measurement of mRNA expression levels can also be used for the corresponding miRNA. Recently many laboratories have investigated the use of miRNAs as biomarkers for disease. Many diseases involve widespread transcriptional regulation, and it is not surprising that miRNAs might find a role as biomarkers. The connection between miRNA concentrations and disease is often even less clear than the connections between protein levels and disease, yet the value of miRNA biomarkers might be substantial. Of course, as with any RNA expressed differentially during disease, the problems facing the development of an in vitro diagnostic product will include the requirement that the miRNAs survive in the diseased cell and are easily extracted for analysis, or that the miRNAs are released into blood or other matrices where they must survive long enough to be measured. Protein biomarkers have similar requirements, although many potential protein biomarkers are secreted intentionally at the site of pathology and function, during disease, in a paracrine fashion. Many potential protein biomarkers are designed to function outside the cells within which those proteins are synthesized.

Gene expression may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an $F(ab')_2$ fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

The foregoing assays enable the detection of biomarker values that are useful in methods for predicting responsiveness of a cancer therapeutic agent, where the methods comprise detecting, in a biological sample from an individual, at least N biomarker values that each correspond to a biomarker selected from the group consisting of the biomarkers provided in Tables 1 or 2, wherein a classification, as described in detail below, using the biomarker values indicates whether the individual will be responsive to a therapeutic agent. While certain of the described predictive biomarkers are useful alone for predicting responsiveness to a therapeutic agent, methods are also described herein for the grouping of multiple subsets of the biomarkers that are each useful as a panel of two or more biomarkers. Thus, various embodiments of the instant application provide combinations comprising N biomarkers, wherein N is at least three biomarkers. It will be appreciated that N can be selected to be any number from any of the above-described ranges, as well as similar, but higher order, ranges. In accordance with any of the methods described herein, biomarker values can be detected and classified individually or they can be detected and classified collectively, as for example in a multiplex assay format.

b) Microarray Methods

In one embodiment, the present invention makes use of "oligonucleotide arrays" (also called herein "microarrays"). Microarrays can be employed for analyzing the expression of biomarkers in a cell, and especially for measuring the expression of biomarkers of cancer tissues.

In one embodiment, biomarker arrays are produced by hybridizing detectably labeled polynucleotides representing the mRNA transcripts present in a cell (e.g., fluorescently-labeled cDNA synthesized from total cell mRNA or labeled cRNA) to a microarray. A microarray is a surface with an ordered array of binding (e.g., hybridization) sites for products of many of the genes in the genome of a cell or organism, preferably most or almost all of the genes. Microarrays can be made in a number of ways known in the art. However produced, microarrays share certain characteristics. The arrays are reproducible, allowing multiple copies of a given array to be produced and easily compared with each other. Preferably the microarrays are small, usually smaller than 5 $cm^2$, and they are made from materials that are stable under binding (e.g., nucleic acid hybridization) conditions. A given binding site or unique set of binding sites in the microarray will specifically bind the product of a single gene in the cell. In a specific embodiment, positionally addressable arrays containing affixed nucleic acids of known sequence at each location are used.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene/biomarker. For example, when detectably labeled (e.g., with a fluorophore) cDNA or cRNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal. Nucleic acid hybridization and wash conditions are chosen so that the probe "specifically binds" or "specifically hybridizes' to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can be demonstrated that specific hybridization conditions result in specific hybridization by carrying out a hybridization assay including negative controls using routine experimentation.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65 C for 4 hours followed by washes at 25° C. in low stringency wash buffer (1×SSC plus 0.2% SDS) followed by 10 minutes at 25° C. in high stringency wash buffer (0.1 SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B.V. (1993) and Kricka, "Nonisotopic DNA Probe Techniques", Academic Press, San Diego, Calif. (1992).

c) Immunoassay Methods

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Clinical Uses

In some embodiments, methods are provided for identifying and/or selecting a cancer patient who is responsive to a therapeutic regimen. In particular, the methods are directed to identifying or selecting a cancer patient who is responsive to a therapeutic regimen that includes administering an agent that directly or indirectly damages DNA. Methods are also provided for identifying a patient who is non-responsive to a therapeutic regimen. These methods typically include determining the level of expression of a collection of predictive markers in a patient's tumor (primary, metastatic or other derivatives from the tumor such as, but not limited to, blood, or components in blood, urine, saliva and other bodily fluids)(e.g., a patient's cancer cells), comparing the level of expression to a reference expression level, and identifying whether expression in the sample includes a pattern or profile of expression of a selected predictive biomarker or biomarker set which corresponds to response or non-response to therapeutic agent.

In some embodiments a method of predicting responsiveness of an individual to a DNA-damage therapeutic agent comprises the following steps: obtaining a test sample from the individual; measuring expression levels of one or more biomarkers in the test sample, wherein the one or more biomarkers are selected from the group consisting of CXCL10, MX1, IDO1, IF144L, CD2, GBP5, PRAME, ITGAL, LRP4, and APOL3; deriving a test score that captures the expression levels; providing a threshold score comprising information correlating the test score and responsiveness; and comparing the test score to the threshold score; wherein responsiveness is predicted when the test score exceeds the threshold score. One of ordinary skill in the art can determine an appropriate threshold score, and appropriate biomarker weightings, using the teachings provided herein including the teachings of Example 1.

In other embodiments, the method of predicting responsiveness of an individual to a DNA-damage therapeutic agent comprises measuring the expression levels of one or more biomarkers in the test sample, wherein the one or more biomarkers are selected from the group consisting of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR211P, EGFR, NAT1, LATS2, CYP2B6, PTPRC, PPP1R1A, and AL137218.1. Tables 2A and 2B provide exemplary gene signatures (or gene classifiers) wherein the biomarkers consist of 40 or 44 of the gene products listed therein, respectively, and wherein a threshold score is derived from the individual gene product weightings listed therein. In one of these embodiments wherein the biomarkers consist of the 44 gene products listed in Table 2B, and the biomarkers are associated with the weightings provided in Table 2B, a test score that exceeds a threshold score of 0.3681 indicates a likelihood that the individual will be responsive to a DNA-damage therapeutic agent.

A cancer is "responsive" to a therapeutic agent if its rate of growth is inhibited as a result of contact with the therapeutic agent, compared to its growth in the absence of contact with the therapeutic agent. Growth of a cancer can be measured in a variety of ways, for instance, the size of a tumor or the expression of tumor markers appropriate for that tumor type may be measured.

A cancer is "non-responsive" to a therapeutic agent if its rate of growth is not inhibited, or inhibited to a very low degree, as a result of contact with the therapeutic agent when compared to its growth in the absence of contact with the therapeutic agent. As stated above, growth of a cancer can be measured in a variety of ways, for instance, the size of a tumor or the expression of tumor markers appropriate for that tumor type may be measured. The quality of being non-responsive to a therapeutic agent is a highly variable one, with different cancers exhibiting different levels of "non-responsiveness" to a given therapeutic agent, under different conditions. Still further, measures of non-responsiveness can be assessed using additional criteria beyond growth size of a tumor, including patient quality of life, degree of metastases, etc.

An application of this test will predict end points including, but not limited to, overall survival, progression free survival, radiological response, as defined by RECIST, complete response, partial response, stable disease and serological markers such as, but not limited to, PSA, CEA, CA125, CA15-3 and CA19-9.

Alternatively, non-array based methods for detection, quantification and qualification of RNA, DNA or protein within a sample of one or more nucleic acids or their biological derivatives such as encoded proteins may be employed, including quantitative PCR (QPCR), enzyme-linked immunosorbent assay (ELISA) or immunohistochemistry (IHC) and the like.

After obtaining an expression profile from a sample being assayed, the expression profile is compared with a reference or control profile to make a diagnosis regarding the therapy responsive phenotype of the cell or tissue, and therefore host, from which the sample was obtained. The terms "reference" and "control" as used herein in relation to an expression profile mean a standardized pattern of gene or gene product expression or levels of expression of certain biomarkers to be used to interpret the expression classifier of a given patient and assign a prognostic or predictive class. The reference or control expression profile may be a profile that is obtained from a sample known to have the desired phenotype, e.g., responsive phenotype, and therefore may be a positive reference or control profile. In addition, the reference profile may be from a sample known to not have the desired phenotype, and therefore be a negative reference profile.

If quantitative PCR is employed as the method of quantitating the levels of one or more nucleic acids, this method quantifies the PCR product accumulation through measurement of fluorescence released by a dual-labeled fluorogenic probe (i.e. TaqMan® probe).

In certain embodiments, the obtained expression profile is compared to a single reference profile to obtain information regarding the phenotype of the sample being assayed. In yet other embodiments, the obtained expression profile is compared to two or more different reference profiles to obtain more in depth information regarding the phenotype of the assayed sample. For example, the obtained expression profile may be compared to a positive and negative reference profile to obtain confirmed information regarding whether the sample has the phenotype of interest.

The comparison of the obtained expression profile and the one or more reference profiles may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above.

The comparison step results in information regarding how similar or dissimilar the obtained expression profile is to the one or more reference profiles, which similarity information is employed to determine the phenotype of the sample being assayed. For example, similarity with a positive control indicates that the assayed sample has a responsive phenotype similar to the responsive reference sample. Likewise, similarity with a negative control indicates that the assayed sample has a non-responsive phenotype to the non-responsive reference sample.

The level of expression of a biomarker can be further compared to different reference expression levels. For example, a reference expression level can be a predetermined standard reference level of expression in order to evaluate if expression of a biomarker or biomarker set is informative and make an assessment for determining whether the patient is responsive or non-responsive. Additionally, determining the level of expression of a biomarker can be compared to an internal reference marker level of expression which is measured at the same time as the biomarker in order to make an assessment for determining whether the patient is responsive or non-responsive. For example, expression of a distinct marker panel which is not comprised of biomarkers of the invention, but which is known to demonstrate a constant expression level can be assessed as an internal reference marker level, and the level of the biomarker expression is determined as compared to the reference. In an alternative example, expression of the selected biomarkers in a tissue sample which is a non-tumor sample can be assessed as an internal reference marker level. The level of expression of a biomarker may be determined as having increased expression in certain aspects. The level of expression of a biomarker may be determined as having decreased expression in other aspects. The level of expression may be determined as no informative change in expression as compared to a reference level. In still other aspects, the level of expression is determined against a pre-determined standard expression level as determined by the methods provided herein.

The invention is also related to guiding conventional treatment of patients. Patients in which the diagnostics test reveals that they are responders to the drugs, of the classes that directly or indirectly affect DNA damage and/or DNA damage repair, can be administered with that therapy and both patient and oncologist can be confident that the patient will benefit. Patients that are designated non-responders by the diagnostic test can be identified for alternative therapies which are more likely to offer benefit to them.

The invention further relates to selecting patients for clinical trials where novel drugs of the classes that directly or indirectly affect DNA damage and/or DNA damage repair. Enrichment of trial populations with potential responders will facilitate a more thorough evaluation of that drug under relevant criteria.

The invention still further relates to methods of diagnosing patients as having or being susceptible to developing a cancer associated with a DNA damage response deficiency (DDRD). DDRD is defined herein as any condition wherein a cell or cells of the patient have a reduced ability to repair DNA damage, which reduced ability is a causative factor in the development or growth of a tumor. The DDRD diagnosis may be associated with a mutation in the Fanconi anemia/BRCA pathway. The DDRD diagnosis may also be associated with breast cancer or ovarian cancer. These methods of diagnosis comprise the steps of obtaining a test sample from the individual; measuring expression levels of one or more biomarkers in the test sample, wherein the one or more biomarkers are selected from the group consisting of CXCL10, MX1, IDO1, IF144L, CD2, GBP5, PRAME, ITGAL, LRP4, and APOL3; deriving a test score that captures the expression levels; providing a threshold score comprising information correlating the test score and a diagnosis of the cancer; and comparing the test score to the threshold score; wherein the individual is determined to have the cancer or is susceptible to developing the cancer when the test score exceeds the threshold score. One of ordinary skill in the art can determine an appropriate threshold score, and appropriate biomarker weightings, using the teachings provided herein including the teachings of Example 1.

In other embodiments, the methods of diagnosing patients as having or being susceptible to developing a cancer associated with DDRD comprise measuring expression levels of one or more biomarkers in the test sample, wherein the one or more biomarkers are selected from the group consisting of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR211P, EGFR, NAT1, LATS2, CYP2B6, PTPRC, PPP1R1A, and AL137218.1. Tables 2A and 2B provide exemplary gene signatures (or gene classifiers) wherein the biomarkers consist of 40 or 44 of the gene products listed therein, respectively, and wherein a threshold score is derived from the individual gene product weightings listed therein. In one of these embodiments wherein the biomarkers consist of the 44 gene products listed in Table 2B, and the biomarkers are associated with the weightings provided in Table 2B, a test score that exceeds a threshold score of 0.3681 indicates a diagnosis of cancer or of being susceptible to developing a cancer.

The following examples are offered by way of illustration and not by way of limitation.

EXAMPLES

Example 1

Tissue Processing, Hierarchical Clustering, Subtype Identification and Classifier Development Tumor Material The genes determined to be useful in the present methods (Table 2) were identified from gene expression analysis of a cohort of 107 macrodissected breast tumor FFPE tissue samples sourced from the Mayo Clinic Rochester. Ethical approval for this study was obtained from the Institutional Review Board and the Office of Research Ethics Northern Ireland.

This cohort of samples can be further described as follows:
- 47 samples were wild-type for BRCA1 and BRCA2 i.e. expressed biologically functional BRCA1 and BRCA2 proteins. These samples shall henceforth be referred to as sporadic controls.
- 31 samples were BRCA1 mutant i.e. did not express biologically functional BRCA1 protein.
- 29 samples were BRCA2 mutant i.e. did not express biologically functional BRCA2 protein.

Gene Expression Profiling

Total RNA was extracted from the macrodissected FFPE tumor samples using the Roche High Pure RNA Paraffin Kit (Roche Diagnostics GmbH, Mannheim, Germany). Total RNA was amplified using the NuGEN WT-Ovation™ FFPE System (NuGEN Technologies Inc., San Carlos, Calif., USA). The amplified single-stranded cDNA was then fragmented and biotin labeled using the FL-Ovation™ cDNA Biotin Module V2 (NuGEN Technologies Inc.). It was then hybridized to the Almac Breast Cancer DSA™. The Almac's Breast Cancer DSA™ research tool has been optimised for analysis of FFPE tissue samples, enabling the use of valuable archived tissue banks. The Almac Breast Cancer DSA™ research tool is an innovative microarray platform that represents the transcriptome in both normal and cancerous breast tissues. Consequently, the Breast Cancer DSA™ provides a comprehensive representation of the transcriptome within the breast disease and tissue setting, not available using generic microarray platforms. Arrays were scanned using the Affymentrix Genechip® Scanner 7G (Affymetrix Inc., Santa Clara, Calif.).

Data Preparation

Quality Control (QC) of profiled samples was carried out using MASS pre-processing algorithm. Different technical aspects were addressed: average noise and background homogeneity, percentage of present call (array quality), signal quality, RNA quality and hybridization quality. Distributions and Median Absolute Deviation of corresponding parameters were analyzed and used to identify possible outliers.

Almac's Ovarian Cancer DSA™ contains probes that primarily target the area within 300 nucleotides from the 3' end of a polynucleotide. Therefore standard Affymetrix RNA quality measures were adapted—for housekeeping genes intensities of 3' end probesets along with ratios of 3' end probeset intensity to the average background intensity were used in addition to usual 3'/5' ratios. Hybridization controls were checked to ensure that their intensities and present calls conform to the requirements specified by Affymetrix.

Tumor samples from the BRCA1/2 mutant and sporadic control training set were split into 2 datasets based on the transcript levels of ESR1 (Estrogen receptor 1). mRNA expression level $E_{.avg}$ for each sample was determined by the average expression of all ESR1 probe sets (BRAD.15436_s_at, BRAD.19080_s_at, BREM.1048_at, BRIH.10647C1n2_at, BRIH.5650C1n2_at, BRPD.10690C1n5_at, BRRS.81_at and BRRS.81-22_at). The mRNA median expression ($E_{.med.all}$) was calculated for all samples. Samples were considered ER positive when $E_{.avg} - E_{.med.all} > 0.5$ and ER negative when $E_{.avg} - E_{.med.all} < 0.5$.

Pre-processing was performed in expression console v1.1 with Robust Multi-array Analysis (RMA) (Irizarry et al., 2003) resulting in 2 data matrices of ER positive and ER negative samples composed of 56 and 51 samples respectively. An additional transformation was performed to remove the variance associated with array quality as described by Alter (Alter et al., 2000).

Feature Selection

A combined background & variance filter was applied to each data matrix to identify the most variable probesets. The background filter is based on the selection of probe sets with expression E and expression variance $var_E$ above the thresholds defined by background standard deviation σBg (from the Expression Console software) and quantile of the standard normal distribution $z_a$ at a specified significance a probesets were kept if:

$$E > \log_2(\square z_a \sigma_{Bg} \square); \square \log_2(\square \text{var}_E) > 2[\log_2(\sigma_{Bg}) - E - \log_2(\log(2))]$$

where the significance threshold was $a=6.3 \cdot 10^{-5}$, see Table 1 for the list of selected probesets and their gene annotations.

Hierarchical Clustering Analysis

Figure 1B:
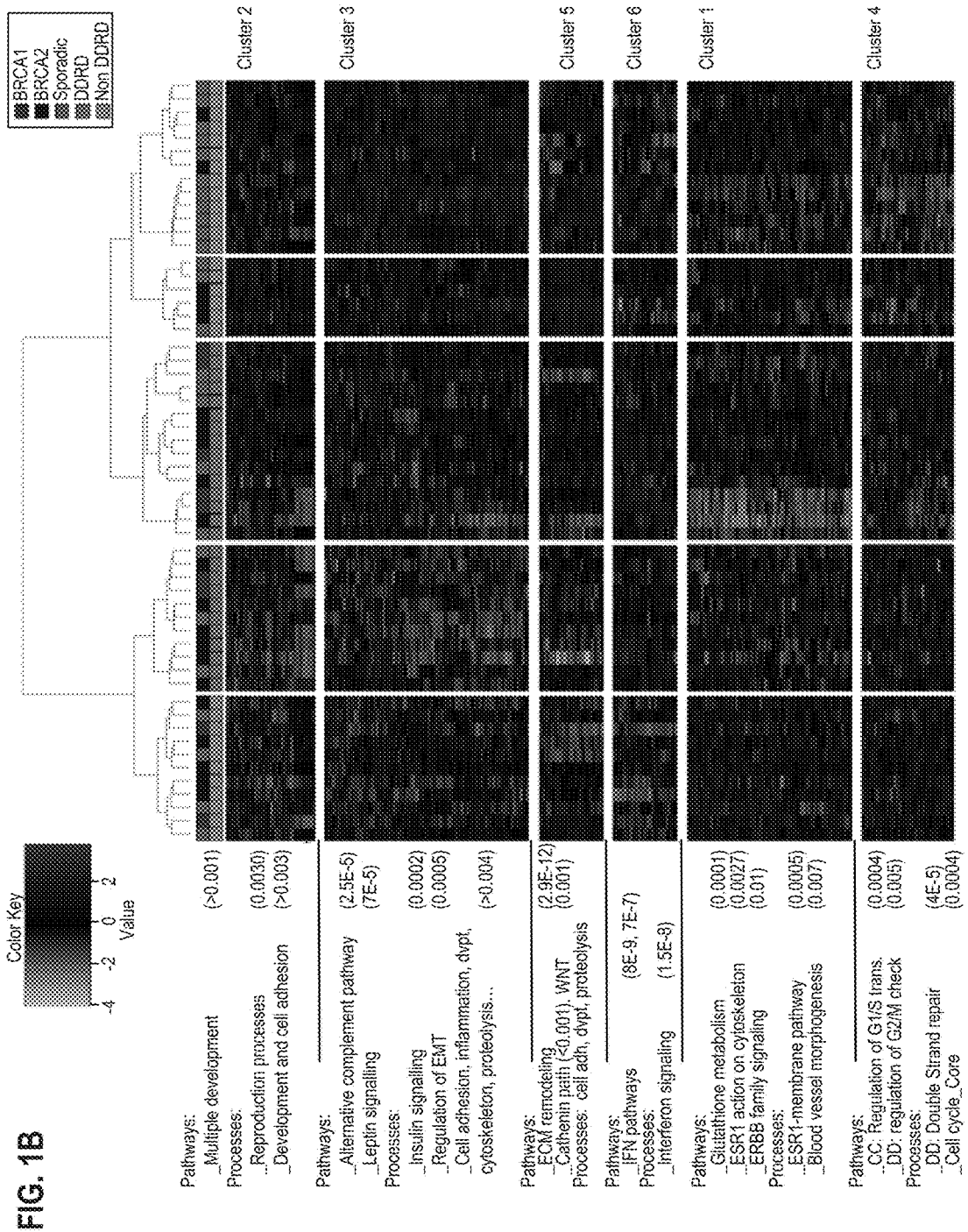

Hierarchical clustering techniques were applied to microarray data from 199 epithelial serous ovarian tumors analysed using the Ovarian Cancer DSA™ (disease specific array) platform (FIG. 1). Raw expression data was preprocessed using the standard Robust Multichip Algorithm (RMA) procedure. Non-biological systematic variance in the data set was identified and removed. Those probesets whose expression levels varied significantly from tumor to tumor were identified. These probesets formed the intrinsic list.

2-D cluster analysis (tumor, probeset) was performed to establish tumor relationships based on the intrinsic list. Hierarchical agglomerative clustering was applied (Pearson correlation distance and Ward's linkage). Optimal partition number was selected using the GAP index (Tibshirani et al., 2002, J. R. Stat. Soc., 63:411-423). All probesets available in the subclusters were mapped to genes names.

Functional Analysis of Gene Clusters

To establish the functional significance of the probeset clusters, probesets were mapped to genes (Entrez gene ID) and an enrichment analysis, based on the hypergeometric function (False Discovery Rate applied (Benjamini and Hochberg, 1995, J. R. Stat. Soc. 57:289:300)), was performed. Over-representation of biological processes and pathways were analysed for each gene group generated by the hierarchical clustering for both ER-positive and ER-negative samples using Metacore™ single experiment analysis workflow from GeneGo®. Antisense probesets were excluded from the analysis. Hypergeometric p-values were assessed for each enriched functional entity class. Functional entity classes with the highest p-values were selected as representative of the group and a general functional category representing these functional entities was assigned to the gene clusters based on significance of representation (i.e. p-value).

Genes in clusters enriched for the IFN/DD general functional terms were grouped into a DNA-damage response-deficiency (DDRD) sample group and used for the classifier generation. The sample clusters from ER-positive and ER-negative datasets represented by the IFN/DD general functional terms were selected for classification and labelled as DDRD. Those not represented by these functional terms were labelled as non-DDRD.

Classifier Development at a Probeset Level

Following the identification of a class of tumors that form the DDRD subgroup, computational classification of these tumors vs. all the others in the tumor cohort (non-DDRD) was performed, with reference to the functional DDRD gene list (Table 1), to identify a refined gene classification model that classifies the DDRD subgroup. This was evaluated using all combinations of the following options (a total of 18):

Three sample sets
  Combined sample set of ER-negative and ER-positive samples (combined sample set)
  ER-negative samples alone
  ER-positive samples alone Two feature sets
  Full feature list with 75% variance/intensity filtering and forced inclusion of the DDRD list. Here 75% of the probesets with the lowest combined variance and intensity were removed, based on the average rank of both. When used, the term "VarInt" refers to this option.
  DDRD list only. When used, the term "List only" refers to this option.

Three classification algorithms
  PLS (Partial Least Squares) (de Jong, 1993)
  SDA (Shrinkage Discriminate Analysis)(Ahdesmaki and Strimmer, 2010)
  DSDA (Diagonal SDA)(Ahdesmaki and Strimmer, 2010)

The AUC was used to assess the performance of the different models. Iterative Feature Elimination (IFE) was implemented throughout the development of each model, where the maximum AUC was the main criteria in selecting an optimal number of features over cross validation. In cases where there was no visible AUC difference across features, the minimum feature length was selected.

Classifier Development at a Gene Level

To facilitate validation of the classifier across multiple array platforms, the selected probeset classifier was regenerated at the gene level. A redevelopment of the probeset classifier at a gene level required two separate steps:
  1. The expression intensities of the unique genes in the probeset classifier were estimated from the median of the probesets mapping to each gene, excluding anti-sense probesets.
  2. The classifier parameters used for classification were re-estimated A threshold was chosen based on the maximum sensitivity and specificity over all cross validation predictions.

Similarly the gene level defined expression intensities for the 10 top genes (or any number of features present in current 44 gene signature) could be used to re-develop the classifier based on only these 10 genes (or any number of features present in current 44 gene signature) by re-estimating classification parameters in cross-validation in the training data set as well as to re-establish the threshold by assessing and maximising the sensitivity and specificity obtained from all cross-validation predictions. The methodology would be similar to the method used when working from a larger feature set (described above) except there will be no feature selection involved: the features will remain the same but will be assigned new weights.

Calculating Classifier Scores for Validation Data Sets

Public Datasets

The datasets used for this analysis are namely: FAC1 [GEO accession number GSE20271, (Tabchy et al., 2010)], FAC2 [GEO accession number GSE22093, (Iwamoto et al., 2011)], FEC [GEO accession number GSE6861, (Bonnefoi et al., 2007)], T/FAC1 (Hess et al., 2006)], T/FAC2 [GEO accession number GSE16716, (Lee et al., 2010)] and T/FAC3 [GEO accession number GSE20271, (Tabchy et al., 2010)]. It must be noted that there is an overlap in 31 samples between the FAC1 and FAC2 datasets. These samples were removed from the FAC2 dataset and as such were only included once in the combined analysis of the FAC1, FAC2 and FEC datasets. In addition, sample GSM508092 was removed from FAC1 as it is a metastatic lymph node sample.

All datasets were pre-processed using RMA (Irizarry et al., 2003). For each validation set, the probesets that map to the classifier genes were determined, excluding anti-sense probesets (if applicable). Annotation for Affymetrix X3P and U133A arrays are available from the Affymetrix website. The median intensity over all probesets mapping to each gene in the classifier was calculated, resulting in a gene intensity matrix. The classifier was then applied to this data matrix to produce a classifier score/prediction for each sample.

Calculating Performance Metrics

To calculate NPV and PPV, the prevalence of each end point (BRCA status/Response) was estimated using the proportions of each class in the corresponding data set.

Univariate and Multivariate analysis

Univariate and multivariate analysis was carried out to assess respectively the association between the DDRD classifier and response, and to determine if the association, if any, was independent to known clinical predictors. The p-values presented Table 4, for univariate analysis were calculated using logistic regression in MATLAB. For the multivariate analysis we used step-wise logistic regression (Dupont, 2009), where the p-values represent the log-likelihood of the variable. The log-likelihood is a measure of the importance of the variable's fit to the model, thus highlighting it's independence as a predictor relative to the other predictors. In both univariate and multivariate analysis, a p-value <0.05 was used as the criterion for significance. Furthermore, samples with unknown clinical factors were excluded in this assessment.

Results

Selection of Samples for Classifier Generation

The objective of this study was to characterize at a transcriptomic level a set of genes that would be capable of determining responsiveness or resistance of a pathogenic cell to DNA-damage therapeutic agents. With this in mind, those samples within the Almac breast cancer dataset that best represented this biology were to be selected and compared to the remaining samples for classifier generation (see next section). It was decided that the samples from sample cluster two within the ER−ve sample set were the most relevant samples for this selection as these showed the greatest proportion of BRCA mutant samples (64%) and they exhibited the most dominant biology (IFN/immune response). From within the ER+ve sample set, the samples from sample cluster two and three were selected as these sample clusters had 73% and 67% BRCA mutant tumors respectively. In addition, the most dominant biology within these clusters was related to cell cycle, DNA damage response and IFN/immune response. Immune signaling and cell-cycle pathways have been reported to be modulated in response to DNA-damage (Jackson, S. P., and Bartek, J., Nature 461, 1071-1078 (2009); Rodier, F., et al., Nat Cell Biol 11, 973-979 (2009); Xu, Y., Nat Rev Immunol 6, 261-270 (2006), and these subgroups were combined to form a putative DDRD subgroup. Those samples within cluster two of the ER−ve sample set (described below) and clusters two and three of the ER+ve sample set (described below) were class labelled DDRD (DNA damage response deficient) (see FIG. 1A) whilst the samples within sample clusters one and three of the ER−ve sample set and sample clusters one, four, five and six of the ER+ve sample set were class labeled non-DDRD (see FIG. 1B).

ER−ve sample set: Within the ER−ve sample set, the hierarchical cluster analysis defined three sample clusters and six probeset cluster groups. Probeset cluster three was identified as the most significant biology within the ER−ve sample set and was enriched for interferon and immune response signaling.

ER+ve sample set: Within the ER+ve sample set, the hierarchical analysis defined six sample groups and six probeset cluster groups. Probeset cluster five was identified as the most significant biology within the ER+ve sample set and was enriched for extracellular matrix remodeling. The next most significant probeset cluster within the ER+ve sample set is probeset cluster six and again was enriched for interferon and immune response signaling.

Development and Validation of the DDRD Classifier Model

Following the identification of a class of tumors, that form the DDRD subgroup, computational classification of these tumors vs. all others in the tumor cohort with reference to the functional DDRD (IFN/DNA damage) gene list was performed to identify a refined gene classification model, which classifies the DDRD subgroup.

The classification pipeline was used to derive a model using the set of combined ER−ve and ER+ve breast cancer samples. The classification pipeline has been developed in accordance with commonly accepted good practice [MAQC Consortium, Nat Biotechnol 2010]. The process will, in parallel: 1) derive gene classification models from empirical data; and 2) assess the classification performance of the models, both under cross-validation. The performance and success of the classifier generation depends on a number of parameters that can be varied, for instance the choice of classification method or probe set filtering. Taking this into account, two feature sets were evaluated (i) the full feature list with 75% variance/intensity filtering (with forced inclusion of the DDRD (IFN/DNA damage) list, Table 1) and (ii) the DDRD (IFN/DNA damage) list only; and three classification algorithms were evaluated, namely PLS (Partial Least Squares); SDA (Shrinkage Discriminate Analysis) and DSDA (Diagonal SDA). Iterative Feature Elimination (IFE) was used throughout model development, which is an iterative procedure removing a fraction of the worst-ranked features at each iteration; stopping when only a minimum number of features remain. The Area under the Receiver Operating Characteristics Curve (AUC-ROC), denoted AUC, was used to assess the classification performance, as this measure is independent of cut-off between groups and prevalence rates in the data. It is also one of the recognized measurements of choice for classification performance. As such, the best number of features for each model was chosen based on the average AUC under cross-validation.

A cross comparison of the models was made, by first selecting the best number of features for each model based on the highest average AUC, and then using box-plots to visualize the performance for each model. This is demonstrated in FIG. 2. From left to right, the first three plots represent the PLS, SDA and DSDA classifiers respectively that were developed using an initial filtering of probe sets to remove 75% with the lowest average variance and intensity (forcing the inclusion of the gene list). The next three plots respectively represent the PLS, SDA and DSDA classifiers developed using the DDRD (IFN/DNA damage) list only.

Figure 2A:
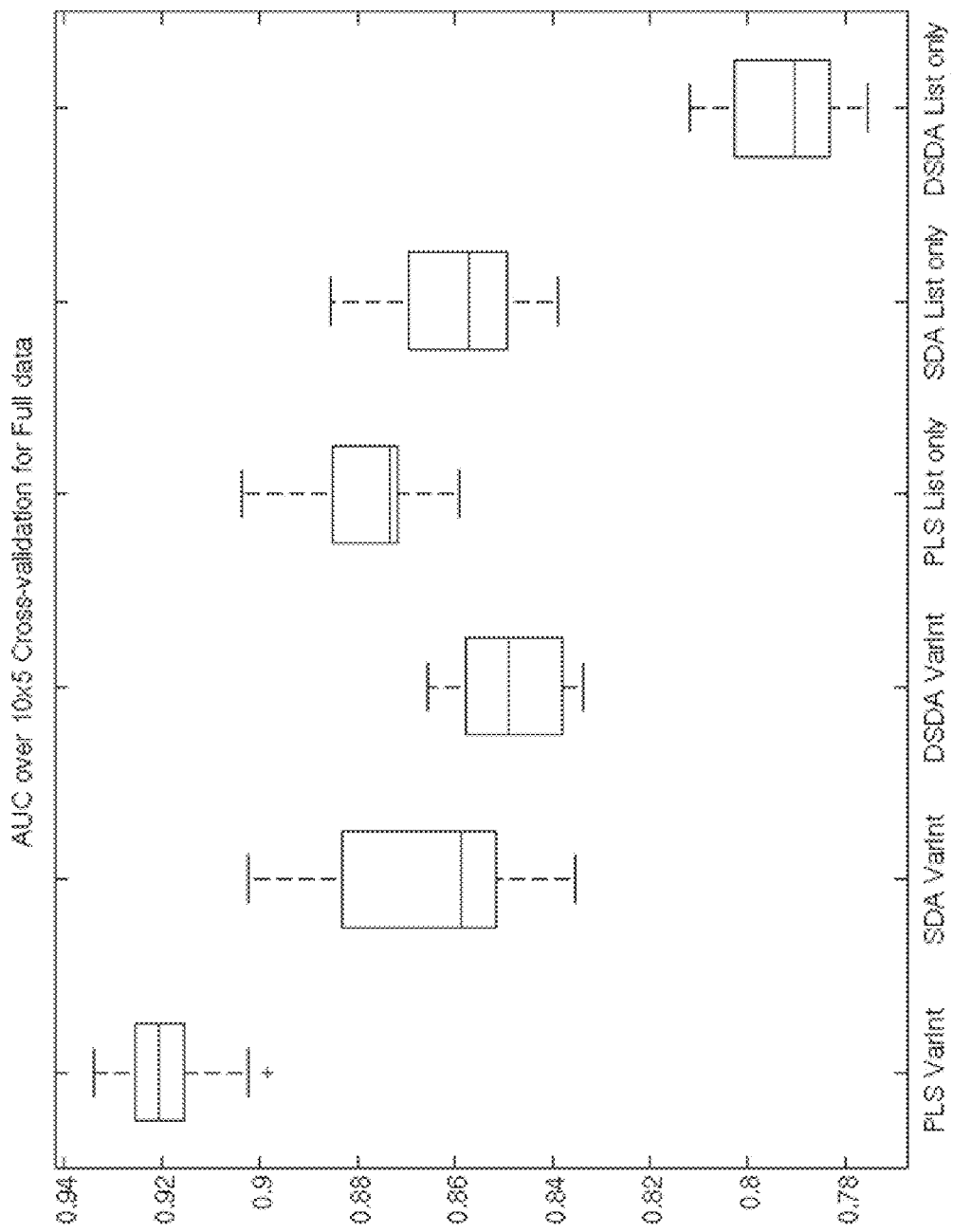
Figure 2C:
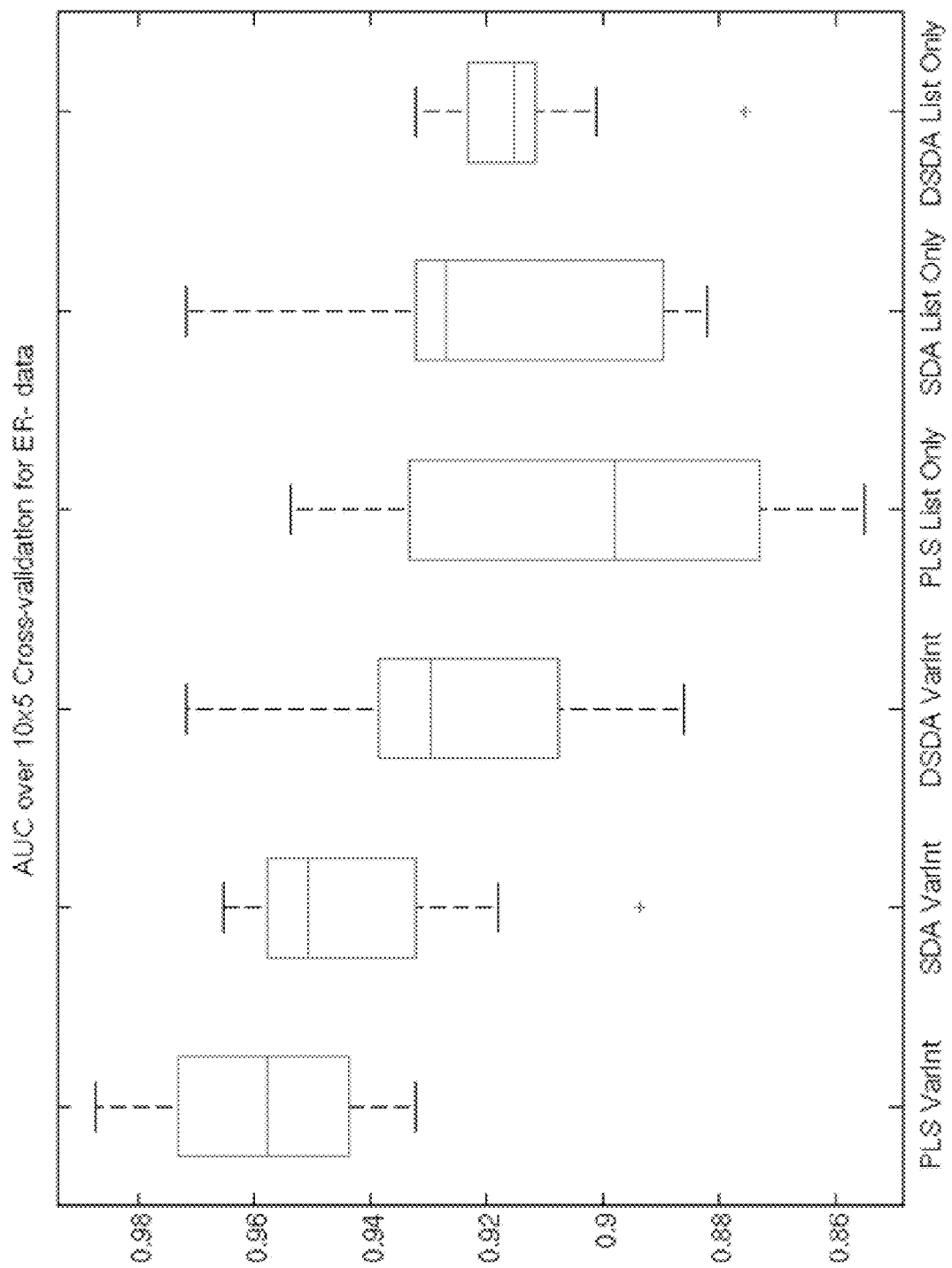
Figure 2D:
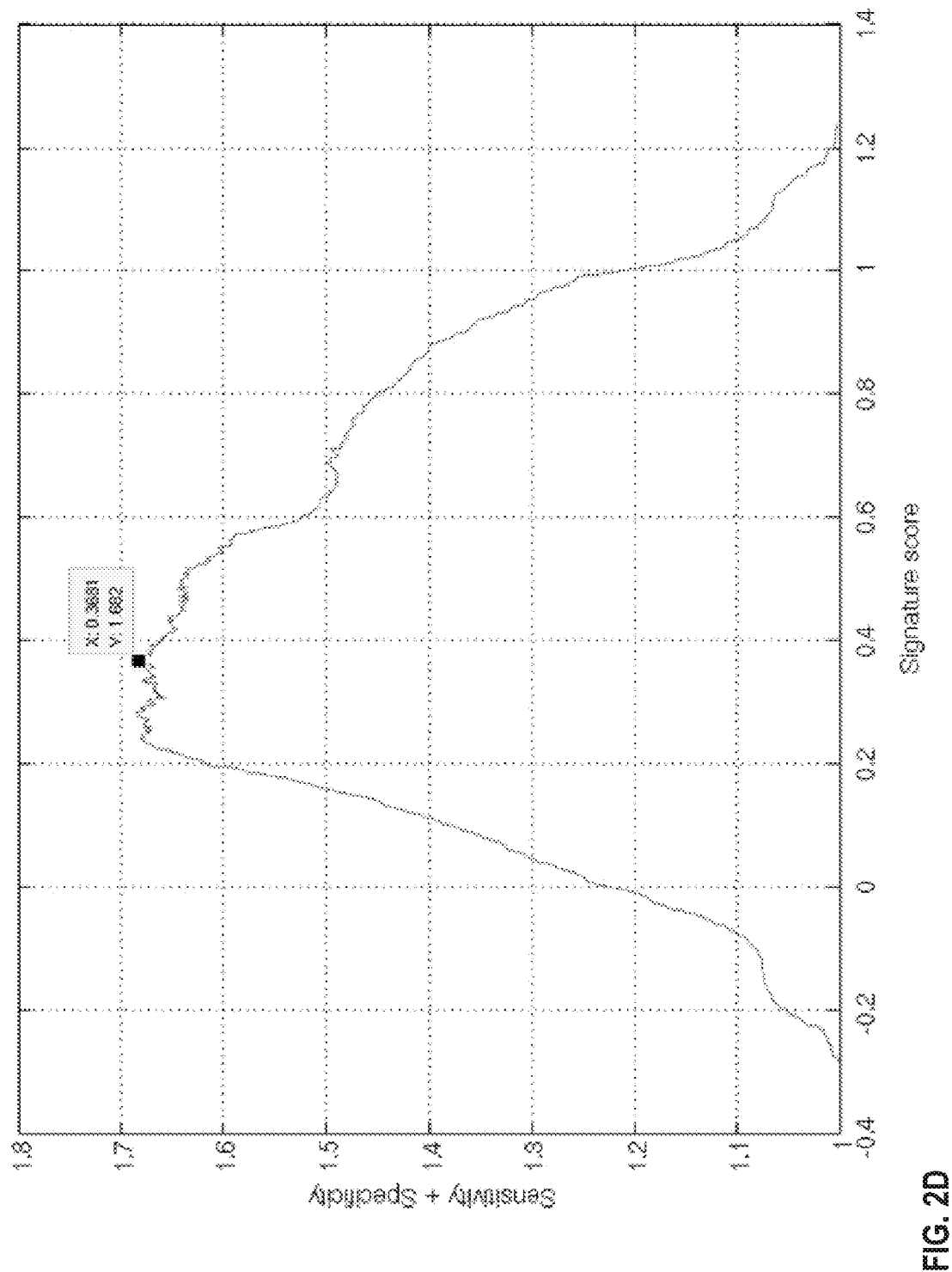

From FIG. 2, it is clear that the 'PLS VarInt' classification model, comprising 53 probe sets, is the highest performing model, with a significantly higher AUC than the majority of the other 5 models. This model was then taken forward to the next phase for validation on independent external data sets, to assess the ability of the DDRD classification scores to stratify patients with respect to response and prognosis.

A non-orthodox approach to validating the classification model was taken, due to the fact that the validation data sets where either public or internal data with different array platforms. Commonly used approaches are not designed to be applicable to alternative array platforms, and as such a phased approach for classification model development and independent validation was followed:
1. Phase I—Model generation at the probe set level, selecting the best model under cross validation for classifying the DDRD subgroup (described previously)
2. Phase II—Transformation of the probe set level classification model to a gene level classification model
3. Phase III—Validation of re-developed gene classification model using external data sets Having selected a candidate model to progress to the validation stage, this model needed to be re-built at the gene level (Phase II). This involved mapping the probe sets in the classification model to the gene level and recalculating the weights for each gene. The 53 probe sets in the selected model mapped to 40 genes listed in Table 2A and subsequently mapped to 44 genes listed in Table 2B when the accuracy of the annotation pipeline was improved through further analysis.

In the re-development of the gene classification model, to ensure that all information relating to the gene is used, the median intensity of all probe sets associated with each gene (Table 2C) is used as the gene expression value. This was calculated for all samples, resulting in a gene expression data matrix, as opposed to a probe set expression data matrix that was used in Phase I for model development and selection. To stabilize the intensities across different batches, the median of all probe sets for each sample was subtracted from the corresponding intensity of each gene for that sample.

New weights were calculated for each gene using PLS regression, resulting in the final gene classifier models (40-gene and 44-gene classifier models) that may be used for validation on external data sets from different array platforms (Phase III).

In Phase III, the validation of the classifier using data sets that may be from other array platforms, the following steps were taken:
1. The probe sets that map to the genes in the classifier are determined, excluding antisense probe sets (if applicable)
2. The median intensity over all probe sets relating to each gene in the classifier is calculated resulting in a reduced gene intensity matrix
   a. If no probe sets exist for the gene on the particular array platform, the observed average from the training data will be used as a replacement
3. The median value of all probe sets for each sample is calculated and subtracted from the reduced gene intensity matrix
4. The value for each gene is multiplied by the "weight" of that gene in the signature.
5. The values obtained in point 4 for each of the genes in the signature are added together to produce a signature score for that sample.
6. The classifier produces a score for each sample, which can then be used to stratify patients from say, more likely to respond to less likely to respond.

Example 2

In Silico Validation of the 44-Gene DDRD Classifier Model

The performance of the 44-gene DDRD classifier model was validated by the Area Under the ROC (Receiver Operator Characteristic) Curve (AUC) within the original Almac breast dataset and three independent datasets. The AUC is a statistic calculated on the observed disease scale and is a measure of the efficacy of prediction of a phenotype using a classifier model (Wray et. al., PLoS Genetics Vol 6, 1-9). An AUC of 0.5 is typical of a random classifier, and an AUC of 1.0 would represent perfect separation of classes. Therefore, in order to determine if the 44-gene DDRD classifier model is capable of predicting response to, and selecting patients for, standard breast and ovarian cancer therapeutic drug classes, including DNA damage causing agents and DNA repair targeted therapies, the hypothesis is that the AUCs following application within these datasets should be above 0.5 with the lowest confidence interval also above 0.5.

Assessment of 44-Gene Classifier Model's Ability to Separate BRCA Mutant from Sporadic Tumors The classifier scores for predicting DDRD status were utilized to assess the ability of the model to separate BRCA mutant samples from sporadic samples. This analysis was performed to assess the relationships between the classifier model and BRCA mutation status. BRCA mutant tumors display a high degree of genomic instability due to a deficiency in DNA damage response by virtue of the loss of functional BRCA1/2. As such, the hypothesis is that the DDRD classifier models should be able to separate BRCA mutant samples from BRCA wildtype sporadic samples.

Figure 3:
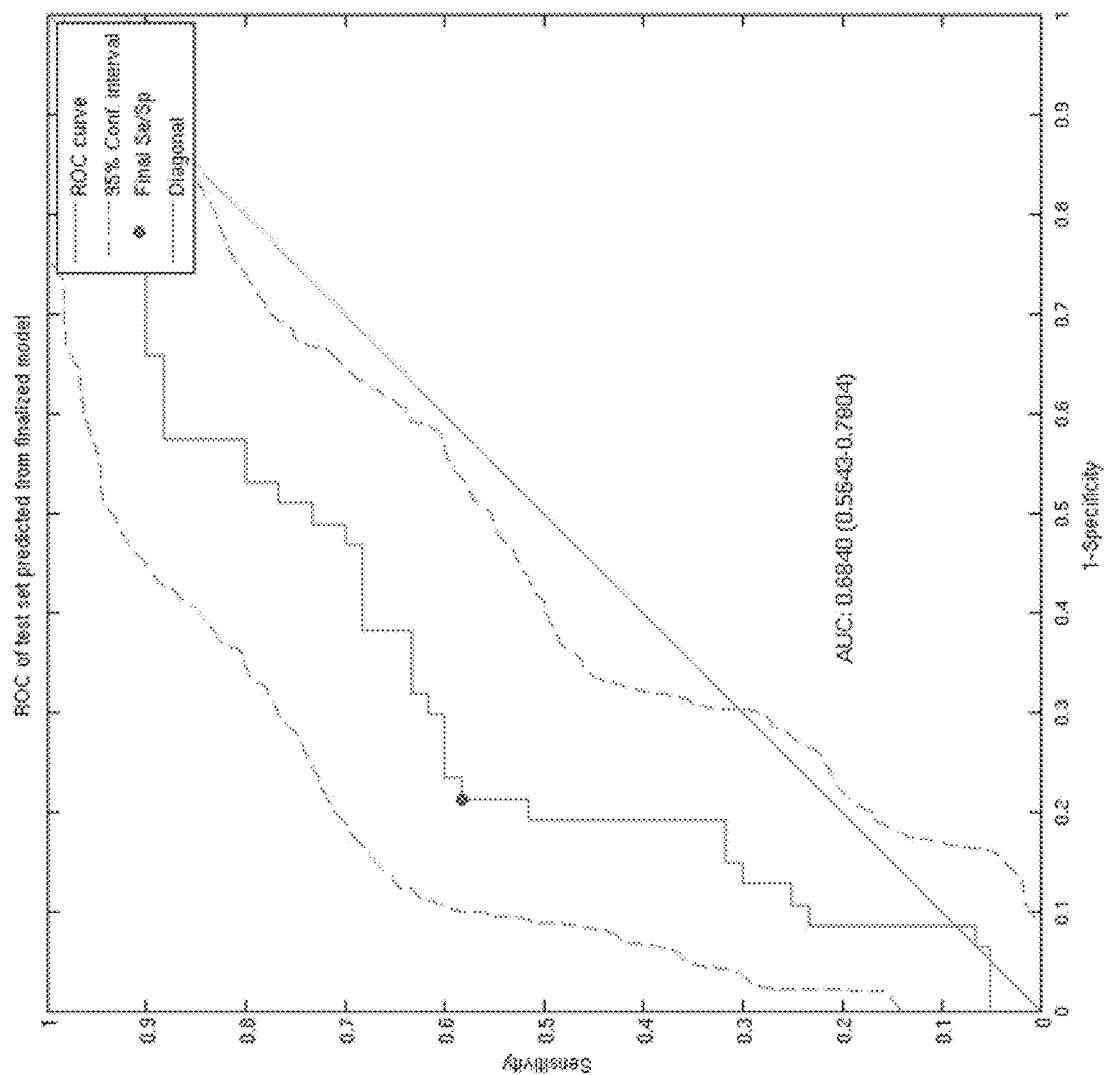
FIG. 3 provides a diagram of a ROC curve of the classification performance for predicting BRCA status using the 44-gene classifier model, estimated by cross validation. The AUC is ~0.68 following application the classifier model. The 95% confidence limits have been estimated from bootstrap with 1000 iterations.

FIG. 3 shows that the 44-gene classifier models separate the BRCA mutants from the sporadic samples with an AUC of ~0.68, where the lower confidence interval is ~0.56 for both models (Table 3A); showing that the performance is significantly better than a random classifier. As such, this analysis confirms that the 44-gene DDRD classifier model is capable of identifying samples with high genomic instability due to an inability to repair DNA damage.

Application of Classifier Model to Independent Microarray Clinical Datasets

Independent Breast Microarray Clinical Datasets
(1) Assessment of the 44-Gene DDRD Classifier Model's Predictive Power to DNA-Damaging Chemotherapy To assess the ability of the 44-gene DDRD classifier model to predict response to DNA-damaging chemotherapeutics, it was applied to data combined from three publicly available datasets. In each study, breast cancer patients were treated with neoadjuvant 5-fluorouracil, anthracycline, and cyclophosphamide-based regimens, drugs that directly damage DNA. The first (Tabchy et al., 2010) and second (Iwamoto et al., 2011) datasets had response data for 87 and 50 ER-positive and ER-negative primary breast tumor samples respectively following neoadjuvant treatment with fluorouracil, doxorubicin and cyclophosphamide (FAC). The third dataset (Bonnefoi et al., Lancet Oncol 8, 1071-1078 (2007)) had response data for 66 ER-negative primary breast tumor samples following neoadjuvant 5-fluorouracil, epirubicin and cyclophosphamide (FEC) treatment. Each study used pathological complete response (pCR) or residual disease (RD) as endpoints. As each dataset was relatively small, the data was combined to increase the power of the analysis.

Figure 4:
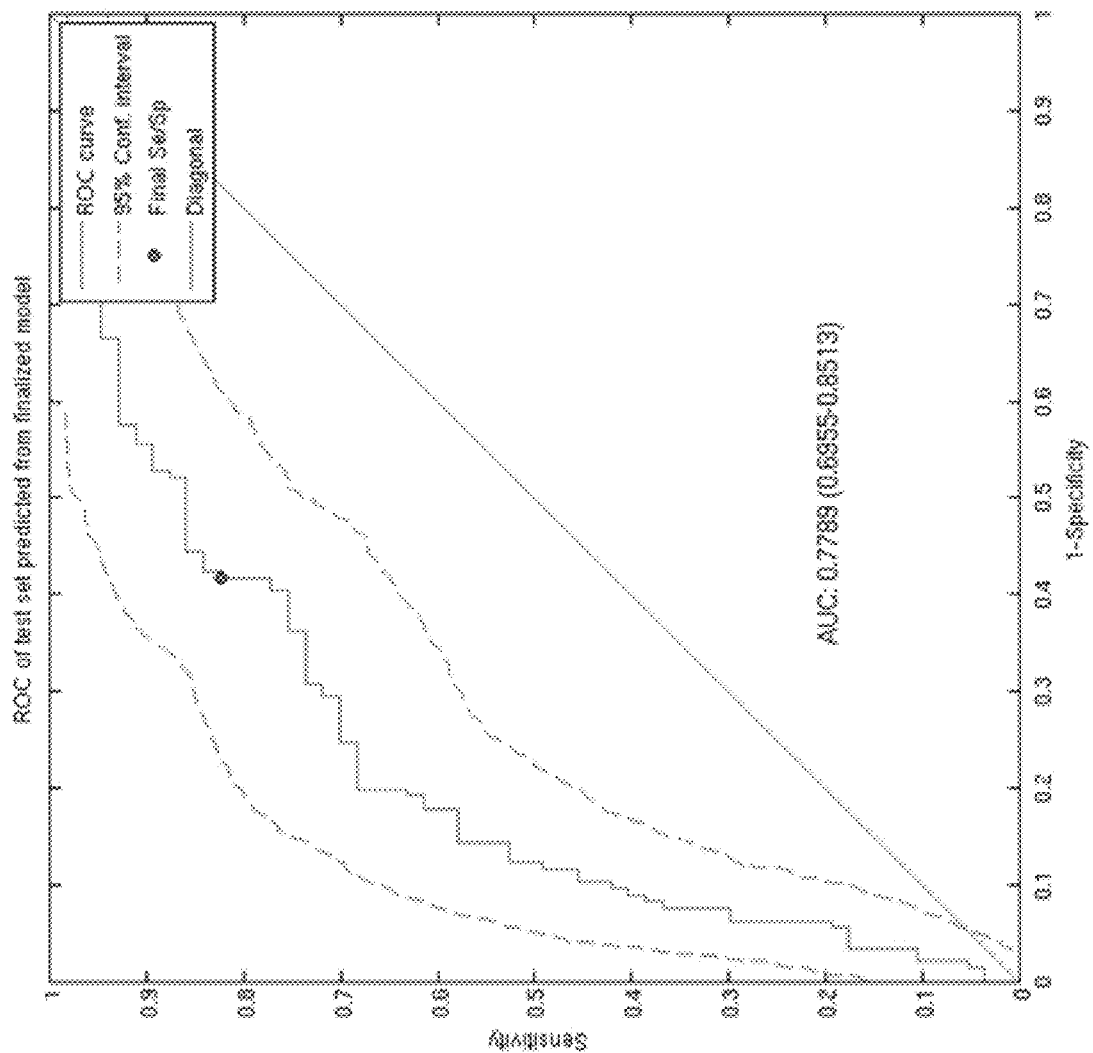
FIG. 4 provides a diagram of a ROC curve of the classification performance of the 44-gene classifier model in a combined analysis of three independent datasets: FEC, FAC1 and FAC2 (Bonnefoi et al., 2007; Iwamoto et al., J Natl Cancer Inst 103, 264-272 (2011); Lee, J. K., et al. Clin Cancer Res 16, 711-718 (2010) for predicting response to anthracycline-based chemotherapy. The AUC is ~0.78 following application of the classifier model. The 95% confidence limits have been estimated from bootstrap with 1000 iterations.

The analysis revealed that that the 44-gene DDRD classifier model was significantly associated with response to anthracycline-based chemotherapy (relative risk (RR)=4.13, CI=1.94-9.87; AUC=0.78, CI=0.70-0.85, P=0.001; Table 3B, FIG. 4). The negative predictive value (NPV) of the classifier was considerably higher than the positive predictive value (PPV) (0.90 versus 0.44, Table 3B), indicating that DDRD-negative tumors were unlikely to respond to DNA-damaging chemotherapy.

Stepwise logistic regression was used to determine the ability of the 44-gene DDRD classifier model to predict response in the combined datasets when adjusting for clinical variables (Table 4). The 44-gene DDRD classifier model was determined to be the most significant clinical variable in univariate analysis. Multivariate analysis confirmed that the 44-gene DDRD classifier model's predictive value was independent of stage, grade and notably ER status.

Negativity for estrogen, progesterone and HER2 receptors has been suggested as a biomarker of abnormal DDR and thus response to DNA-damaging and DNA repair targeted therapies (Foulkes et al., 2010). However, this approach excludes the 20% of BRCA1 and the 40% of BRCA2 mutant tumors that are reported to be ER-positive (Foulkes et al., 2004; Tung et al., 2010). In contrast, by virtue of the analysis approach we adopted, the 44-gene DDRD classifier detects the DDRD subgroup in both ER-positive and ER-negative tumors, as validated by the multivariate analysis of the 44-gene DDRD classifier's predictive value within the combined analysis of FEC and FAC datasets, demonstrating its independence from ER status. Clinically, this is an important aspect of the translational application of the DDRD classifier as it suggests it can be applied to all breast cancer patients, irrespective of ER status, to determine their predicted responsiveness to DNA-damaging therapeutics.

Figure 5:
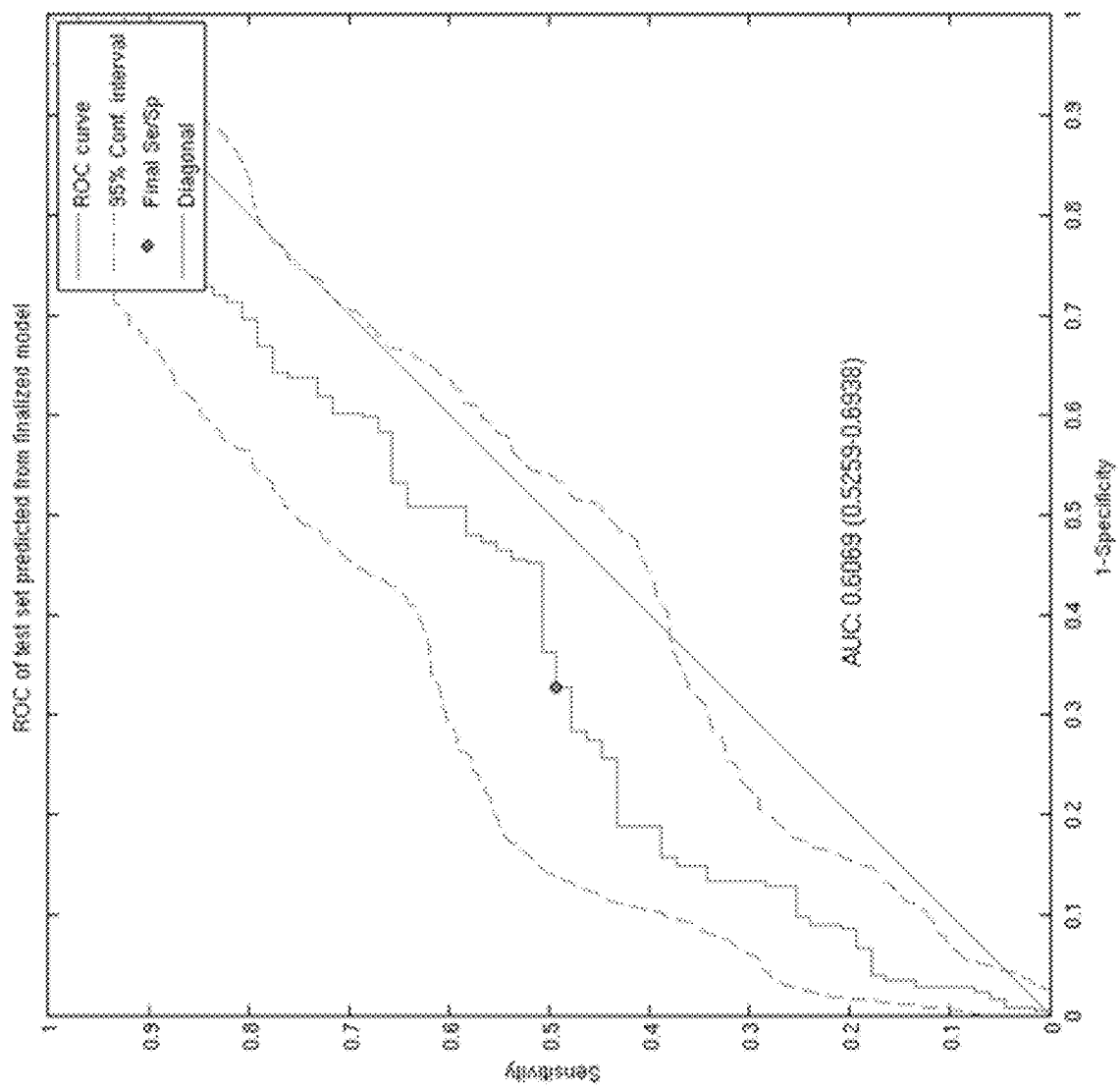
FIG. 5 provides a diagram of a ROC curve of the classification performance of the 44-gene classifier model in a combined analysis of three independent datasets in response in T/FAC treated samples (Hess et al., J Clin Oncol 24, 4236-4244 (2006); Lee et al., 2010; Tabchy, A., et al. Clin Cancer Res 16, 5351-5361 (2010). The AUC is ~0.61 following application of the classifier model respectively. The 95% confidence limits were determined using 1000 bootstrap iterations.

(2) Assessment of 44-Gene DDRD Classifier Model's Predictive Power to Taxane-Containing Chemotherapy Regimens The ability of the 44-gene DDRD classifier model to predict response to chemotherapy regimens that contained non-DNA-damaging agents such as taxanes was assessed. Data was combined from 3 datasets with response data following neoadjuvant treatment with paclitaxel and FAC (T/FAC) for 321 primary breast cancer patients, where response was defined as pCR (Hess et al., 2006; Lee et al., 2010; Tabchy et al., 2010). Whilst the 44-gene DDRD classifier model was both associated with response (AUC=0.61, CI=~0.52-0.69, Table 3B, FIG. 5), this performance was significantly reduced compared to that within the FAC/FEC only treated samples. In addition, multivariate analysis indicated the DDRD classifier was not independent from other clinical parameters (P=0.21) in its ability to predict response to T/FAC (Table 4). This suggests that the subgroup detected by the DDRD classifier is more sensitive to DNA-damaging only regimens rather than regimens also containing anti-microtubule agents.

Independent Ovarian Microarray Clinical Datasets

Figure 6:
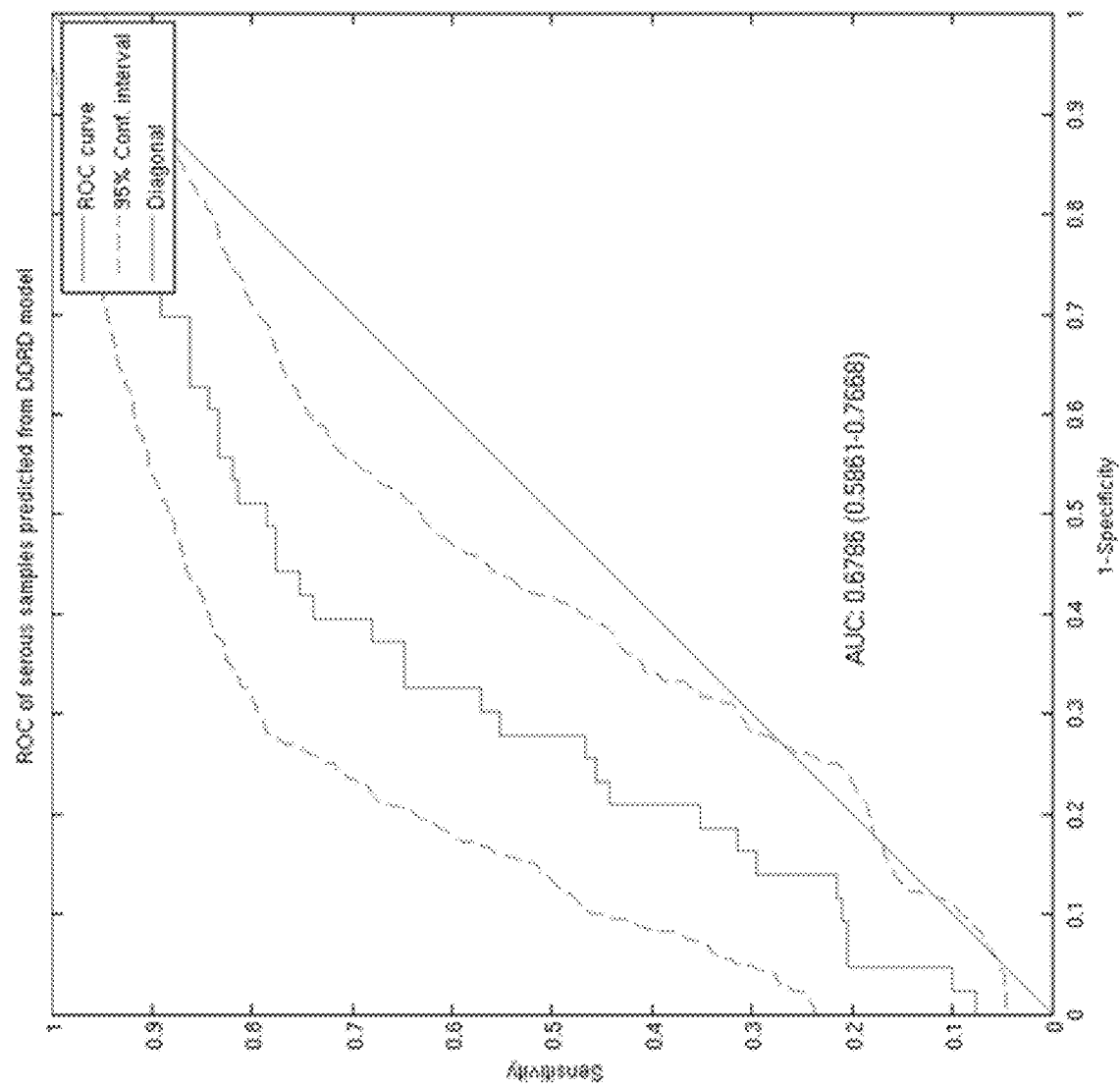
FIG. 6 provides a diagram of a ROC curve of the classification performance of the 44-gene classifier model within 259 serous ovarian cancer samples in response in platinum and taxol treated samples from the in-house Almac Diagnostics ovarian dataset. The AUC is ~0.68 following application of the classifier model. The 95% confidence limits were determined using 1000 bootstrap iterations.

It was decided to explore the performance of the 44-gene DDRD classifier model in another disease area. As such, the performance of the classifier models was assessed within a set of 259 FFPE primary ovarian cancer samples with serous histology. These samples were from patients that received either adjuvant platinum treatment or adjuvant platinum and taxane treatment and were profiled on the Ovarian cancer DSA™. Response data was determined by RESIST and/or the serum marker CA125 levels. Applying the 44-gene DDRD classifier model to these samples proved to separate the responders from the non-responders significantly, with an AUC of ~0.68 and a lower confidence limit of approx 0.59 (FIG. 6). The 44-gene DDRD classifier model detects dysfunction of the Fanconi Anemia/BRCA pathway.

Figure 7:
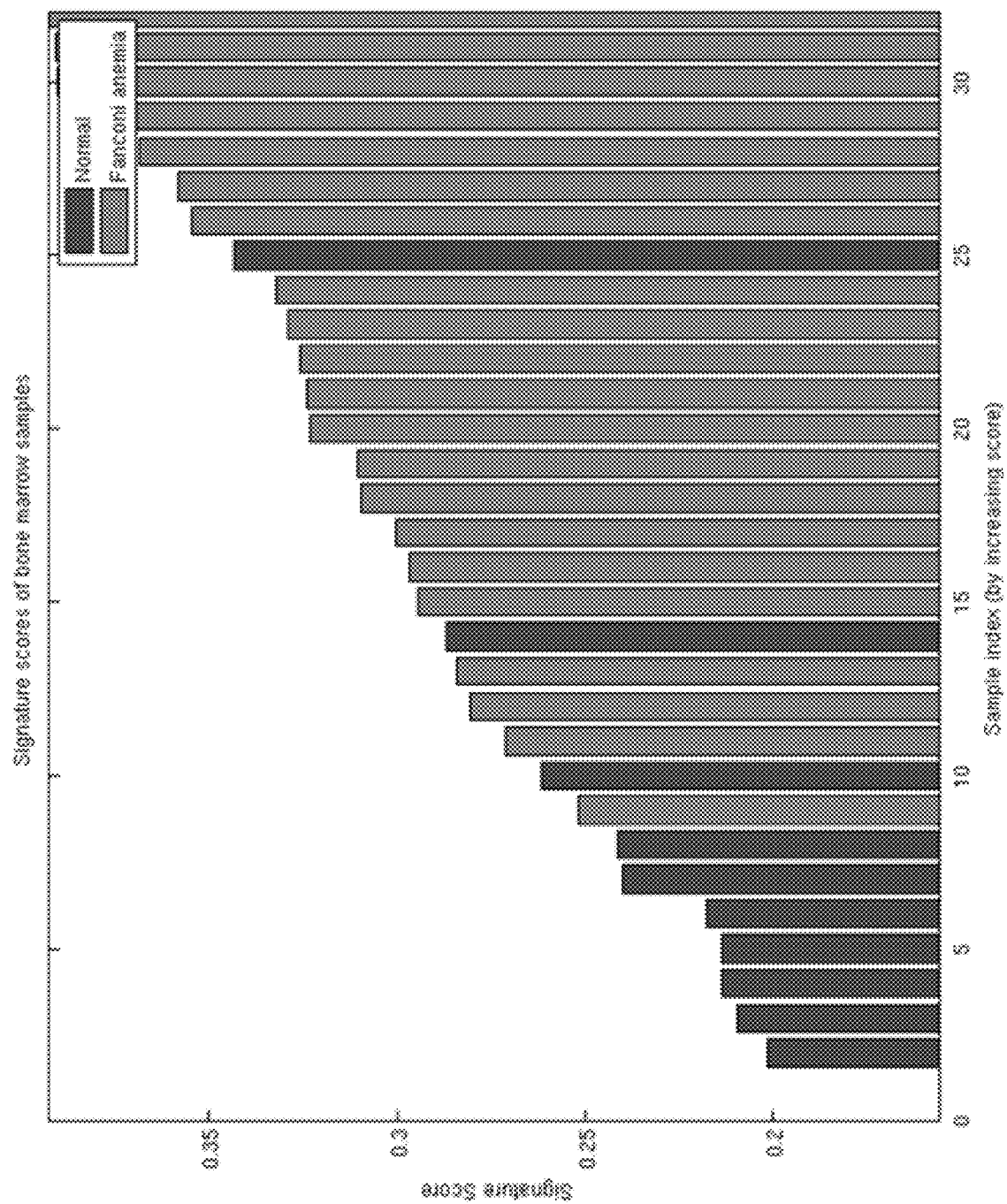
FIG. 7 provides a histogram representation of the 44-gene DDRD classifier scores in bone marrow samples taken from healthy donors and patients with Fanconi Anaemia mutations. The AUC is 0.90 following application of the classifier model. The 95% confidence limits were determined using 1000 bootstrap iterations.
Figure 8A:
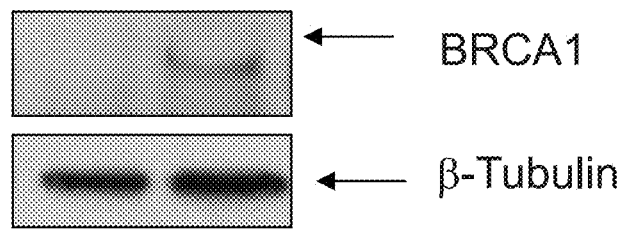
FIG. 8A, FIG. 8B, FIG. 8C, and FIG. 8D provide a figure correlating the 44-gene classifier model with therapeutic response in BRCA1 mutant and wildtype cell-lines.
Figure 8B:
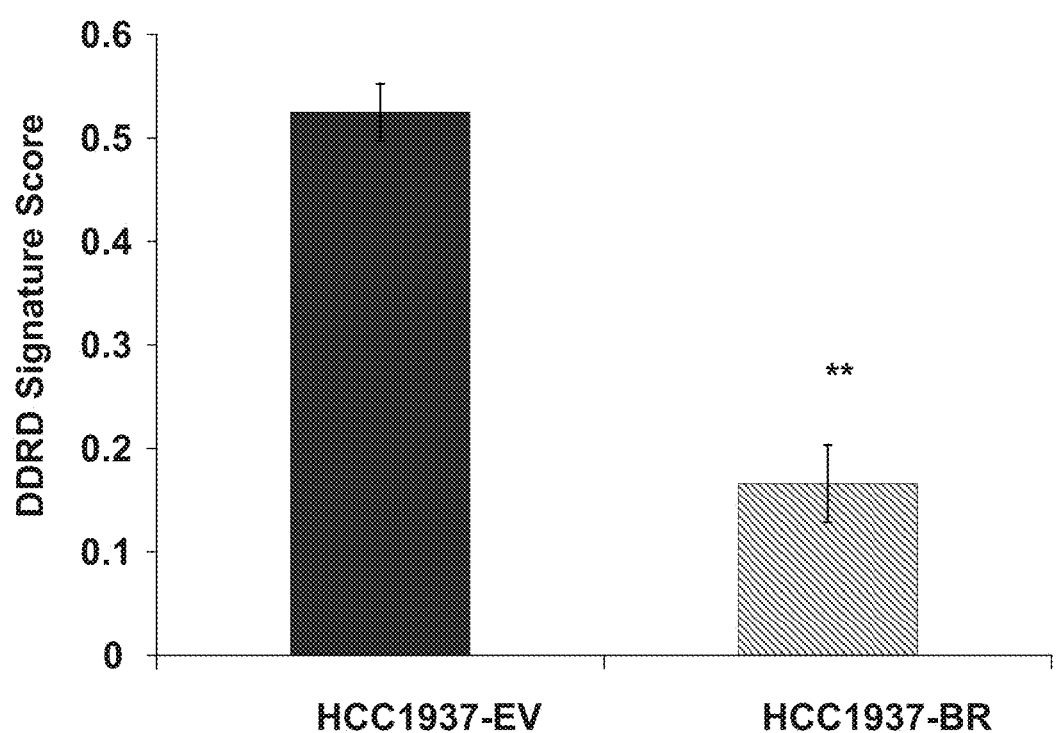
Figure 8C:
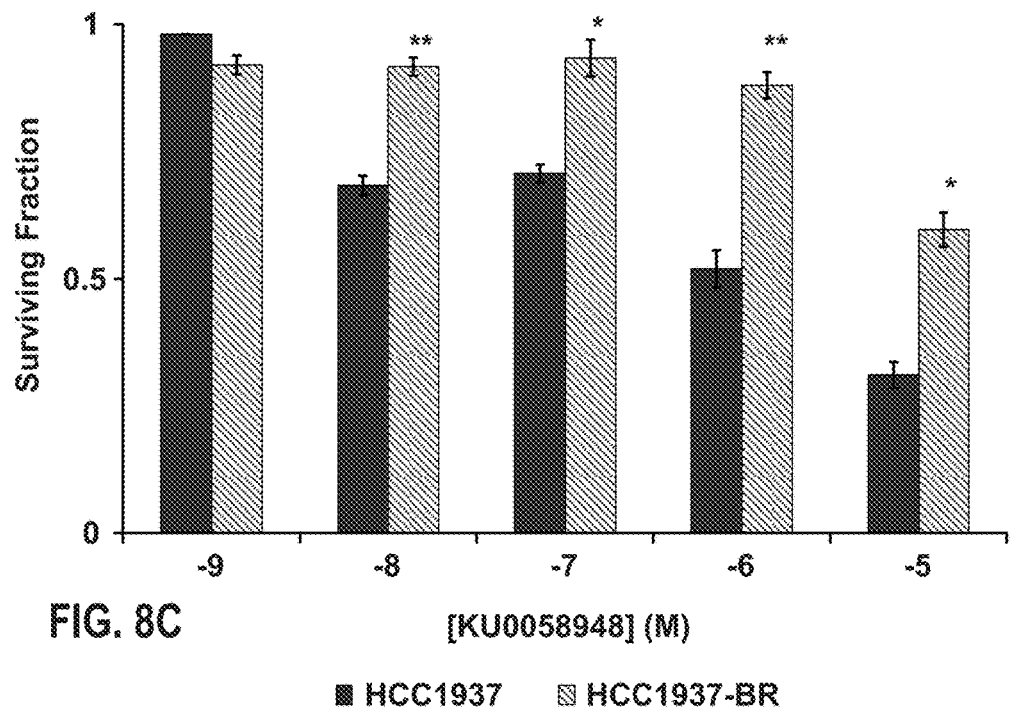
Figure 8D:
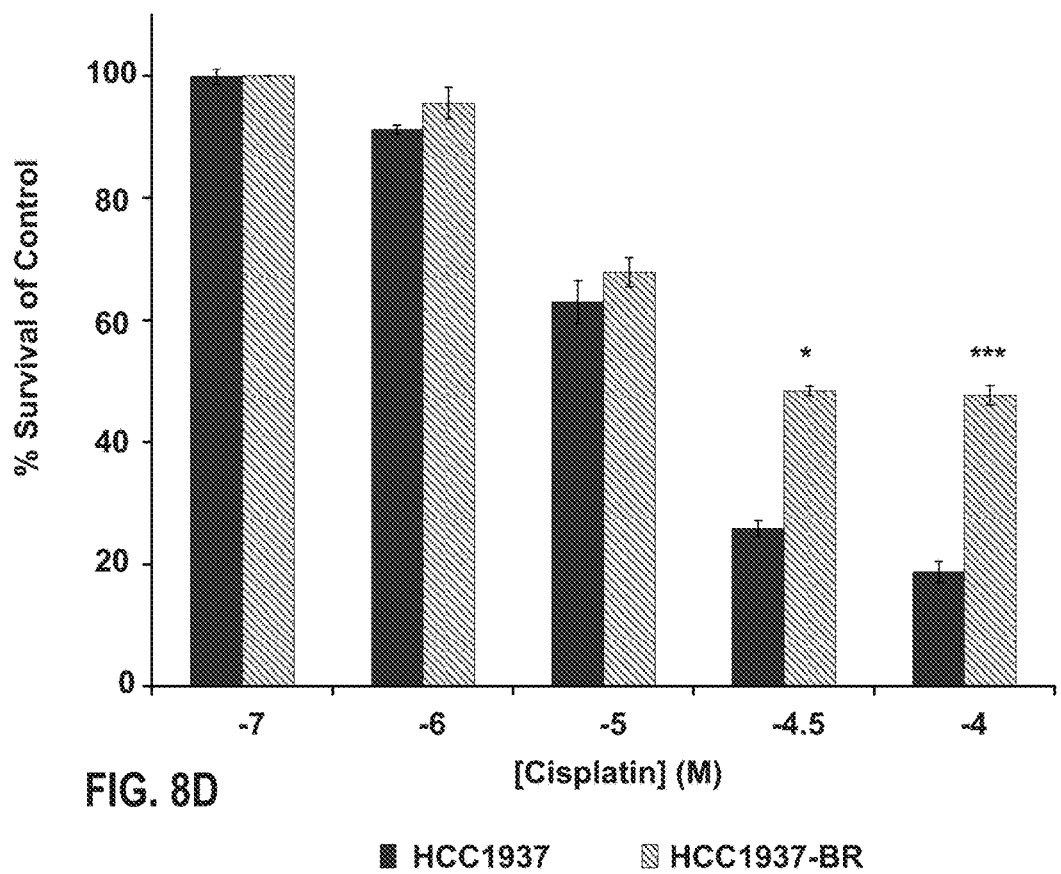

The Fanconi anemia/BRCA (FA/BRCA) pathway, which includes BRCA1 and BRCA2, plays an integral role in DNA repair and can be lost in breast cancer either due to mutation or epigenetic silencing (Kennedy and D'Andrea, 2006). It was therefore determined if the 44-gene DDRD classifier model could detect abrogation of members of this pathway in addition to BRCA1 and BRCA2. A public dataset was identified with microarray data generated from the bone marrow of 21 FA patients carrying a range of mutations in the FA/BRCA pathway and 11 healthy controls with a functional FA/BRCA pathway (Vanderwerf, S. M., et al., Blood 114, 5290-5298 (2009). The 44-gene DDRD classifier model significantly distinguished between the FA/BRCA mutant and normal samples with an AUC of 0.90 (CI=0.76-1.00, P<0.001, FIG. 7), demonstrating a strong correlation between the DDRD classifier and dysfunction of the FA/BRCA pathway through multiple mechanisms.

Summary of in Silico Validation of 44-Gene DDRD Classifier Model

The in silico validation of the 44-gene DDRD classifier model has shown the following:

(a) The 44-gene DDRD classifier model is able to significantly separate BRCA mutant breast tumor samples from wildtype BRCA (sporadic) breast tumor samples. This implies that the DDRD classifier model is capable of detecting biology related to tumors with a high level of genomic instability, such as BRCA mutant tumors. These tumors typically respond better to DNA damaging chemotherapeutic regimens.

(b) The 44-gene DDRD classifier model is able to significantly separate defined responders (those that demonstrated pCR) from the non-responders (those that did not demonstrate pCR) in a combination of three independent breast datasets following neoadjuvant treatment with FAC and FEC (Bonnefoi et al., 2007; Iwamoto et al., 2011; Tabchy et al., 2010) and T/FAC (Hess et al., 2006; Lee et al., 2010; Tabchy et al., 2010). The 44-gene DDRD classifier model was found to be independent of other clinical factors and the most significant independent predictor of response in the FAC/FEC combined analysis. These studies were carried out using fresh frozen (FF) samples and using two different microarray platforms, namely the Affymetrix X3P microarray and the Affymetrix U133A microarray. These results validate the performance of the 44-gene DDRD classifier model within independent breast datasets utilizing a different sample material (FF instead of FFPE) and utilizing microarray data from two different microarray platforms.

(c) The 44-gene DDRD classifier model is able to significantly separate responders from non-responders within an independent Almac ovarian dataset following adjuvant treatment with platinum or platinum/taxane based therapy. This data was generated using FFPE samples profiled upon the Almac Ovarian DSA™.

(d) The 44-gene DDRD classifier model is able to significantly distinguish between FA/BRCA mutant and normal samples using bone marrow tissue samples, demonstrating a strong correlation between the DDRD classifier and dysfunction of the FA/BRCA pathway through multiple mechanisms.

In summary, the DDRD classifier model has been independently validated and demonstrated robustness in performance across three different disease areas (breast, ovarian and FA), demonstrated ability to separate responders from non-responders to four different chemotherapeutic regimens (FAC, FEC, T/FAC and platinum/taxane) in two different sample types (FFPE and FF) utilizing data from four different microarray platforms (Almac Breast DSA™ and Almac Ovarian DSA™, Affymetrix X3P microarray and Affymetrix U133A microarray). It has been demonstrated that the DDRD is an independent predictor of response to DNA-damage therapeutic agents and can predict mutations in the FA/BRCA pathways. This plasticity and repeatability of performance implies that the biology identified within the DDRD subgroup identified via the 44-gene classifier model is significantly and robustly related to predicting response to DNA damage causing agents and as such supports the claim of this invention which is to identify a subtype that can be used to predict response to, and select patients for, standard breast and ovarian cancer therapeutic drug classes, including drugs that damage DNA directly, damage DNA indirectly or inhibit normal DNA damage signaling and/or repair processes.

TABLE 3

Performance metrics and independence assessment of the 44-gene DDRD classifier model in breast datasets
Numbers in brackets denote the 95% confidence limits from +/− 2SD from cross-validation (A) or bootstrapping with 1000 repeats (B).

| Data set | No. | Treatment | Clinical Outcome | AUC(CI) | ACC (CI) | SENS (CI) | SPEC (CI) | PPV (CI) | NPV (CI) | RR(CI) |
|---|---|---|---|---|---|---|---|---|---|---|
| (A) Prediction of BRCA mutation status using the 44-gene DDRD classifier model | | | | | | | | | | |
| Training | 107 | N/A | BRCA mutant V wildtype | 0.68 (0.56-0.78) | 0.70 (0.57-0.76) | 0.58 (0.48-0.65) | 0.79 (0.64-0.86) | 0.78 (0.63-0.85) | 0.60 (0.49-0.65) | 1.93 (1.23-2.55) |
| (B) Prediction of pCR using 44-gene DDRD classifier model | | | | | | | | | | |
| FAC1 FAC2 and FEC | 203 | FEC and FAC | pCR V RD | 0.78 (0.70-0.85) | 0.76 (0.64-0.83) | 0.82 (0.69-0.92) | 0.58 (0.52-0.62) | 0.44 (0.36-0.48) | 0.90 (0.81-0.95) | 4.13 (1.94-9.87) |
| T/FAC | 321 | T/FAC | pCR V RD | 0.61 (0.53-0.69) | 0.53 (0.43-0.62) | 0.49 (0.38-0.60) | 0.67 (0.64-0.70) | 0.29 (0.22-0.35) | 0.83 (0.80-0.87) | 1.72 (1.05-2.65) |

AUC = Area Under the Receiver Operating Characteristics Curve;
ACC = Accuracy;
SENS = Sensitivity;
SPEC = Specificity;
PPV = Positive Predictive value;
NPV = Negative Predictive Value;
RR = Relative Risk,
pCR = pathological complete response,
RD = residual disease.

TABLE 4

Univariate and Multivariate Analysis of the 44-gene DDRD classifier model
Comparison of the 44-gene DDRD classifier model to standard pathological parameters in independent validation sets. The predictive value of the DDRD classifier model as well as significant clinical parameters were evaluated in a univariate and multivariate analysis using logistic regression models with p-values coming from a log-likelihood test.
Univariate and Multivariate Analysis of the 44-gene DDRD classifier model

| FAC1, FAC2 and FEC Variable | Univariate P value | Multivariate P value |
|---|---|---|
| DDRD classifier | 0.0000 | 0.0014 |
| ER | 0.0004 | 0.0249 |
| Stage | 0.0459 | 0.0492 |
| Grade | 0.0100 | 0.0468 |

| T/FAC Variable | Univariate P value | Multivariate P value |
|---|---|---|
| DDRD classifier | 0.0129 | 0.2100 |
| ER | 0.0000 | 0.0000 |
| Stage | 0.3626 | 0.0359 |
| Grade | 0.0000 | 0.0115 |

Example 3

In Vitro Validation of the 44-Gene DDRD Classifier Model

In order to assess the biology underlying the genes contained within the 44-gene classifier model, a number of studies were carried out in vitro using a panel of breast cell-lines.

Methods

Maintenance of Cell-Lines

The HCC1937 parental, HCC1937-EV and HCC1937-BR cell-lines were kindly donated by Professor Paul Harkin from Queen's University College Belfast (QUB). The cell-lines were routinely maintained in RPMI-1640 medium supplemented with 50 U penicillin/ml, 50 µg streptomycin/ml, 2 mM glutamine, 1 mM Sodium Pyruvate and 20% (v/v) fetal bovine serum (FBS). The HCC1937-EV and HCC937-BR cell-lines also required 0.2 ml/mg geneticin. Cell-lines were cultured at 37° C. with a humidified atmosphere of 5% $CO_2$.

Clonogenic Assays—Determination of PARP-1 Inhibitor Sensitivity

For measurement of sensitivity to PARP-1 inhibitor (KU0058948), exponentially growing cells were seeded into 6-well plates. Twenty-four hours following seeding the cells were exposed to medium containing increasing doses of drug. Cell medium was replenished every 4-5 days. After 12-14 days the cells were fixed in methanol, stained with crystal violet and counted. The percentage survival of control for a given dose was calculated as the plating efficiencies for that dose divided by the plating efficiencies of vehicle-treated cells. Survival curves and half maximal inhibitory concentration ($IC_{50}$) values were calculated using GraphPad Prism.

Cell Viability Assay—Determination of Cisplatin Sensitivity

For measurement of sensitivity to cisplatin, exponentially growing cells were seeded into 96-well plates. 24 hours following seeding the cells were exposed to medium containing increasing doses of cisplatin. Cells were incubated in the presence of drug for 96 hours following which time the viability of the cells was assessed using the Promega CellTitre-Glo luminescent cell viability assay. The sensitivity of the cells was calculated as the percentage of vehicle (DMSO) control. Survival curves and half maximal inhibitory concentration ($IC_{50}$) values were calculated using GraphPad Prism.

Results

The DDRD Subgroup can be Identified within Breast Cancer Cell-Line Models

A preclinical model system was used to confirm that the 44-gene DDRD classifier was a measure of abnormal DDR. The HCC1937 breast cancer cell-line is DDRD due to a BRCA1 mutation (Tomlinson et al., 1998). The 44-gene classifier was applied to HCC1937 empty vector control cells (HCC1937-EV) and HCC1937 cells in which BRCA1 functionality was corrected (HCC1937-BR) (FIG. 7A). The DDRD 44-gene classifier score was found to be higher within HCC1937-EV relative to HCC1937-BR cells, with average scores of 0.5111 and 0.1516 respectively (FIG. 7B). Consistent with the DDRD 44-gene classifier scores, the HCC1937 BRCA1 mutant cell-line was more sensitive to the PARP-1 inhibitor KU0058948 (FIG. 7C) and cisplatin (FIG. 7D) relative to the BRCA1 corrected cell-line. These preclinical data suggest that the DDRD 44-gene classifier measures immune signalling in DDRD-positive tumor cells and correlates with response to both a DNA-damaging agent (cisplatin) and a DNA repair targeted agent (PARP-1 inhibitor).

The DDRD 44-Gene Classifier Detects Dysfunction of the Fanconi Anemia/BRCA Pathway The Fanconi anemia/BRCA (FA/BRCA) pathway, which includes BRCA1 and BRCA2, plays an integral role in DNA repair and can be lost in breast cancer either due to mutation or epigenetic silencing (Kennedy, R. D., and D'Andrea, A. D., J Clin Oncol 24, 3799-3808 (2006)). It was determined if the DDRD 44-gene classifier could detect abrogation of members of this pathway in addition to BRCA1 and BRCA2. A public dataset was identified with microarray data generated from the bone marrow of 21 FA patients carrying a range of mutations in the FA/BRCA pathway and 11 healthy controls with a functional FA/BRCA pathway (Vanderwerf et al., 2009). The DDRD 44-gene classifier significantly distinguished between the FA/BRCA mutant and normal samples with an AUC of 0.90 (CI=0.76-1.00, P<0.001), demonstrating a strong correlation between the DDRD classifier and dysfunction of the FA/BRCA pathway through multiple mechanisms.

CONCLUSION

The DDRD 44-gene classifier score was significantly higher in the BRCA1 mutant, and thus DDRD, HCC1937 breast cancer cell-line relative to an isogenic BRCA1 corrected cell-line. As the 44-gene classifier score correlates with DDR dysfunction within these cells, it demonstrates that the immune signalling detected by the DDRD classifier is intrinsic to the cell and not a function of lymphocytic infiltrate. BRCA1 and BRCA2 represent part of the FA/BRCA DDR network, which contains a number of other proteins that have been reported to be mutant or under-expressed in approximately 33% of breast cancer (Kennedy, R. D., and D'Andrea, A. D., J Clin Oncol 24, 3799-3808 (2006). As described previously, the DDRD 44-gene classifier significantly separated bone marrow samples from patients with FA mutations from normal controls. This suggests that the DDRD classifier is capable of detecting any abnormality within the pathway rather than specifically BRCA1 or BRCA2 dysfunction. It is possible that the DDRD 44-gene classifier may identify tumors with DDR-deficiency due to other mechanisms such as PTEN loss, cell-cycle checkpoint dysfunction or increased reactive oxygen species due to metabolic disturbance. Due to constitutive DNA-damage, these tumors are likely to respond to DNA repair targeted therapies such as PARP-1 or CHK1/2 inhibitors.

We claim:

1. A method of predicting response of an individual to, and treating an individual with, a modulator of DNA-damage-related immune signalling, comprising:
   a. measuring expression levels of at least five biomarkers in a test sample of cancer cells obtained from the individual, wherein the at least five biomarkers are selected from the group consisting of CXCL10, MX1, IDO1, IFI44L, CD2, GBP5, PRAME, ITGAL, LRP4, and APOL3;
   b. deriving a combined test score that captures the expression levels;
   c. providing a threshold score comprising information correlating the test score and responsiveness to the modulator of DNA-damage-related immune signalling; wherein the individual is predicted to respond to the modulator of DNA-damage-related immune signalling when the test score exceeds the threshold score; and
   d. treating the individual that is so predicted to respond with the modulator of DNA-damage-related immune signalling.

2. The method of claim 1, further comprising measuring expression level(s) of one or more additional biomarkers in the test sample wherein the one or more additional biomarkers are selected from the group consisting of CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

3. The method of claim 1, wherein the test score captures the expression levels of all biomarkers from the group consisting of CXCL10, MX1, IDO1, IFI44L, CD2, GBP5, PRAME, ITGAL, LRP4, and APOL3, and wherein the individual is diagnosed as having a DDRD cancer when the test score exceeds the threshold score.

4. The method of claim 1, wherein the cancer is selected from melanoma, breast cancer, and ovarian cancer.

5. The method of claim 4, wherein the cancer is associated with one or more mutations in the Fanconi anemia/BRCA pathway.

6. The method of claim 1, wherein the modulator of DNA-damage-related immune signalling is selected from cisplatin and ionising radiation.

7. The method of claim 1, wherein at least one of the biomarkers is CXCL10.

8. A method of predicting response of an individual to, and treating an individual with, a DNA-damage therapeutic agent, comprising:
   a. measuring expression levels of at least five biomarkers in a test sample of cancer cells obtained from the individual, wherein the at least five biomarkers are selected from the biomarkers in Table 2B;
   b. deriving a combined test score that captures the expression levels; and
   c. providing a threshold score comprising information correlating the test score and responsiveness to a DNA-damage therapeutic agent;
   wherein the individual is predicted to respond to a DNA-damage therapeutic agent when the test score exceeds the threshold score; and
   d. treating the individual that is so predicted to respond with a DNA-damage therapeutic agent.

9. The method of claim 8, wherein the combined test score captures the expression levels of all 44 biomarkers in Table 2B, and wherein the individual is diagnosed as having a DDRD cancer when the test score exceeds a threshold score calculated using the weights of Table 2B.

10. The method of claim 8, wherein the cancer is selected from melanoma, breast cancer, and ovarian cancer.

11. The method of claim 10, wherein the cancer is associated with one or more mutations in the Fanconi anemia/BRCA pathway.

12. The method of claim 8, wherein the DNA-damage therapeutic agent comprises one or more substances selected from the group consisting of: a DNA damaging agent, a DNA repair targeted therapy, an inhibitor of DNA damage signalling, an inhibitor of DNA damage induced cell cycle arrest, a histone deacetylase inhibitor, and a heat shock protein inhibitor.

13. The method of claim 8, wherein the DNA-damage therapeutic agent is a modulator of DNA-damage-related immune signalling.

14. The method of claim 12, wherein the DNA damaging agent is selected from cisplatin, carboplatin, oxaliplatin and cyclophosamide; the Topoisomerase I inhibitors Irinotecan and toptecan; the Topoisomerase II inhibitors etoposide, doxorubicin, and epirubicin; ionising radiation; the DNA repair targeted DNA-PK inhibitors Nu7441 and NU7026, PARP inhibitors, AZD2281, AG014699, ABT-888, MK4827, BSI-201, and TRC-102; the inhibitors of DNA damage signalling ATM inhibitors CP466722 and KU-55933; the CHK1/CHK2 inhibitors XL-844, AZD7762, and PF00477736; and heat shock protein inhibitors geldanamycin and AUY922.

15. The method of claim 13, wherein the modulator of DNA-damage-related immune signalling is selected from cisplatin and ionising radiation.

16. The method of claim 8, wherein at least one of the biomarkers is CXCL10.

17. A method of treating an individual predicted to respond to a modulator of DNA-damage-related immune signalling, comprising treating the individual with the modulator of DNA-damage-related immune signalling, wherein the individual has been predicted to respond to the modulator of DNA-damage-related immune signalling prior to treatment when a combined test score exceeds a threshold score, wherein the combined test score determination has been done by a method comprising:
   a. measuring expression levels of at least five biomarkers in a test sample of cancer cells obtained from the individual, wherein the at least five biomarkers are selected from the biomarkers in Table 2B;
   b. deriving a combined test score that captures the expression levels; and
   c. providing a threshold score comprising information correlating the test score and responsiveness to the modulator of DNA-damage-related immune signalling;
   wherein the individual is predicted to respond to the modulator of DNA-damage-related immune signalling when the test score exceeds the threshold score.

18. The method of claim 17, wherein the combined test score captures the expression levels of all 44 biomarkers in Table 2B, and wherein the individual is diagnosed as having a DDRD cancer when the test score exceeds a threshold score calculated using the weights of Table 2B.

19. The method of claim 17, wherein the cancer is selected from melanoma, breast cancer, and ovarian cancer.

20. The method of claim 19, wherein the cancer is associated with one or more mutations in the Fanconi anemia/BRCA pathway.

21. The method of claim 17, wherein the modulator of DNA-damage-related immune signalling is selected from cisplatin and ionising radiation.

22. The method of claim 17, wherein at least one of the biomarkers is CXCL10.

23. A method of predicting response of an individual to, and treating an individual with, a DNA-damage therapeutic agent, comprising:
   a. measuring expression levels of at least two biomarkers in a test sample of cancer cells obtained from the individual, wherein at least one biomarker is selected from the group consisting of CXCL10, IDO1, and APOL3;
   b. deriving a combined test score that captures the expression levels;
   c. providing a threshold score comprising information correlating the test score and responsiveness to a DNA-damage therapeutic agent;
   wherein the individual is predicted to respond to a DNA-damage therapeutic agent when the test score exceeds the threshold score; and
   d. treating the individual that is so predicted to respond with a DNA-damage therapeutic agent.

24. The method of claim 23, further comprising measuring expression level(s) of one or more additional biomarkers in the test sample wherein the one or more additional biomarkers are selected from the group consisting of CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

25. The method of claim 23, wherein the test score captures the expression levels of all biomarkers from the group consisting of CXCL10, MX1, IDO1, IFI44L, CD2, GBP5, PRAME, ITGAL, LRP4, and APOL3, and wherein the individual is diagnosed as having a DDRD cancer when the test score exceeds the threshold score.

26. The method of claim 23, wherein the cancer is selected from melanoma, breast cancer, and ovarian cancer.

27. The method of claim 26, wherein the cancer is associated with one or more mutations in the Fanconi anemia/BRCA pathway.

28. The method of claim 23, wherein the DNA-damage therapeutic agent comprises one or more substances selected from the group consisting of: a DNA damaging agent, a DNA repair targeted therapy, an inhibitor of DNA damage signalling, an inhibitor of DNA damage induced cell cycle arrest, a histone deacetylase inhibitor, and a heat shock protein inhibitor.

29. The method of claim 23, wherein the DNA-damage therapeutic agent is a modulator of DNA-damage-related immune signalling.

30. The method of claim 29, wherein the modulator of DNA-damage-related immune signalling is selected from cisplatin and ionising radiation.

31. The method of claim 23, wherein at least one of the biomarkers is CXCL10.

\* \* \* \* \*

SEQUENCE LISTING

```
<160> NUMBER OF SEQ ID NOS: 202

<210> SEQ ID NO 1
<211> LENGTH: 541
<212> TYPE: DNA
<213> ORGANISM: Homo sapiens

<400> SEQUENCE: 1
gggaccaagg tggagatcaa acgtaagtgc actttcctaa tgcttttttct tataaggttt      60 taaatttgga gccttttttgt gtttgagata ttagctcagg tcaattccaa agagtaccag     120
attctttcaa aaagtcagat gagtaaggga tagaaaagta gttcatctta aggaacagcc     180
aagcgctagc cagttaagtg aggcatctca attgcaagat tttctctgca tcggtcaggt     240
tagtgatatt aacagcgaaa agagatttttt gtttagggga aagtaattaa gttaacactg     300
tggatcacct tcggccaagg gacacgactg gagattaaac gtaagtaatt tttcactatt     360
```

```
gtcttctgaa atttgggtct gatggccagt attgactttt agaggcttaa ataggagttt      420
ggtaaagatt ggtaaatgag ggcatttaag atttgccatg ggttgcaaaa gttaaactca      480
gcttcaaaaa tggatttgga gaaaaaaaga ttaaattgct ctaaactgaa tgacacaaag      540
t                                                                      541

<210> SEQ ID NO 2
<211> LENGTH: 600
<212> TYPE: DNA
<213> ORGANISM: Homo sapiens

<400> SEQUENCE: 2
tttattggtc ttcagatgtg gctgcaaaca cttgagactg aactaagctt aaaacacggt       60
acttagcaat cgggttgcca gcaaagcact ggatgcaagc cttgccttcc agaagcttac      120
cagtcgggtt gccagcaaag cagtggatgc aagacttgcc ctccaggagc ttaccatcac      180
aacgaagaag acaaataaat gcataatata tagacgacat aaatccatac tgtacacatt      240
taagaataaa cagtccagta gtaagaggca gtacatattc aatctgctga gaaatgtaga      300
caataactac tataagaatc ctaatgctac agaagtcact ggctgctggg aaaccgggga      360
aaacttggct atggacgtgg gggcttgtgt cggactctga ataaagagca gaatgattgg      420
cgtcctactg agatacatag taaaggggc gagggcaggg aggaagtggc aagaataaca       480
tttgtgaaga tgtccaggtg agaaatagag gttttaatgc tcaagatgtt ccttttccc       540 ttttaaatct gacctgtgat ttccagcatt gctatttcga atatcactga ttgttttttaa    600

<210> SEQ ID NO 3
<211> LENGTH: 600
<212> TYPE: DNA
<213> ORGANISM: Homo sapiens

<400> SEQUENCE: 3
tgtggcacat ataccatg gaatactatg cagccataaa aaagaatggg atcatgtcct         60
gtgcagcaac gtggatggag ctggaagcca ttatcctaaa tgaactcact cagaaacaga      120
aaaccaaata ccacatgttc tcacttataa gtagaagcta acattgagt acacatggat       180 acaaagaagg gaaccgcaga cactggggcc tacctgaggt cggagcatgg aaggagggtg      240
aggatcaaaa aactacctat ctggtactat gcttttatc tggatgatga ataatctgt        300 acaacaaacc ctggtgacat gcaatttacc tatatagcaa gcctacacat gtgcccctga     360
acctaaaaaa aaagttaaaa gaaaacgtt tggattattt tccctctttc gaacaaagac       420
attggtttgc ccaaggacta caaataaacc aacgggaaaa agaaaggtt ccagttttgt       480 ctgaaaattc tgattaagcc tctgggccct acagcctgga gaacctggag aatcctacac     540
ccacagaacc cggctttgtc cccaaagaat aaaaacacct ctctaaaaaa aaaaaaaaaa     600

<210> SEQ ID NO 4
<211> LENGTH: 600
<212> TYPE: DNA
<213> ORGANISM: Homo sapiens

<400> SEQUENCE: 4
tccttatggg gcccggtatg tgggctccat ggtggctgat gttcatcgca ctctggtcta      60
cggagggata tttctgtacc ccgctaacaa gaagagcccc aatggaaagc tgagactgct     120
gtacgaatgc aaccccatgg cctacgtcat ggagaaggct gggggaatgg ccaccactgg    180
gaaggaggcc gtgttagacg tcattcccac agacattcac cagagggcgc cggtgatctt    240
```

```
gggatccccc gacgacgtgc tcgagttcct gaaggtgtat gagaagcact ctgcccagtg    300
agcacctgcc ctgcctgcat ccggagaatt gcctctacct ggacctttg tctcacacag     360 cagtaccctg acctgctgtg caccttacat tcctagagag cagaaataaa aagcatgact    420
atttccacca tcaaatgctg tagaatgctt ggcactccct aaccaaatgc tgtctccata    480
atgccactgg tgttaagata tattttgagt ggatggagga gaaataaact tattcctcct    540
taaaaaaaaa aaaaaaaaaa aaaaaaaaaa aaaaaaaaaa aaaaaaaaaa aaaaaaaaaa    600

<210> SEQ ID NO 5
<211> LENGTH: 600
<212> TYPE: DNA
<213> ORGANISM: Homo sapiens

<400> SEQUENCE: 5
cgggcgtggt agcgggcgcc tgtagtccca gctactcggg aggctgaggc aggagaatgg     60
cgtgaacccg ggaggcggag cttgcagtga gccgagatcg cgccactgca ctccagcctg    120
ggcgacagag cgagactccg tctcaaaaaa aaaaaaaaaa aaaaaatac aaaaattagc     180 cgggcgtggt ggcccacgcc tgtaatccca gctactcggg aggctaaggc aggaaaattg    240
tttgaaccca ggaggtggag gctgcagtga gctgagattg tgccacttca ctccagcctg    300
ggtgacaaag tgagactccg tcacaacaac aacaacaaaa agcttcccca actaaagcct    360
agaagagctt ctgaggcgct gctttgtcaa aaggaagtct ctaggttctg agctctggct    420
ttgccttggc tttgccaggg ctctgtgacc aggaaggaag tcagcatgcc tctagaggca    480
aggaggggag gaacactgca ctcttaagct tccgccgtct caaccctca caggagctta     540 ctggcaaaca tgaaaatcg gcttaccatt aaagttctca atgcaaccat aaaaaaaaaa    600

<210> SEQ ID NO 6
<211> LENGTH: 600
<212> TYPE: DNA
<213> ORGANISM: Homo sapiens

<400> SEQUENCE: 6
tacagatact cagaagccaa taacatgaca ggagctggga ctggtttgaa cacagggtgt     60
gcagatgggg aggggtact ggccttgggc tcctatgat gcagacatgg tgaatttaat     120
tcaaggagga ggagaatgtt ttaggcaggt ggttatatgt gggaagataa ttttattcat    180
ggatccaaat gtttgttgag tcctttcttt gtgctaaggt tcttgcggtg aaccagaatt    240
ataacagtga gctcatctga ctgttttagg atgtacagcc tagtgttaac attcttggta    300 tcttttgtg ccttatctaa aacatttctc gatcactggt ttcagatgtt catttattat      360
attcttttca aagattcaga gattggcttt tgtcatccac tattgtatgt tttgtttcat    420
tgacctctag tgataccttg atcttttccca cttttctgttt tcggattgga gaagatgtac   480
cttttttgtc aactcttact tttatcagat gatcaactca cgtatttgga tctttatttg    540
ttttctcaaa taaatattta aggttataca tttaaaaaaa aaaaaaaaaa aaaaaaaaaa    600

<210> SEQ ID NO 7
<211> LENGTH: 600
<212> TYPE: DNA
<213> ORGANISM: Homo sapiens

<400> SEQUENCE: 7
tgagaagtag ttactgtgca catgtgtaga tttgcagttc tgtggctcct gatggatctg     60
```

```
agaagatgga cgtggaggat gaaaatctgt ctgattattt tgaactgatg tttgttgcta    120
tggagatgct gcctatatgt tgatgttgca gacgttaagt cactagccca cagccttgta    180
ttccatactc agagaccctg ctacttactt gacatctcaa cttgaaagtc caattaatat    240
gcacttcaaa ctttaatagg cttcaaacag aatttctttc attatctctg caaaacagct    300
tctctcatca tcttgaaatt agtgaatggc attttactgt tttagttgga gtcatttctg    360
tggttttctt tcacatccta cataacaatc catcagtaag ttctatgagc tcttctttga    420
aaacaaacag aatccaactg tttcattccc acttctgctc tggtcaagcc actgccaaca    480 ctcacccttta ttattgtagc accctcattg cctagttctg tcccacagat ttccaataaa    540
aggtgaataa aatcaggtca ctcttctgct aaaaaaaaaa aaaaaaaaaa aaaaaaaaa     600
```

<210> SEQ ID NO 8
<211> LENGTH: 600
<212> TYPE: DNA
<213> ORGANISM: Homo sapiens
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (356)..(364)
<223> OTHER INFORMATION: n is a, c, g, or t

<400> SEQUENCE: 8

```
nnnnntttgc tacagccagg gttagctcag caggtgaaaa ccccgagggt gggtgaaacc    60
cctctggggc tcagacatgc aaaccttggg catctctctg tcccagctgg ccccgccagc    120
cggtaggaag tttcccctga gttctcagtt ttttcttctg aaaaatgagg ggttgtatgc    180
aaggttctcc tcctggcctg tggtccccag agaagggcag gaaggaacct tagataattc    240
tcatatgcat ttaacagacg aggaaactga gacccagagc cgtcacatca atacctcatt    300
tgatcttcat aagagcacct ggaggagggg ggtgggggtgt ttgtgtttgt ttaaannnnn    360
nnnngtgaaa aaaatgaaga taggcatttt gtagacaatc tggaagttct ggaccggaat    420
ccatgatgta gtcagggaag aaatgacccg tgtccagtaa ccccaggcct cgagtgtgtg    480
gtgtattttt ctacataatt gtaatcattc tatacataca aattcatgtc ttgaccatca    540
tattaatatt tggtaagttt ctctctcttt agagactcca caataaagtt ttcaacatgg    600
```

<210> SEQ ID NO 9
<211> LENGTH: 394
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (201)..(223)
<223> OTHER INFORMATION: n is a, c, g, or t
<220> FEATURE:
<221> NAME/KEY: misc_feature
<222> LOCATION: (226)..(227)
<223> OTHER INFORMATION: n is a, c, g, or t
<220> FEATURE:
<221> NAME/KEY: misc_feature
<222> LOCATION: (229)..(232)
<223> OTHER INFORMATION: n is a, c, g, or t

<400> SEQUENCE: 9

| | | | | | |
|---|---|---|---|---|---|
| tnttntnttt | tttttttttt | tttttttttt | tncatagttg | ttatcttaag | gtgatttcca | 60 |
| atttttttt | ccatttacat | ttttccacaa | gcattgtcca | ctttattctg | taacctttc | 120 |
| aactaccatt | ttgaaatttg | cttttatcca | tgtggttgtt | tgtgatgaac | tacaggttgc | 180 |
| tgactttctt | cccttctgt | nnnnnnnnnn | nnnnnnnnnn | nnngtnntnn | nnctcaagag | 240 |
| gatctcatca | gtggaatcat | tagatcaaag | gatatgactg | ttgctcagct | ctctgtgtgt | 300 |
| atgtaaatta | ataggctgtt | tatttgagca | gttgtaggct | tacaaaaata | ttgagtcaaa | 360 |
| agtatagaat | tcccatatat | tctcctcttc | tccc | | | 394 |

<210> SEQ ID NO 10
<211> LENGTH: 600
<212> TYPE: DNA
<213> ORGANISM: Homo sapiens

<400> SEQUENCE: 10

| | | | | | |
|---|---|---|---|---|---|
| atcttcccac | ctcgatgggg | ggttgctgat | aagaccttca | ggcctcctta | ttaccatagg | 60 |
| aactgcatga | gtgagttcat | gggactcatc | cgaggtcact | atgaggcaaa | gcaaggtggg | 120 |
| ttcctgccag | ggggagggag | tctacacagc | acaatgaccc | ccatggacc | tgatgctgac | 180 |
| tgctttgaga | aggccagcaa | ggtcaagctg | gcacctgaga | ggattgccga | tggcaccatg | 240 |
| gcatttatgt | ttgaatcatc | tttaagtctg | gcggtcacaa | agtggggact | caaggcctcc | 300 |
| aggtgtttgg | atgagaacta | ccacaagtgc | tgggagccac | tcaagagcca | cttcactccc | 360 |
| aactccagga | acccagcaga | acctaattga | gactggaaca | ttgctaccat | aattaagagt | 420 |
| agatttgtga | agattcttct | tcagaatctc | atgctttctg | gtagtattgg | aggagggggt | 480 |
| tggttaaaat | gaaaattcac | ttttcatagt | caagtaactc | agaactttta | tggaaacgca | 540 |
| tttgcaaagt | tctatggctg | tcaccttaat | tactcaataa | acttgctggt | gttctgtgga | 600 |

<210> SEQ ID NO 11
<211> LENGTH: 600
<212> TYPE: DNA
<213> ORGANISM: Homo sapiens

<400> SEQUENCE: 11

| | | | | | |
|---|---|---|---|---|---|
| gggagctaag | tatccagcct | ctcccaaacc | tctttgaaca | aagcttctgt | ccctcccaca | 60 |
| cctctcacct | cacaggcaca | tcaggctgca | gaatgcgctt | tagaaagcat | tgttttagtc | 120 |
| caggcacagt | ggctcacgcc | tgtaatccca | gcactttggg | aggccgaggt | gggtggatca | 180 |
| caaggttggg | agattgagac | catcctggct | aacacagtga | aaccctgtct | ctactaaaaa | 240 |
| aatacaaaaa | attagcttgg | cgtggtggtg | ggcgcctgta | gtcccagcag | cttgggaggc | 300 |
| tgaggctgga | gaatggtgtg | aacccaggag | gcggagcttg | cagtgagcca | agatcgcgcc | 360 |
| actgcactcc | agcccgggtg | acagagcaag | actccgtctc | aaaaaaaaga | aagaaaaaa | 420 |
| gaaagcattt | ttttaattga | gaggggcagg | gctggagaag | gagcaagttg | tggggagcca | 480 |
| ggcttccctc | acgcagcctg | tggtggatgt | gggaaggaga | tcaacttctc | ctcactctgg | 540 |

```
gacagacgat gtatggaaac taaaaagaac atgcggcacc ttaaaaaaaa aaaaaaaaaa      600
```

```
<210> SEQ ID NO 12
<211> LENGTH: 600
<212> TYPE: DNA
<213> ORGANISM: Homo sapiens

<400> SEQUENCE: 12
tttattggtc ttcagatgtg gctgcaaaca cttgagactg aactaagctt aaaacacggt       60
acttagcaat cgggttgcca gcaaagcact ggatgcaagc cttgccttcc agaagcttac      120
cagtcgggtt gccagcaaag cagtggatgc aagacttgcc ctccaggagc ttaccatcac      180
aacgaagaag acaaataaat gcataatata tagacgacat aaatccatac tgtacacatt      240
taagaataaa cagtccagta gtaagaggca gtacatattc aatctgctga gaaatgtaga      300
caataactac tataagaatc ctaatgctac agaagtcact ggctgctggg aaaccgggga      360
aaacttggct atggacgtgg gggcttgtgt cggactctga ataaagagca gaatgattgg      420
cgtcctactg agatacatag taaggggggc gagggcaggg aggaagtggc aagaataaca      480
tttgtgaaga tgtccaggtg agaaatagag gttttaatgc tcaagatgtt tccttttccc      540
ttttaaatct gacctgtgat ttccagcatt gctatttcga atatcactga ttgttttaa      600
```

```
<210> SEQ ID NO 13
<211> LENGTH: 600
<212> TYPE: DNA
<213> ORGANISM: Homo sapiens

<400> SEQUENCE: 13
atcccaaagg cccttttttag ggccgaccac ttgctcatct gaggagttgg acacttgact       60
gcgtaaagtg caacagtaac gatgttggaa ggcttatgat tttactgtgt atgtatttgg      120
gagaagaaat tctgtcagct cccaaaggat aaaccagcag ttgctttatt ggtcttcaga      180
tgtggctgca aacacttgag actgaactaa gcttaaaaca cggtacttag caatcgggtt      240
gccagcaaag cactggatgc aagccttgcc ttccagaagc ttaccagtcg ggttgccagc      300
aaagcagtgg atgcaagact tgccctccag gagcttacca tcacaacgaa gaagacaaat      360
aaatgcataa tatatagacg acataaatcc atactgtaca catttaagaa taaacagtcc      420
agtagtaaga ggcagtacat attcaatctg ctgagaaatg tagacaataa ctactataag      480
aatcctaatg ctacagaagt cactggctgc tgggaaaccg gggaaaactt ggctatggac      540 gtggggggctt gtgtcggact ctgaataaag agcagaatga ttggcaaaaa aaaaaaaaaa      600
```

```
<210> SEQ ID NO 14
<211> LENGTH: 600
<212> TYPE: DNA
<213> ORGANISM: Homo sapiens

<400> SEQUENCE: 14
cgtcttctaa atttccccat cttctaaacc caatccaaat ggcgtctgga agtccaatgt       60
ggcaaggaaa aacaggtctt catcgaatct actaattcca cacctttat tgacacagaa       120 aatgttgaga atcccaaatt tgattgattt gaagaacatg tgagaggttt gactagatga      180
tggatgccaa tattaaatct gctggagttt catgtacaag atgaaggaga ggcaacatcc      240
aaaatagtta agacatgatt tccttgaatg tggcttgaga atatggaca cttaatacta      300 ccttgaaaat aagaatagaa ataaaggatg ggattgtgga atggagattc agttttcatt      360
tggttcatta attctataag ccataaaaca ggtaatataa aaagcttcca tgattctatt      420
```

| | |
|---|---|
| tatatgtaca tgagaaggaa cttccaggtg ttactgtaat tcctcaacgt attgtttcga | 480 |
| cagcactaat ttaatgccga tatactctag atgaagtttt acattgttga gctattgctg | 540 |
| ttctcttggg aactgaactc actttcctcc tgaggctttg gatttgacat tgcatttgac | 600 |

<210> SEQ ID NO 15
<211> LENGTH: 600
<212> TYPE: DNA
<213> ORGANISM: Homo sapiens

<400> SEQUENCE: 15

| | |
|---|---|
| actcaaatgc tcagaccagc tcttccgaaa accaggcctt atctccaaga ccagagatag | 60 |
| tggggagact tcttggcttg gtgaggaaaa gcggacatca gctggtcaaa caaactctct | 120 |
| gaaccctcc ctccatcgtt ttcttcactg tcctccaagc cagcgggaat ggcagctgcc | 180 |
| acgccgccct aaaagcacac tcatcccctc acttgccgcg tcgccctccc aggctctcaa | 240 |
| caggggagag tgtggtgttt cctgcaggcc aggccagctg cctccgcgtg atcaaagcca | 300 |
| cactctgggc tccagagtgg ggatgacatg cactcagctc ttggctccac tgggatggga | 360 |
| ggagaggaca agggaaatgt cagggcgggg agggtgaca gtggccgccc aaggcccacg | 420 |
| agcttgttct tgttctttg tcacagggac tgaaaacctc tcctcatgtt ctgctttcga | 480 |
| ttcgttaaga gagcaacatt ttacccacac acagataaag ttttcccttg aggaaacaac | 540 |
| agctttaaaa gaaaagaaa aaaaagtct ttggtaaatg gcaaaaaaa aaaaaaaaa | 600 |

<210> SEQ ID NO 16
<211> LENGTH: 600
<212> TYPE: DNA
<213> ORGANISM: Homo sapiens

<400> SEQUENCE: 16

| | |
|---|---|
| gggatttgtt aaaatggagg tctttggtga ccttaacaga aagggttttt gaggagtagt | 60 |
| ggagtgggga ggggcagcag gaaggggaga ttgtacacac cccaggagac aagtcttcta | 120 |
| gcagttctgc cagaatgggc aggagagaag tgccatagag ctggaaggct acattgaata | 180 |
| gagaaatttc tttaacttgt tttttaagaa gggtgataaa aaggcatgtt ctgatggtga | 240 |
| tagggatgtt tccataactg gaaagaaatt gatgtgcaag agaaagaata taattgcagg | 300 |
| aggacttgaa gaagttggag agaaaaagcc tttagggacc ctgaaccaat gaatctgaaa | 360 |
| ttccccaact gccagatgta tcttcatttt tcattttccg ggagatgtaa tatgtcctaa | 420 |
| aaatcacagt cgctagattg aaatcaacct taaaaatcat ctagtccaat gtctactccc | 480 |
| agtccactac ttgaatcccc tgtgtccct cccagtagtc gtcttgacaa cctccactga | 540 |
| aaggcaattt ctacactcca tccaccccac caccaaccca tggttcatga tctcttcgga | 600 |

<210> SEQ ID NO 17
<211> LENGTH: 600
<212> TYPE: DNA
<213> ORGANISM: Homo sapiens

<400> SEQUENCE: 17

| | |
|---|---|
| ttactatatc aacaactgat aggagaaaca ataaactcat tttcaaagtg aatttgttag | 60 |
| aaatggatga taaatattg gttgacttcc ggctttctaa gggtgatgga ttggagttca | 120 |
| agagacactt cctgaagatt aaagggaagc tgattgatat tgtgagcagc cagaaggttt | 180 |
| ggcttcctgc cacatgatcg gaccatcggc tctggggaat cctgatggag tttcactctt | 240 |

| | |
|---|---|
| gtctcccagg ctggagtaca atggcatgat ctcagcttac tgcaacctcc gtctcctggg | 300 |
| ttcaagcgat tctcctgcct cagccttcca agtagctggg attacaggtg cccaccacca | 360 |
| cacctggcta ggttttgtat ttttagtaga gatggggttt ttttcatgtt ggccaggctg | 420 |
| atctggaact cctgacctca agtgatccac ctgccttggc ctcccaaagt gctgggattt | 480 |
| taggtgtgag ccacctcgcc tggcaaggga ttctgttctt agtccttgaa aaataaagt | 540 |
| tctgaatctt caaaaaaaaa aaaaaaaaaa aaaaaaaaaa aaaaaaaaaa aaaaaaaaaa | 600 |

<210> SEQ ID NO 18
<211> LENGTH: 600
<212> TYPE: DNA
<213> ORGANISM: Homo sapiens

<400> SEQUENCE: 18

| | |
|---|---|
| gtgtatcatg agccaaccct caaaggaccc gtattacagt gccacgttgg aaaacgctac | 60 |
| aggaagcatg acctatccac atctttccaa gatagacact aacatgtcat gtcccaaaca | 120 |
| ttagcacgtg ggggttgagc tctgtgcagt aatcgagatt gggagaattt gggcagcgcg | 180 |
| tgagaagtgc taagctactt gttttctcac ttgagcccgg gtaggctgtg ttggccctca | 240 |
| cttgggattc tcagcagtta catgaaagtt gtgctgataa tctcttctct tgtaccaatt | 300 |
| ttagtcaggc agaaaatggt aaacatgagg gtgctcttgt gacttaattt ttgttcaagg | 360 |
| gactaaattg cttatgttta ttccctgtca gcggagtgga gaatgtcatt catcaataaa | 420 |
| ccaaagccaa tagctggaga attgagatct ggttgaaagt ggtttatggt ttacatgctg | 480 |
| tactatcctg aggaattgcg agatattgct gaggggaaaa aaaaatgacc ttttcttgaa | 540 |
| atgtaacttg aaaacaaaat aaaatgtgga acataaaaaa aaaaaaaaaa aaaaaaaaaa | 600 |

<210> SEQ ID NO 19
<211> LENGTH: 600
<212> TYPE: DNA
<213> ORGANISM: Homo sapiens

<400> SEQUENCE: 19

| | |
|---|---|
| ccagaggcag aaggattggg actaggccaa catagagatt ggcgatggtt gtgagattct | 60 |
| aagagtgtgt gtgcatcttg acaatattag aggaggctga gcccaagcag gcacattctc | 120 |
| ttcgacccct ccctcattca gtctgctttg gagtctactg aacatcaagc ttgctatgag | 180 |
| caggatctta gagctgagga attggcctcc caatccgaac aggtgttata atcctttctt | 240 |
| aataggttgt gctgtggacc caatgtgagg gctgtgctgg tgtaaatggt gacatattga | 300 |
| gctgggggga tgctttcggg gtgggggac tggttccatt ccatcaaagg ccctcttgag | 360 |
| agtctatcca gggacccatt gttttacttt aacagaccag aaaagatgtt tgttttccat | 420 |
| gtcattaccc ccaggggata ccgaatgtgt gggtagaaat ttctctgtag attaaaaatc | 480 |
| agatttttac atggattcaa caaaggagcg tcacttggat ttttgttttc atccatgaat | 540 |
| gtagctgctt ctgtgtaaaa tgccattttg ctattaaaaa tcaattcacg ctggaaaaaa | 600 |

<210> SEQ ID NO 20
<211> LENGTH: 600
<212> TYPE: DNA
<213> ORGANISM: Homo sapiens

<400> SEQUENCE: 20

| | |
|---|---|
| gcacgtctac ggggctggac agagtgtggt taaccgggga actgggcaag ccggcgccga | 60 |
| gcctgcgtca gccgtgcaag ccgctccttc aggaacttcc gcttgtcgct ggtgtcgctc | 120 |

```
cgctccttca ggagccagct gtaggtgtcc ttgtcctgca ggagctgcag catggccttc      180
tgaagctgct ggccgtacgt ctggagcatg aagaactgga tgatcaaagg gatgtggctg      240
gagatgcgct tgctggcctc ctggtgatag ccatcaggt gctgaaagat ctcctccatg       300
gaagagtctg ttgccgagct ggactggaaa gccccaaaat cccaggattt cttcttcttt      360
tcttcttcca gctccttctc tctgaccttc tgcaatgcac ccctgtatac ctggtcctgg      420
cagtagacaa tctgttccat ctggaagtgg aggcggatca gcttctcacc ttctctctct      480
tgttctgctc taatgtcttc aattttggac ttggcggttc tgtggaggtt aaaaaactct      540
tcaaaatttt ttatcgccaa cttttttgta caaagttggc cttataaaga aagcattgct      600
```

<210> SEQ ID NO 21
<211> LENGTH: 600
<212> TYPE: DNA
<213> ORGANISM: Homo sapiens
<220> FEATURE:
<221> NAME/KEY: misc_feature
<222> LOCATION: (1)..(107)
<223> OTHER INFORMATION: n is a, c, g, or t

<400> SEQUENCE: 21

```
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnncca aatgagtgat     120
gcattgaccg ttcgtaattc ttggatgcaa aagtagaact caagctactt aataacaatc     180
atggtggcat gggcaccagc aagtcagggt ggacaacagc catagttctg gagcatggtc     240
ctcaagacta cctttttgtat gcagagtatt aacactttaa ctcttagatc cttggaacat     300
aaggaagaga ggctggaaca aaaaggggtt ggcatttgga ggtggagagg tagtgtaagg     360
cacaactgtt tatcaactgg tatctaagta tttcaggcca gacacgtggc tcacacctct     420
aatcccagca ctttgggagc tgagccagga ggattgcttg agtctaggag ttcaagaccg     480
gtctgggcaa catggtgaaa ccctgtctct acaaaaaaat acaaaaatta gccaggtgtg     540
gtggggcacg cctatggtcc cagctactgg ggaggctgag atgggaggat ccacctgagc     600
```

<210> SEQ ID NO 22
<211> LENGTH: 477
<212> TYPE: DNA
<213> ORGANISM: Homo sapiens

<400> SEQUENCE: 22

```
ttttttttaa ttaacttgac tttattgata gttacagcac aatttattaa ttaacttgac      60
tttattgata gttacagcac aatctgtcca aaaccaccag aatatacatt cttttcaaga     120
gctcaaatgg aacatttacc acaaaagacc atattctggg cttcaaaata agcctaaata     180
aatacaaaag catttaggac ctatgaatca gaagactgaa tatgcacata tacaaaatga     240
gaatcattct ctcacataca aaacttatat aggtagtaaa gatacagttg attaggtaga     300
tttgaatgtt gaatcactga catttcctga aggtagagct acaaattact ttttttaaaac     360 cactaaccca cccccacctt acctcactta ctctttttgg ccttaccacc tactttagtc     420
ataccctata catgttactc agaccaaatg gctctcataa acaatctcag tatatgt       477
```

<210> SEQ ID NO 23
<211> LENGTH: 600
<212> TYPE: DNA
<213> ORGANISM: Homo sapiens
<220> FEATURE:

```
<221> NAME/KEY: misc_feature
<222> LOCATION: (229)..(316)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t

<400> SEQUENCE: 23
ttaagaaggt atggaaagag tctgggagtg actaaactat ccaatgtcat tgaaataaag      60
caatgaagaa taagagtaat ttttgttgct ttattaaatt ttttctcaca gaattcttta     120
taaaaacacc atgtccctaa aatgtcattc aacatatatg cacaccttcg atgtatagga     180
cactgatcaa aaagacaga gaaatgtgtc cctggtgttt tgttttttgnn nnnnnnnnnn     240 nnnnnnnnnn nnnnnnnnnn nnnnnnnnnn nnnnnnnnnn nnnnnnnnnn nnnnnnnnnn     300
nnnnnnnnnn nnnnnnggga ctacaggcac ataccaccac acctggcttc atgttcccgg     360
tattagtaca atgccaaaat atttaaaatt cttaaaggtt aactcaaata tcttaagttt     420
tacttcactt acaatttcaa taatgctgaa attttgattg aatattgtgt ttgtagtgct     480
acctcttttt cgttcataag aacaaaagcc tatcattctc ttagtttcta aaaaatatat     540
gttcatatgg tttagataca tatataaata tntacacaaa acaatgtttt ttgagttgta     600

<210> SEQ ID NO 24
<211> LENGTH: 429
<212> TYPE: DNA
<213> ORGANISM: Homo sapiens

<400> SEQUENCE: 24
gcccgtgccg ccccagccgc tgccgcctgc accggacccg gagccgccat gcccaagtgt      60
cccaagtgca acaaggaggt gtacttcgcc gagagggtga cctctctggg caaggactgg     120
catcggccct gcctgaagtg cgagaaatgt gggaagacgc tgacctctgg ggccacgct      180 gagcacgaag gcaaacccta ctgcaaccac ccctgctacg cagccatgtt tgggcctaaa     240
ggctttgggc ggggcggagc cgagagccac actttcaagt aaaccaggtg gtggagaccc     300
catccttggc tgcttgcagg gccactgtcc aggcaaatgc caggccttgt ccccagatgc     360
ccagggctcc cttgttgccc ctaatgctct cagtaaacct gaacacttgg aaaaaaaaaa     420
aaaaaaaaa                                                            429

<210> SEQ ID NO 25
<211> LENGTH: 600
<212> TYPE: DNA
<213> ORGANISM: Homo sapiens

<400> SEQUENCE: 25
caaccaggaa gaaccgtacc agaaccactc cggccgattc gtctgcactg tacccggcta      60
ctactacttc accttccagg tgctgtccca gtgggaaatc tgcctgtcca tcgtctcctc     120
ctcaaggggc caggtccgac gctccctggg cttctgtgac accaccaaca aggggctctt     180
ccaggtggtg tcagggggca tggtgcttca gctgcagcag ggtgaccagg tctgggttga     240
aaaagacccc aaaagggtc acatttacca gggctctgag gccgacagcg tcttcagcgg     300
cttcctcatc ttcccatctg cctgagccag ggaaggaccc cctcccccac ccacctctct     360
ggcttccatg ctccgcctgt aaaatggggg cgctattgct tcagctgctg aagggagggg     420
gctggctctg agagccccag gactggctgc ccgtgacaca atgctctaag aagctcgttt     480
cttagacctc ttcctggaat aaacatctgt gtctgtgtct gctgaacatg agcttcagtt     540
```

```
gctactcgga gcattgagag ggaggcctaa gaataataac aatccagtgc ttaagagtca    600
```

<210> SEQ ID NO 26
<211> LENGTH: 600
<212> TYPE: DNA
<213> ORGANISM: Homo sapiens

<400> SEQUENCE: 26

```
gggtcgaccc ttgccactac acttcttaag gcgagcatca aaagccgggg aggttgatgt     60
tgaacagcac actttagcca agtatttgat ggagctgact ctcatcgact atgatatggt    120
gcattatcat ccttctaagg tagcagcagc tgcttcctgc ttgtctcaga aggttctagg    180
acaaggaaaa tggaacttaa agcagcagta ttacacagga tacacagaga atgaagtatt    240
ggaagtcatg cagcacatgg ccaagaatgt ggtgaaagta aatgaaaact taactaaatt    300
catcgccatc aagaataagt atgcaagcag caaactcctg aagatcagca tgatccctca    360
gctgaactca aaagccgtca agaccttgc ctccccactg ataggaaggt cctaggctgc     420
cgtgggccct ggggatgtgt gcttcattgt gcccttttc ttattggttt agaactcttg     480
attttgtaca tagtcctctg gtctatctca tgaaacctct tctcagacca gttttctaaa    540
catatattga ggaaaaataa agcgattggt ttttcttaag gtaaaaaaaa aaaaaaaaa     600
```

<210> SEQ ID NO 27
<211> LENGTH: 600
<212> TYPE: DNA
<213> ORGANISM: Homo sapiens

<400> SEQUENCE: 27

```
cagaaaggcc cgcccctccc cagacctcga gttcagccaa aacctcccca tggggcagca     60
gaaaactcat tgtcccttc ctctaattaa aaaagataga aactgtcttt ttcaataaaa     120
agcactgtgg atttctgccc tcctgatgtg catatccgta cttccatgag gtgttttctg    180
tgtgcagaac attgtcacct cctgaggctg tgggccacag ccacctctgc atcttcgaac    240
tcagccatgt ggtcaacatc tggagttttt ggtctcctca gagagctcca tcacaccagt    300
aaggagaagc aatataagtg tgattgcaag aatggtagag gaccgagcac agaaatctta    360
gagatttctt gtcccctctc aggtcatgtg tagatgcgat aaatcaagtg attggtgtgc    420
ctgggtctca ctacaagcag cctatctgct taagagactc tggagtttct tatgtgccct    480
ggtggacact tgcccaccat cctgtgagta aaagtgaaat aaaagctttg actagaaaaa    540
aaaaaaaaaa aaaaaaaaa aaaaaaaaa aaaaaaaaa aaaaaaaaaa aaaaaaaaaa      600
```

<210> SEQ ID NO 28
<211> LENGTH: 600
<212> TYPE: DNA
<213> ORGANISM: Homo sapiens
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t

<400> SEQUENCE: 28

```
tcagcactga gtgttcaaag acagtaggac gtcggttgct gacctgcctc ttagaagcta     60
gtttaactca gcgggtaagg atctaggact tctacattag ttaccactgt aatgataaca    120
```

```
ccaccagaaa agtctgtagt ttaatatttc ccaccttatg cctgtttctt cattcacgca    180
aagaaaataa aaatataata cctaagcctc tttgtattac ataaagcaaa atgcaaagca    240
ctgtatcttc caaatacttc ctcttgatat ggtggaatta tagagtagta tcatttgtaa    300
cntgaaatgt cttctagggt tgctatgcga aagcaagact gtggtttcat tccaatttcc    360
tgtatatcgg aatcatcacc atctgtgtat gtgtgattga ggtgttgggg atgtcctttg    420
cactgaccct gaactgccag attgacaaaa ccagccagac catagggcta tgatctgcag    480
tagtcctgtg gtgaagagac ttgtttcatc tccgggaaat gcaaaaccat ttataggcat    540
gaagccctac atgatcactt gcagggtgan cctcctccca tccttttccc ttttagggtc    600
```

<210> SEQ ID NO 29
<211> LENGTH: 600
<212> TYPE: DNA
<213> ORGANISM: Homo sapiens

<400> SEQUENCE: 29

```
gcctgggacg ctgctgctgt tcaggaaacg atggcagaac gagaagctcg ggttggatgc     60
cggggatgaa tatgaagatg aaaaccttta tgaaggcctg aacctggacg actgctccat    120
gtatgaggac atctcccggg gcctccaggg cacctaccag gatgtgggca gcctcaacat    180
aggagatgtc cagctggaga agccgtgaca cccctactcc tgccaggctg ccccgcctg     240 ctgtgcaccc agtccagtg tctcagctca cttccctggg acattctcct ttcagccctt    300
ctgggggctt ccttagtcat attccccag tggggggtgg gagggtaacc tcactcttct    360
ccaggccagg cctccttgga ctcccctggg ggtgtcccac tcttcttccc tctaaactgc    420
cccacctcct aacctaatcc ccccgccccg ctgcctttcc caggctcccc tcaccccagc    480
gggtaatgag cccttaatcg ctgcctctag gggagctgat tgtagcagcc tcgttagtgt    540
caccccctcc tccctgatct gtcagggcca cttagtgata ataaattctt cccaactgca    600
```

<210> SEQ ID NO 30
<211> LENGTH: 600
<212> TYPE: DNA
<213> ORGANISM: Homo sapiens

<400> SEQUENCE: 30

```
ggattcagcc agtgcggatt ttccatataa tccaggacaa ggccaagcta taagaaatgg     60
agtcaacaga aactcggcta tcattggagg cgtcattgct gtggtgattt tcaccatcct    120
gtgcaccctg gtcttcctga tccggtacat gttccgccac aagggcacct accataccaa    180
cgaagcaaag ggggcggagt cggcagagag cgcggacgcc gccatcatga caacgaccc     240 caacttcaca gagaccattg atgaaagcaa aaggaatgg ctcatttgag gggtggctac    300
ttggctatgg gataggagg agggaattac tagggaggag agaaagggac aaaagcaccc    360
tgcttcatac tcttgagcac atccttaaaa tatcagcaca agttggggga ggcaggcaat    420
ggaatataat ggaatattct tgagactgat cacaaaaaaa aaaaccttt ttaatatttc     480 tttatagctg agttttccct tctgtatcaa aacaaaataa tacaaaaaat gcttttagag    540
tttaagcaat ggttgaaatt tgtaggtaat atctgtctta ttttgtgtgt gtttagaggt    600
```

<210> SEQ ID NO 31
<211> LENGTH: 600
<212> TYPE: DNA
<213> ORGANISM: Homo sapiens

<400> SEQUENCE: 31

```
atgtccaaaa agatacagaa gaactaaaga gctgtggtat acaagacata tttgttttct      60
gcaccagagg ggaactgtca aaatatagag tcccaaacct tctggatctc taccagcaat     120
gtggaattat cacccatcat catccaatcg cagatggagg gactcctgac atagccagct     180
gctgtgaaat aatggaagag cttacaacct gccttaaaaa ttaccgaaaa accttaatac     240
actgctatgg aggacttggg agatcttgtc ttgtagctgc ttgtctccta ctatacctgt     300
ctgacacaat atcaccagag caagcccatag acagcctgcg agacctaaga ggatccgggg    360
caatacagac catcaagcaa tacaattatc ttcatgagtt tcgggacaaa ttagctgcac     420
atctatcatc aagagattca caatcaagat ctgtatcaag ataaaggaat tcaaatagca     480
tatatatgac catgtctgaa atgtcagttc tctagcataa tttgtattga aatgaaacca     540
ccagtgttat caacttgaat gtaaatgtac atgtgcagat attcctaaag ttttattgac     600
```

<210> SEQ ID NO 32
<211> LENGTH: 600
<212> TYPE: DNA
<213> ORGANISM: Homo sapiens

<400> SEQUENCE: 32

```
ggtttccttc ccaggacagc tgcagggtag agatcatttt aagtgcttgt ggagttgaca      60
tccctattga ctcttcccca gctgatatca gagacttaga cccagcactc cttggattag     120
ctctgcagag tgtcttggtt gagagaataa cctcatagta ccaacatgac atgtgacttg     180
gaaagagact agaggccaca cttgataaat catggggcac agatatgttc cacccaaca     240 aatgtgataa gtgattgtgc agccagagcc agccttcctt caatcaaggt ttccaggcag     300
agcaaatacc ctagagattc tctgtgtatat aggaaatttg gatcaaggaa gctaaaagaa    360
ttacagggat gttttaatc ccactatgga ctcagtctcc tggaaatagg tctgtccact      420
cctggtcatt ggtggatgtt aaacccatat tcctttcaac tgctgcctgc tagggaaaac     480
tgctcctcat tatcatcact attattgctc accactgtat cccctctact tggcaagtgg     540
ttgtcaagtt ctagttgttc aataaatgtg ttaataatgc ttaaaaaaaa aaaaaaaaa      600
```

<210> SEQ ID NO 33
<211> LENGTH: 600
<212> TYPE: DNA
<213> ORGANISM: Homo sapiens

<400> SEQUENCE: 33

```
attccaggaa gcatgggatt ttatttgct tgattttggg cacatgaaat aatagctcta       60
ggaaaatgcg catcttaatg actctttgta aagagaggca tttcttacaa ctgtgatgtt     120
tgcttacata aaagttacct cataagttaa ttctaacttt tattcttgaa tttatttca     180 tttcaatagc ttgtttcatt tgcacgcctt tgtatttga ttgacctgta gaatggatgt      240
taggaaactc aaaattgaac acagtgaaac aaatggtatt tgaagaaatg taatatcttt     300
tatattctat ttatgatatc cataatcaaa tgagattatt ttaccacata aatgttttaa     360
atatcagatt tttagtttgc agtttagga aatgcttta gatagaaaag gttcttatgc       420 attgaattg gagtactacc aacaatgaat gaatttattt tttatattct tacacatttt     480
attggtcatt gtcacagata gtaaatacta aaaatttcag gtcagtttgt tttgaaactg     540
aaattggaaa taaatctgga aatgttttgt tgcactaaaa taataaaatg aattgtactg     600
```

<210> SEQ ID NO 34

```
<211> LENGTH: 600
<212> TYPE: DNA
<213> ORGANISM: Homo sapiens

<400> SEQUENCE: 34
taggccagcc ctgtcaccac ctccactgcc atgaccaggc cgaaggcagg gaacgccctc      60
cccagtcccg ctgtccagca aggccccgag acttttcttc tgtgatttcc aaaagcaagg     120
cagccgtgct gttctagttc ctctccatcc gccacctccc ctcccgctgc cccagaagtt     180
tctatcattc catggagaaa gctgtgttcc aatgaatcct acctcttgcc cagtcccagg     240
cagagtaagc agggcccacc tagggaccaa gaaagagtag gaagaagggg acgagccggg     300
agcaaaacca cctcagacac ccgggccttc tcagccttct ccccgcggcc agctgggtct     360
ccggggaccc tgggccctgg gccgcccatt cctggccctc ccgctgcatc tcagacctga     420
cacccaacgg ggggatgtgg tggcctgtgc ccaccttctc tccctcctcc cgacccgccc     480
cctcgccccc acccctgtgt gtttcgccag ttaagcacct gtgactccag tacctactac     540
tggttttggg ttggttgttc tgtctttttt ttaattaaat aaaaacattt ttaaaatgtt     600

<210> SEQ ID NO 35
<211> LENGTH: 600
<212> TYPE: DNA
<213> ORGANISM: Homo sapiens

<400> SEQUENCE: 35
tgctcagacc agctcttccg aaaaccaggc cttatctcca agaccagaga tagtggggag      60
acttcttggc ttggtgagga aaagcggaca tcagctggtc aaacaaactc tctgaacccc     120
tccctccatc gttttcttca ctgtcctcca agccagcggg aatggcagct gccacgccgc     180
cctaaaagca cactcatccc ctcacttgcc gcgtcgccct cccaggctct caacaggggga     240 gagtgtggtg tttcctgcag gccaggccag ctgcctccgc gtgatcaaag ccacactctg     300
ggctccagag tggggatgac atgcactcag ctccttggctc cactgggatg ggaggagagg     360
acaagggaaa tgtcaggggc ggggagggtg acagtggccg cccaaggccc acgagcttgt     420
tctttgttct ttgtcacagg gactgaaaac ctctcctcat gttctgcttt cgattcgtta     480
agagagcaac attttacccca cacacagata aagttttccc ttgaggaaac aacagcttta     540
aaagaaaaag aaaaaaaaag tctttggtaa atggcaaaaa aaaaaaaaaa aaaaaaaaa     600

<210> SEQ ID NO 36
<211> LENGTH: 600
<212> TYPE: DNA
<213> ORGANISM: Homo sapiens

<400> SEQUENCE: 36
tccccagaca ccgccacatg gcttcctcct gcgtgcatgt gcgcacacac acacacacac      60
gcacacacac acacacacac tcactgcgga gaaccttgtg cctggctcag agccagtctt     120
tttggtgagg gtaaccccaa acctccaaaa ctcctgcccc tgttctcttc cactctcctt     180
gctacccaga aatcatctaa atacctgccc tgacatgcac acctcccctg cccaccagc     240 ccactggcca tctccacccg gagctgctgt gtcctctgga tctgctcgtc atttttcctt c     300 ccttctccat ctctctggcc ctctacccct gatctgacat cccactcac gaatattatg     360 cccagtttct gcctctgagg gaaagcccag aaaaggacag aaacgaagta gaaaggggcc     420
cagtcctggc ctggcttctc ctttggaagt gaggcattgc acgggagac gtacgtatca     480 gcggcccctt gactctgggg actccggggtt tgagatggac acactggtgt ggattaacct     540
```

```
gccagggaga cagagctcac aataaaaatg gctcagatgc cacttcaaag aaaaaaaaaa    600
```

<210> SEQ ID NO 37
<211> LENGTH: 420
<212> TYPE: DNA
<213> ORGANISM: Homo sapiens

<400> SEQUENCE: 37

```
gggcggttct ccaagcaccc agcatcctgc tagacgcgcc gcgcaccgac ggaggggaca     60
tgggcagagc aatggtggcc aggctcgggc tggggctgct gctgctggca ctgctcctac    120
ccacgcagat ttattccagt gaaacaacaa ctggaacttc aagtaactcc tcccagagta    180
cttccaactc tgggttggcc ccaaatccaa ctaatgccac caccaaggtg gctggtggtg    240
ccctgcagtc aacagccagt ctcttcgtgg tctcactctc tcttctgcat ctctactctt    300
aagagactca ggccaagaaa cgtcttctaa atttccccat cttctaaacc caatccaaat    360
ggcgtctgga agtccaatgt ggcaaggaaa acaggtctt catcgaatct actaattcca     420
```

<210> SEQ ID NO 38
<211> LENGTH: 600
<212> TYPE: DNA
<213> ORGANISM: Homo sapiens
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (514)..(515)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
<220> FEATURE:
<221> NAME/KEY: misc_feature
<222> LOCATION: (523)..(524)
<223> OTHER INFORMATION: n is a, c, g, or t
<220> FEATURE:
<221> NAME/KEY: misc_feature
<222> LOCATION: (526)..(527)
<223> OTHER INFORMATION: n is a, c, g, or t
<220> FEATURE:
<221> NAME/KEY: misc_feature
<222> LOCATION: (583)..(585)
<223> OTHER INFORMATION: n is a, c, g, or t

<400> SEQUENCE: 38

```
accctgtgcc agaaaagcct cattcgttgt gcttgaaccc ttgaatgcca ccagctgtca     60
tcactacaca gccctcctaa gaggcttcct ggaggtttcg agattcagat gccctgggag    120
atcccagagt ttcctttccc tcttggccat attctggtgt caatgacaag gagtaccttg    180
gctttgncac atgtcaaggc tgaagaaaca gtgtctccaa cagagctcct tgtgttatct    240
gtttgtacat gtgcatttgt acagtaattg gtgtgacagt gttctttgtg tgaattacag    300
gcaagaattg tggctgagca aggcacatag tctactcagt ctattcctaa gtcctaactc    360
ctccttgtgg tgttggattt gtaaggcact ttatccccttt tgtctcatgt ttcatcgtaa    420
atggcatagg cagagatgat acctaattct gcatttgatt gtcactttttt gtacctgcat    480 taatttaata aaatattctt atttattttg ttanntngta nannannatg tccatttct     540
``` tgtttattt gtgtttaata aaatgttcag tttaacatcc cannngagaa agttaaaaaa    600

<210> SEQ ID NO 39
<211> LENGTH: 523
<212> TYPE: DNA
<213> ORGANISM: Homo sapiens

<400> SEQUENCE: 39
ctcctggttc aaaagcagct aaaccaaaag aagcctccag acagccctga gatcacctaa    60
aaagctgcta ccaagacagc cacgaagatc ctaccaaaat gaagcgcttc ctcttcctcc    120
tactcaccat cagcctcctg gttatggtac agatacaaac tggactctca ggacaaaacg    180
acaccagcca aaccagcagc ccctcagcat ccagcaacat aagcggaggc atttttcttt    240
tcttcgtggc caatgccata atccacctct tctgcttcag ttgaggtgac acgtctcagc    300
cttagccctg tgcccctga aacagctgcc accatcactc gcaagagaat cccctccatc    360
tttgggaggg gttgatgcca gacatcacca ggttgtagaa gttgacaggc agtgccatgg    420
gggcaacagc caaaataggg gggtaatgat gtaggggcca agcagtgccc agctgggggt    480
caataaagtt acccttgtac ttgcaaaaaa aaaaaaaaaa aaa                      523

<210> SEQ ID NO 40
<211> LENGTH: 600
<212> TYPE: DNA
<213> ORGANISM: Homo sapiens

<400> SEQUENCE: 40
gccatcaaga atttactgaa agcagttagc aaggaaaggt ctaaaagatc tccttaaaac    60
cagaggggag caaaatcgat gcagtgcttc caaggatgga ccacacagag gctgcctctc    120
ccatcacttc cctacatgga gtatatgtca agccataatt gttcttagtt tgcagttaca    180
ctaaaaggtg accaatcatg gtcaccaaat cagctgctac tactcctgta ggaaggttaa    240
tgttcatcat cctaagctat tcagtaataa ctctaccctg gcactataat gtaagctcta    300
ctgaggtgct atgttcttag tggatgttct gaccctgctt caaatatttc cctcaccttt    360
cccatcttcc aagggtataa ggaatctttc tgctttgggg tttatcagaa ttctcagaat    420
ctcaaataac taaaggtat gcaatcaaat ctgcttttta aagaatgctc tttacttcat    480
ggacttccac tgccatcctc ccaagggcc caaattcttt cagtggctac ctacatacaa    540
ttccaaacac atacaggaag gtagaaatat ctgaaaatgt atgtgtaagt attcttattt    600

<210> SEQ ID NO 41
<211> LENGTH: 513
<212> TYPE: DNA
<213> ORGANISM: Homo sapiens

<400> SEQUENCE: 41
gggaaatcag tgaatgaagc ctcctatgat ggcaaataca gctcctattg ataggacata    60
gtggaagtgg gctacaacgt agtacgtgtc gtgtagtacg atgtctagtg atgagtttgc    120
taatacaatg ccagtcaggc cacctacggt gaaaagaaag atgaatccta gggctcagag    180
cactgcagca gatcatttca tattgcttcc gtggagtgtg gcgagtcagc taatggcag    240
gggcagcaag atggtgttgc agacccaggt cttcatttct ctgttgctct ggatctctgg    300
tgcctacggg gacatcgtga tgacccagtc tccagactcc ctggctgtgt ctctgggcga    360
gagggccacc atcaagtgca agtccagcca gagtatttta tataggtcca acaacaagaa    420
ctacttagct tggtaccagc agaaagcagg acagcctcct aaattgttca tttactgggc    480
atctacccgg gaatccgggg tccctgaccg att                              513

<210> SEQ ID NO 42
<211> LENGTH: 600
<212> TYPE: DNA
<213> ORGANISM: Homo sapiens

<400> SEQUENCE: 42
aacgaaagtc tagcctttcg tacccgtata tataaagaca cccctgttct gattggacaa     60
ggcagccttt cccctgcagc tcgattggtg gagacgccca ctccctgaca gaacatctcc    120
tgcatgtaga ccaaatatta aactttcct ccgtccatct ttaactgctg gtgttttcaa     180
ccctttcccc tctgtgccat gtttctagct tttatttaaa acgtactttg gttttccttg    240
gcaaaattgt gtctagctac taggatgacg tgtcttaatt tttttttaaa tgttggcgct    300
gaaactggct tgatcaacg ttttaaaaag acgcgcgcta gttgtgattg gccaagtgat     360
ttcttcttac cctcttaagt ttagaaaggt taatttcata tcttgatttg tctatttaaa    420
cttggagata ttttcaataa tttgttccaa atgcaccatg actattaact cataagtaac    480
aatatgaaac ctgatgttaa gctacatgaa cacatttaat ttcaccacaa tatgacatcc    540
tcatatgaaa gcactctctt atcttttaca agttcaactg gtatttgtgt aatctgctgt    600

<210> SEQ ID NO 43
<211> LENGTH: 600
<212> TYPE: DNA
<213> ORGANISM: Homo sapiens
<220> FEATURE:
<221> NAME/KEY: misc_feature
<222> LOCATION: (102)..(104)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (389)..(390)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (439)..(439)

```
<223> OTHER INFORMATION: n is a, c, g, or t
<220> FEATURE:
<221> NAME/KEY: misc_feature
<222> LOCATION: (441)..(442)
<223> OTHER INFORMATION: n is a, c, g, or t
<220> FEATURE:
<221> NAME/KEY: misc_feature
<222> LOCATION: (444)..(445)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t

<400> SEQUENCE: 43
tgctaccatg cctgactagt ttttgtattt ttagtagaga cagggtttga ccatattggc    60
caggttggtc ttggactcct gacaagtgat ccgccctcct cnnncncncg aagtgctagg   120
gttacnaggt gtgaaccacc atgcctaact atcgttgcta ctttctattg gaagagaagg   180
cagccctgat ttagtctgtt tacagtctgc attatgtgga gaatagagag ccatcatagt   240
ccctaaaact ttccttgcca gttaacccag caggacaacc tgtctttgtc tcttgacaac   300
tgttaactga gaacagggcc cttgctcctc taggtgtgca cattaaggac tttgcacagt   360
gtggatgtag ctcatgctgc tctgccntnn agtacatgct gcttgaattt tcatcatnan   420
cctccacncc ttncacctnc nngnnaaaaa aaaagcgtgc aggaagtagc atttcagatc   480
cttctccacc acctctgctt cccttctccc ttcttttcct ccttgcagca ttccctttag   540
tacnagggag ggatggtggt tgaaaatggg gggaatgatg ttgctcagaa aaaaaaaaa    600

<210> SEQ ID NO 44
<211> LENGTH: 600
<212> TYPE: DNA
<213> ORGANISM: Homo sapiens
<220> FEATURE:
<221> NAME/KEY: misc_feature
<222> LOCATION: (166)..(166)
<223> OTHER INFORMATION: n is a, c, g, or t

<400> SEQUENCE: 44
ataatgctgg aaacagaagc accaaactga ttgtgcaatt actccttttg tagaagaggc    60
caaaatcctc ctcctccttc ctttctccta tattcactcc tccaggatca taaagcctcc   120
ctcttgttta tctgtgtctg tctgtctgat tggttagatt tggctncect tccaagctaa   180 tggtgtcagg tggagaacag agcaaccttc cctcggaagg agacaattcg aggtgctggt   240
acatttccct tgttttctat gttcttcttt ctagtgggtc tcatgtagag atagagatat   300
ttttttgttt tagagattcc aaagtatata tttttagtgt aagaaatgta ccctctccac   360
actccatgat gtaaatagaa ccaggaataa atgtgtcatt gtgataatcc catagcaatt   420
tatggtaaga acaagacccc tttccctcac caccgagtct cgtggtctgt gtctgtgaac   480
cagggcaggt aattgtgaca ctgcatctca tagaactctg cctgcccaga tttttgtgtg   540
ctcacctcaa tgggtgaaaa ataaagtctg tgtaaactgt taaaaaaaaa aaaaaaaaaa   600

<210> SEQ ID NO 45
<211> LENGTH: 497
<212> TYPE: DNA
<213> ORGANISM: Homo sapiens
<220> FEATURE:
<221> NAME/KEY: misc_feature
<222> LOCATION: (383)..(384)
<223> OTHER INFORMATION: n is a, c, g, or t
<220> FEATURE:
<221> NAME/KEY: misc_feature
```

```
<222> LOCATION: (464)..(466)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t

<400> SEQUENCE: 45
tcctcagacc cagtaattcc acccctagga atccagctta cacacacaag aaagaaaaga    60
taaatgtaca aggttagtca ctgcacagtg agacagcaaa agattagaaa gaacccaagt   120
gattattgat ctgggtttta ttcctttata gcccaaccat atgatggaat actataatgt   180
tgtaaaaatg ggttaagagt tctttatgaa ttggtgtgga acatcgcca agatatgaaa    240 gccaaatgca gaaaaatata tgtggtatgc tattatctat gtgaaaaaga cattactatt   300
ctctggaagg ataaacacaa atttgagaat ggtggatatc tggggtgaga ggtatccttt   360
tcactgttct ttaaaagttt tgnnattttg gtgtttgcct attcaaaaaa atggttaaaa   420
tcagttgcca ccaattaaaa attaggagaa tgcatataaa gaannnaant tcctgttaaa   480
aaaaaaaaaa aaaaaaa                                                 497

<210> SEQ ID NO 46
<211> LENGTH: 600
<212> TYPE: DNA
<213> ORGANISM: Homo sapiens

<400> SEQUENCE: 46
gcccatagtc ccatcttttt acaggcattt tttacacctg gagcagccag aggacgcatg    60
catggctctt cggaaggtaa tttagggatc acccatgtaa gtttcctaag gatttcttta   120
acatggttct tctgattcag tccggccaat taaatctaaa tccacccctg aaagccatct   180
ggtgtggata acaagcccac aaatgagcag tcagcttttt gtgcccttta gggcctggga   240
caaccacggg atctaaaagg ggctggaact agaggtcttg agctcctgtt cctaaaatca   300
tcttcatcct atatctgcag ccttctcctg ccacggcatg cacccacaca tgcgagcctc   360
ccgggtactg tcatcctgaa ttctgagacc atccagcact tcctttagtt ttgccctggt   420
gctgttgact tttgtttact gaagagtgtg ctggaggcag acaagggac atggaaggct    480 gcaatttaag agtctaaaag gttttagaat cctgaaggag gtttaacaag ctgaattgaa   540
gaataatacc tttctcaact ggagagaatt tacatgattg cattattgtt aaaattaaca   600

<210> SEQ ID NO 47
<211> LENGTH: 600
<212> TYPE: DNA
<213> ORGANISM: Homo sapiens

<400> SEQUENCE: 47
atcatttagt tgaatcatta taagtctagg actgtctgta gatgtaaatt tgttaagaat    60
taggactcaa gagtagaatt cctttaatcc acatagactt acaatggtgc tgtgcacatg   120
gagcccctaa atcattgctg actgagtaga tttcccaggg taagcccaag aagttactcc   180 tagaagggc tggtagggga aagagccaac atcccacatg cctgcccact ttgggtctgg    240
tcccaagaaa caaactccag tggcctcgaa aatttaatat tgctgtcaga agggcctccc   300
cttcaaagga acaggtcctg atagctcttg ttatatgcaa agtggaaagg taacgtgact   360
gttctctgca tttcctgcct ttcaattgag tgaagacaga cagatgattt attgggcatt   420
tcctagcctc cccttcacca taggaaacca gactgaaaaa aaggtgcaaa ttttaaaaag   480
```

```
atgtgtgagt atcttgaggg ggctggggga gaattcctgt gtaccactaa agcaaaaaaa      540
gaaaactctc taacagcagg acctctgatc tggaggcata ttgaccataa atttacgcca      600

<210> SEQ ID NO 48
<211> LENGTH: 491
<212> TYPE: DNA
<213> ORGANISM: Homo sapiens

<400> SEQUENCE: 48
tttttctgag caacatcatt cccccatttt tcaaccacca tccctccctg gtactaaagg       60
gaatgctgca aggaggaaaa gaagggagaa gggaagcaga ggtggtggag aaggatctga      120
aatgctactt cctgcacgct tttttcttc ttggaggtgg aaggagtgga ggatgatgat      180
gaaaattcaa gcagcatgta ctagacggca gagcagcatg agctacatcc acactgtgca      240
aagtccttaa tgtgcacacc tagaggagca agggccctgt tctcagttaa cagttgtcaa      300
gagacaaaga caggttgtcc tgctgggtta actggcaagg aaagttttag ggactatgat      360
ggctctctat tctccacata atgcagactg taaacagact aaatcagggc tgccttctct      420
tccaatagaa agtagcaacg atagttaggc atggtggttc acaccttgta accctagcac      480
ttcgtgggca g                                                           491

<210> SEQ ID NO 49
<211> LENGTH: 600
<212> TYPE: DNA
<213> ORGANISM: Homo sapiens

<400> SEQUENCE: 49
atcagaacaa tttcatgtta tacaaataac atcagaaaaa tatcttaaat tatatggcat       60
attctattga ttcatccaca aatttataag tccttaccac cttcattat attggtacta      120 ggcattatag tagtgctagg cactatagta atgctggggt ataaacaaga ataaaacaaa      180
ataagttcct tatttcaggt aacttacagt ataggtcagt ggttcttagc ttgctttta      240 attatgaatt cctttgaaag tctagtaaaa taatccaaca ccattattcc ccattgcaca      300
tacccccaga tgttttagac atattttcaa ttgctccatg gaccttaaga aaacttggtt      360
ggtgtgcagt ttggtgtatt atgggtaaga ctggacctgg tgttagaaaa tctgcatttg      420
aggctttgtt ctgacagtgt ctagtgtaaa catgggcaga ccacttaaac ctctcttag       480 tcttctctgt agaatgatga taataccatc taattagcag gattgttgtt ttattcagtg      540
agacagcata tgtaaataac ttagtaaaat aaaaagcaac gtgtttataa tggtaaaaaa      600

<210> SEQ ID NO 50
<211> LENGTH: 600
<212> TYPE: DNA
<213> ORGANISM: Homo sapiens

<400> SEQUENCE: 50
tgggaatcat gaactccttc gtcaacgaca tcttcgaacg catcgcgggt gaggcttccc       60
gcctggcgca ttacaacaag cgctcgacca tcacctccag ggagatccag acggccgtgc      120
gcctgctgct gccgggggag ttggccaagc acgccgtgtc cgaggcacc aaggccgtca      180 ccaagtacac cagcgctaag taaacttgcc aaggagggac tttctctgga atttcctgat      240
atgaccaaga aagcttctta tcaaaagaag cacaattgcc ttcggttacc tcattatcta      300
ctgcagaaaa gaagacgaga atgcaaccat acctagatgg acttttccac aagctaaagc      360
tggcctcttg atctcattca gattccaaag agaatcattt acaagttaat ttctgtctcc      420
```
ttggtccatt ccttctctct aataatcatt tactgttcct caaagaattg tctacattac    480
ccatctcctc ttttgcctct gagaaagagt atataagctt ctgtacccca ctgggggtt    540 ggggtaatat tctgtggtcc tcagccctgt accttaataa atttgtatgc cttttctctt    600

<210> SEQ ID NO 51
<211> LENGTH: 600
<212> TYPE: DNA
<213> ORGANISM: Homo sapiens
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (141)..(141)

<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t

<400> SEQUENCE: 51

| | | | | | |
|---|---|---|---|---|---|
| gaaagtgata | atacagaaag | gtggggctgg | tgtagggntn | aagncaggat | gctttggnan | 60 |
| agcatgnaag | gtcnccgant | ccagtgntna | ggaactaatg | angggttttnt | naagancgtn | 120 |
| atgagatcaa | tgcngatgag | ncacttagaa | gnagcaatta | gttaggcaaa | gggaagtgaa | 180 |
| tgtgnaggag | gaacaagcat | tccaggcaag | aagaacaccc | tatcgaaaag | cctggaagca | 240 |
| aaacattagt | gaggctacct | ttcataaatt | gctttctgta | agtcatgcca | ttgtgtagtc | 300 |
| ttaattgctt | tctctcacca | gggaaggtgt | gggaaggact | tgtgaaatac | atattcgagg | 360 |
| aaaaactatg | cacaaggccg | tgcatttaaa | aataaactcc | ctaaggctgg | ggtgaaacct | 420 |
| gctacggtct | gcgcaagttg | actgttaatg | aatttgattc | tcaggtgtga | gtgattaaaa | 480 |
| gaacactgat | catgtcattt | tcttttttggt | cactaattcc | ctccctccct | tctctttctt | 540 |
| ttcttttttc | ttttctttttc | ttttctttc | tttcttcccg | acagagaaag | actccatctc | 600 |

<210> SEQ ID NO 52
<211> LENGTH: 600
<212> TYPE: DNA
<213> ORGANISM: Homo sapiens

<400> SEQUENCE: 52

| | | | | | |
|---|---|---|---|---|---|
| taagatgttt | aagtatatcc | aaccgtccca | gaccacattg | gcctatttcc | tcctcttggc | 60 |
| aacactgctc | gggttttccc | ctcgcatcat | ccttatgcta | tgacactgga | ctaaattgta | 120 |
| ataatacatt | ttcttgttaa | tctcctcatt | atactatgag | ctccttgagg | acaggtactt | 180 |
| tgtcttgctc | acatctgtag | attcaatgcc | tggcacagcg | attgatattg | caagggcact | 240 |
| taataaatgg | ttttgaata | aaagaattgc | ttaaagtaaa | atatagctgt | aaattgtatt | 300 |
| ataaaaggac | agtgggtggc | agtctgaggt | ctgctattta | ctggtttggg | caagttactt | 360 |
| aatctgtttg | cttcctcagc | tgtacgatgg | gtaaaataat | agtggttatc | acaacagggt | 420 |
| ggttacagcg | atgaaatgag | attatgtgtg | taggctacca | cataattgta | aagctgatat | 480 |
| ttaaatggaa | cagatactgc | acagacactt | gaggtctgag | aataagatta | ggtcaaccag | 540 |
| agtattaatg | ggttaaataa | aggtgacatc | ctatgcaacc | aacggtttga | tctttatgct | 600 |

<210> SEQ ID NO 53
<211> LENGTH: 600
<212> TYPE: DNA
<213> ORGANISM: Homo sapiens

<400> SEQUENCE: 53

| | | | | | |
|---|---|---|---|---|---|
| gtcttccagt | cagtcagtgt | cttccagaaa | aatctacgtc | ttccaccaaa | tccaggtctt | 60 |
| ccagtcaatc | cacatcttcc | ggaaaaaatc | caggtcttcc | agccaatata | tgtcttcctg | 120 |
| aagatccacg | tcttccagaa | aatccatgtc | ttccagaaaa | tccatgtctt | ccagtaacct | 180 |
| cccagtcttc | cagaaaatcc | acgtcttccc | aacaatccaa | gtcttccgga | taatttgggt | 240 |
| cttcctgaaa | atctacgtct | tccaaaaaag | ccatgtcttc | cagaaaatcc | acatcttcca | 300 |
| atggcctcca | ggtcttccag | actatccatg | tcttccagaa | aatccttgtc | ttcccttaaa | 360 |

```
tctatagctt ccaaaaaatc cgggtcttcc aggaaatccg tgtcttccag caagtccacg    420
tcttccaaca aagccatgtc ttccagacta tccatgtctt ccagaaaatc cttgtcttcc    480
ctcaaatcca tagcttccga aaaatccagg tcttccagga atccgtgtc ttccagcaaa     540 tccacgtctt ccaacaaagc catgtcttcc atcaaattaa tgtcttccag cctacttgtg    600

<210> SEQ ID NO 54
<211> LENGTH: 600
<212> TYPE: DNA
<213> ORGANISM: Homo sapiens

<400> SEQUENCE: 54
agcatcgttt atgaaaacaa ctaaatattc actaatggtg ccagtggaat aaatcagaga    60 acatccctg ctacgtaact ctctgcatac atcaaagaga atggtgtggc tttgcttttt    120
caacaatcta ctgagtggcc atgggcatgt ggatatggcc atgaatgagc aagatcctct    180
ctgatcctgt agaagttaag ttctaccaga taacttgctg cttcaacaaa aagatttacc    240
tttttaaata aatgttgtag aatacttaaa aaaacaaac tagaatttgc ctgtgtgcag     300
ccagtaacat gtctatttaa cctggacacc ttttgaggaa tattctcaga ttgcccccat    360
gctgtttata agacattgtt ccttatacac ctgtttatga atgaaaagaa acataaggag    420
tgggtacaaa gacttctatc tatgaatgat taaaaaggct agagtacgaa acttcttga    480 acctttggta ctaaatgctt ttcatgttct atataaatgt agaaaacatt ttacaaatcc    540
tgtaaataaa ctgtttattt tttatagaaa gccaaaaaaa aaaaaaaaaa aaaaaaaaa    600

<210> SEQ ID NO 55
<211> LENGTH: 600
<212> TYPE: DNA
<213> ORGANISM: Homo sapiens

<400> SEQUENCE: 55
tctttcaaca tttagatagt ctttcttaat atttccagga gagtacctca ttttttatttt   60 gaaaaccatt cagcacattt atcttatgta acatgcagag catatatcta tctgtatttt   120 taaattttc ctgttactca ttgatacata gtacttaatt acatgttatt ccatgtacac    180
tgaaaacaat ataggaaata tatacatcta agacttctac tttgtacagt ctttcattaa   240
ataagaatac ttacacatac attttcagat atttctacct tcctgtatgt gtttggaatt   300
gtatgtaggt agccactgaa agaatttggg cccettggga ggatggcagt ggaagtccat   360
gaagtaaaga gcattcttta aaaagcagat ttgattgcat acctttagt tatttgagat    420 tctgagaatt ctgataaacc ccaaagcaga aagattcctt agtacccttg aagatggga    480 aaggtgaggg aaatatttga agcagggtca gaacatccac taagaacata gcacctcagt   540
agagcttaca ttatagtgcc agggtagagt tattactgaa ccaacttttt tgtacaaagt   600

<210> SEQ ID NO 56
<211> LENGTH: 600
<212> TYPE: DNA
<213> ORGANISM: Homo sapiens

<400> SEQUENCE: 56
tccatcaggg cacggtagaa gttggagtct gtaggacttg gcaaatgcat tctttcatcc    60
ccctgaatga caaggtagcg ctgggggtct cgggccattt tggagaattc gatgatcaac   120
tcacggaact ttgggcgact atctgcgtct atcatccagc acttgaccat gatcatgtag   180
```

| | |
|---|---|
| acatcgatgg tacatatggg tggctgaggg aggcgttctc ctttctccag gatggaggag | 240 |
| atctcgctgg cagggattcc gtcatatggc ttggatccaa aggtcatcaa ctcccaaacg | 300 |
| gtcaccccgt agctccagac atcactctgg tgggtataga ttctgtgtaa aattgattcc | 360 |
| aatgccatcc acttgatagg cactttgcct ccttctgcat ggtattcttt ctcttccgca | 420 |
| cccagcagtt tggccagccc aaaatctgtg atcttgacat gctgcggtgt tttcaccagt | 480 |
| acgttcctgg ctgccaggtc gcggtgcacc aagcgacggt cctccaagta gttcatgccc | 540 |
| tttgcgatct gcacacacca gttgagcagg tactgggagc aatattgtc tttgtgccaa | 600 |

<210> SEQ ID NO 57
<211> LENGTH: 340
<212> TYPE: DNA
<213> ORGANISM: Homo sapiens
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t

<400> SEQUENCE: 57

| | |
|---|---|
| ctgtccagaa tgtagaggac agacccatgg gaacttcaaa attcccctct caatncccat | 60 |
| tttatgttag aaaatcaagt accgagaatg ttaangttaa attatgtgac caaaacaagg | 120 |
| aaagaggctg gtaaaactgc attttgcaca aaagtgttga ttcaacatga agtcaaataa | 180 |
| tatgttctaa tgaaaccaca cctctcacac acatatcctt tctctcaaac ctcggtgtta | 240 |
| ctctggccaa aagtcttagg tttcttgaag tgtttgtgga agagtagatg gagttttatt | 300 |
| taacattatc aagaaatcca agctgcagac cccacacata | 340 |

<210> SEQ ID NO 58
<211> LENGTH: 520
<212> TYPE: DNA
<213> ORGANISM: Homo sapiens
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (418)..(419)
<223> OTHER INFORMATION: n is a, c, g, or t

<400> SEQUENCE: 58

| | |
|---|---|
| agacttttta gtagcttcca actacaaaaa aagagaaata atcaattatg tactaatcag | 60 |
| acacttttaa aaattacaac agtttattca gagaaacaag ctttgtgtga cattctaagc | 120 |
| ggattttatt ctgcaggtcc ttttaacata atgagtaata tttgtgttgg aatgactga | 180 |
| gaagaaattt cataatgatg tgaagatcta cctgtaaata gttcctctgt cgtatgctgg | 240 |
| tatttatatt ctagcatctc aacagtgctg atggtcactc atcttggagt tccctgaatt | 300 |
| tttttttttt tttcaaaact cctgtaatgt tacattaccc atactttgt tgttgctgct | 360 |
| gttgttgttg ttttgagacg gagtgtcgct ctgtcgccca ggctggagtg cangtngnnc | 420 |
| cgcgcccggc acatgactgc atactttcaa ggagaggact cagagctttt atttatttaa | 480 |
| agaaacttga aaggaggaaa gtggattaag aaaaaaaaaa | 520 |

<210> SEQ ID NO 59
<211> LENGTH: 600
<212> TYPE: DNA
<213> ORGANISM: Homo sapiens

<400> SEQUENCE: 59

| | | |
|---|---|---|
| tttttttttt ttttacataa aggcatgaat atacaaggta atgtcagcag ctgtactcca | 60 |
| ctctttattc gttgcaaatc tacctatttg tttccaaagg atgtctgcaa ataaataggt | 120 |
| aacattgtac agctttcaac agtggatcag aacatagatg tctcttctaa ttcacaagta | 180 |
| ccaatggctc aattaattta agggacattt tctgagttgt gtgatttcac atgtatttat | 240 |
| cgtgtctaga agtgtgcaaa cttttgtttc atttctctct tagatttctg taggaagagt | 300 |
| taaaggatgt gaagtagtca ttttacttat tcataacaca ttttagggaa aattgtgctg | 360 |
| ttgctgttgg ggagaaagtt aaagctatca actataacct ggactccagt ccaattttc | 420 |
| acatctggtt gctacttta aaaggatca ttttaatttt taaatgcaga atgtgttgca | 480 |
| ctttaccttt gacattccag gtttcctcat ggtcatttag aaaaataaag caggaaattc | 540 |
| taatgcctta gcatctactt taataagatg tttgcattta taaaaataac aagaaactga | 600 |

<210> SEQ ID NO 60
<211> LENGTH: 463
<212> TYPE: DNA
<213> ORGANISM: Homo sapiens
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t

<400> SEQUENCE: 60

| | | |
|---|---|---|
| tttaatttt tggaaggata tacaccacat atcccatggg caataaagcg cattcaatgt | 60 |
| gtttataagc caaacagtca ctttgtttaa gcaaacacaa gtacaaagta aaatagaacc | 120 |
| acaaaataat gaactgcatg ttcataacat acaaaaatcg ccgcctactc agtaggtaac | 180 |
| tacaacattc caactcctga atatatttat aaatttacat tttcagttaa aaaaatagac | 240 |
| ttttgagagt tcagattttg ttttagattt tgttttctta cattctggag aacccgaagc | 300 |
| tncagctcag cccctcttcc cttattttgc tccccaaagc cttccccca aatcatcact | 360 |
| cncctgcccc ccttaagggc tagagggtga ggcatgtccc tcacaattgg cacatggtnc | 420 |
| aaggccatca ggcaagggng cattcacaca aaagggcacc agg | 463 |

<210> SEQ ID NO 61
<211> LENGTH: 600
<212> TYPE: DNA
<213> ORGANISM: Homo sapiens

<400> SEQUENCE: 61

| | | |
|---|---|---|
| gaaacaactg gtaaacacag taagcccatt tctgggcttt tagaaaaaca ttgctctctt | 60 |

```
ttctttcccc acccagtgta ttcccaagga cttaatgctg cactctgacc tagccctcaa    120
tgatggttaa aactgattct gaaccaaagg taaacagggt tcctccccat gccttggaga    180
gctccagtct gcagaaagct aatgaagccc ttgaagcagt atcttgtctt ccatccacac    240
tttattgaaa tgcttttgaa tcttattgtg ttgtaattac atactataga aaactccgcc    300
aacctctatt tcaaggtttg ggcccatgac tctcgctaaa acatttcagt tccattttcc    360
agaacatacc atttctaaat gcatctgtga gggccctcca caagtatttt cagtccacat    420
ttcagaaaac ttgaaagtga cgcaggttcc tgacttagtt gatggtgggt aaagggaatg    480
ccattatgag tggtggaggt tgttttcttt tttcttgcca tattctcagc ataatatttg    540
aaacctacaa aagaagtttg ataatataac tgtatatttt atgcctgcac tagtggagga    600
```

<210> SEQ ID NO 62
<211> LENGTH: 600
<212> TYPE: DNA
<213> ORGANISM: Homo sapiens

<400> SEQUENCE: 62

```
gaggtaggaa ctgatattcc cattgtacag atgagaagac agatgctcag agagcttatt     60
tgtctgttga agccaaaacc tgtgcccttg accacaatgg acactatatc ttctgagctc    120
cacttaatta gagaatttgg atcaagtgac taaataaatc acacaccaca cacattaaga    180
tacgccagag tgacagggac attaaataaa tcaagtatcc atgaagtttg ctgccttcca    240
aatcagcccc ctattctttt gccctaagat atcccatcat agtctgtttc cttcccttct    300
ctctttgccc tcaaccttte cttccctctt atccatggga atgactctag gaatcctgtt    360
gagtgtatgt gtgtgcgtgt tcttttcttt ttctctcatg aatattacac ttttattagc    420
cagctatact tgtgttgatg aaaaagacaa aatggaattt tgttttcctt taacaatcaa    480
gtatgaatgg tctgcttaca ggatgtccct tcttgggtc cttggaggta acaaaagctc    540
atcattaaac aggtagctat catttctaca tgcttagtat cacttccgat tatcttattc    600
```

<210> SEQ ID NO 63
<211> LENGTH: 600
<212> TYPE: DNA
<213> ORGANISM: Homo sapiens

<400> SEQUENCE: 63

```
gggctgaggg tcctgaggag agagagagag gccacgtgga tggaggactg tcacccccttt     60 ctcggttctg tcaccccctt gagtctaact cactgttgag gggaggaaga aggggggatgg   120 acggaaggga gaccgaggaa aggctttcgg gagtggggac attatccccc cagaggtgtg   180
ctgccccacc cagctgcacc ccacaatctg gccaactcat ttcacagtat aaatcactcc   240
agcaggacgg catcacagca gccctgctg cctgaaatca gagcggccca acgaggaagg    300
ccaggagggt cggctggcag ggggcagggt cttgggataa cactgtcatc agaaacaagg   360
ctgggggctg atttcggggt ggggagcctt aggaggccag aaattccaat cagagccagt   420
ttttctggga gggagtggct agacagtcaa ggaaggacgt tcacatttca aaagaagtcg   480 ggtggggga tgagattatt ctaggggggc atcgaattcc ctttaagggg ggggctcact    540
tctgcccaga gtaaagagga tctcacacca tggaaatgtg ccaactttt tgtacaaagt    600
```

<210> SEQ ID NO 64
<211> LENGTH: 600
<212> TYPE: DNA
<213> ORGANISM: Homo sapiens

<400> SEQUENCE: 64

```
cttccattcc tcatgatttt agggttatcc tcattcagat ctactctagt tataatagta    60
ctttaaacag agcacagaat taaaccatta gtatgtgaat ctgcaaaaag agaacttgtt   120
ttagactctt ctacagttta gacttcaatg tgcatactaa atgcataaca ttcgtatcaa   180
ataattaaca tttatataca attaacaaat aaggacaaat tttatacaaa acttctacta   240
ctgctataat ttttgaaaac atttaaccca ctagcaagag gtaagacagc actgcctttt   300
taaaagacag gtcacttgaa tagagaatat aagatataac cataagtagg agtataaaca   360
ataatttttc ttcttgtgga atgttttttaa atttcctttc ttatattatt attcttcctt   420
aggttttttt agacaggtca tttcttcctg aatgattttc ctttttcttt tattttttatt   480
ttttgaagga ggattattta ctggtggtct aaaagaagta ccttcaactt cttcataatt   540
gtagccaaag cggaaatgga atatttaata attcttacat ctcactaatg tagtcttctg   600
```

<210> SEQ ID NO 65
<211> LENGTH: 427
<212> TYPE: DNA
<213> ORGANISM: Homo sapiens

<400> SEQUENCE: 65

```
aataattata aagtttattt aaatgttgat tgtcccaagg tctacagttt cttttctgtt    60
gtgtcatcag tgacaaagag taaaaaaaag gaaactccca tatttagcac tttagagtaa   120
aacacatgga tcatcgttat taacagtcct ctgggcgtgc tggagctcac tgagaaggct   180
tctattttga gcttggaatg ttgtgctgag ctgtgcagcc tgttcctgca tctgttgttc   240
ctgcattttc tgttgctctg ccagccaatt ttgtttggct atctccattt aactcacttg   300
ttcctgatgg agtctctccc tctcctgcat catttgctcg ttctgccttt gaatcgccgc   360
caacctttgc gcttcagcct tttcagcttc tgctttcact tgtgcctctg aggagaaaaa   420
gataatc                                                             427
```

<210> SEQ ID NO 66
<211> LENGTH: 600
<212> TYPE: DNA
<213> ORGANISM: Homo sapiens

<400> SEQUENCE: 66

```
gtgtcaacat ttatgctcct aaaggatgtt gggtcaaatg aaatgttcct cattgtttct    60
ctctcttgat ctctccttca ctccttctct tccttgcagg atctccaact ccttcataag   120
ggcactctgt gttaccccctt taaacaaaat aaagaagtcc tacattctgc ccagattttt   180
ttcaggctcc accaaagggt tgggtgaatt atggcccaaa agttggtgag gatgatggtg   240
aaccttcaat caccttcagt ctcccaacca acaatggtca tggcttgttt ctccctgga   300
ttacatggag aaaatcatgc cctactttt ggacctgttg cttctacatt tgtatggtaa   360
ctgtgaaacc atcctaatga acagcaaaca ttaaccacta cataaaatgt agactttgaa   420
taaaaacaca gctaagtact aaccagcttg ccctttaagc caattccctg tagctactta   480
cagcacgact gttagctcct ttccttatag tttcttactg ccttaaagtc acatagatgt   540
ggtcacaagg cactaacttc ccttagttat ttctataaga taatatatgt aacgttggca   600
```

<210> SEQ ID NO 67
<211> LENGTH: 600
<212> TYPE: DNA

<213> ORGANISM: Homo sapiens

<400> SEQUENCE: 67

```
agtgcagaga ggatgagaat atccttcatg gggtccagtt ccaaatctga agcataattt    60
ccaaccatca aaatattgga aataggaatg cctagcattt tatggacatt catgacccgg   120
ctttgagaag tcatagatct actcatgttt aaaaagttgt cttgaagaac ctcactgcaa   180
tcatccactt tagtaagcaa ggccacatat gctataccac agtttaatac ttctttgtga   240
acttgcttca cttttgccaa cattttagag tagagattgt caatagagtt gatgtctaag   300
acataagcca cacagtgaat cctgtccttc agagatggag aggtgataaa agtagaatgc   360
tcaggtgtaa ttggtttacg ggaattaaac tgttataaaa ataaggta acattcagaa   420
atcagagagc ctctgtttaa cccttaaaga cacaattaat gcttctaata ctgtaactac   480
tgatctccct ctttctcctc agctactctt tccccaaaca gtagcacctc ctctttactt   540
cctttctcac tgggggcat aatgccacca actttttgt acaaagttcc cttttaatg    600
```

<210> SEQ ID NO 68
<211> LENGTH: 577
<212> TYPE: DNA
<213> ORGANISM: Homo sapiens

<400> SEQUENCE: 68

```
ttatcttata ctaaattcca acatgtatct gagtttgctt ctagattttc tgttctgtcc    60
cagtggttgg atatttcttc atacacgtct atcatactgt tttgactata gaggcttttc   120
agtgtcattt aatatctgtg atggcaatcc ctactcaaag ctctttgttt tcagtgttcc   180
tgtattgctc ttttgttaat cccttaatat aaaagtaaat aataacccag ttggcatatt   240
attttgatga cattaaattg gggagaatag atactgtgat ttttgaagct tcctacaaat   300
atgatatgct tttcatttgt gcaagtactt tagtataatg ttaactggtg gtggtaatgg   360
aggaaattct gtcatgttcc ttacttttag tttcctctag cgctttctat ttttttattt   420
tttttcagat ggagtcttgc tctgtcttct atccaggctg aggcaggagg atcacttgaa   480
cccagtagtt caaggctgca gtgagctatg gttacaccac tgcactccag cctgggtgac   540
agagcaagat gccatctctt aaaaaaaaaa aaaaaaa                            577
```

<210> SEQ ID NO 69
<211> LENGTH: 600
<212> TYPE: DNA
<213> ORGANISM: Homo sapiens

<400> SEQUENCE: 69

```
gttaatatct ttttcgttta ttgtctgtct ctgaaggtag ggactttgcc tcatttactg    60
cttttcagtt cttggaacaa tgctcggcac ataggcaatc aacgaatgtt tgttgaataa   120
atgatttttt tctctggaaa ttgtcaaaat ctgcatgagg tgtatcaggc cagccattgt   180
cagcctcagt ttagaggcaa ggaaataggt tcagaaaggt tcaaggacgt gctgaagtca   240
cagggcgagg cagcagcaga gagcctgctt gttgagagcc aagtcttatg ggacttgcct   300
ccttctctcc cactgaggct ggggacacca ggtggcccag aggcatgtgg atacctccag   360
tgggaggtta ggagagtgct acacagaaac tctgagttct aacactcttg ggaccataaa   420
aaatggaaca agtctgggca tggtaactca cgcctgtaat cacagtattt tgagaggctg   480
aggtgggagg atcacttgtg gccaggagtt cgaggctgca gtgagctatg atcctgccac   540
tgtactccag cctgggcaac acagagagac ctcacttctt taaaaaaaaa aaaaaaaaaa   600
```

<210> SEQ ID NO 70
<211> LENGTH: 600
<212> TYPE: DNA
<213> ORGANISM: Homo sapiens

<400> SEQUENCE: 70

| | | | | | |
|---|---|---|---|---|---|
| aggagaaagg | gaagtcaaat | gtctcgtcca | agtctacaca | gctaaaaagg | ggcagaacta | 60 |
| gggtgacgct | caggcctcat | ttagagatcg | ggggttggcg | agaagtgggg | tgggcttctg | 120 |
| gaggggctgg | gagagcccca | caaggctgca | gagggtggtg | agcccggagt | gggcctggcc | 180 |
| tggtgtgggc | tgggggtatg | ggcaggagct | gcagacagca | gggctgcacc | agcggaccag | 240 |
| tttcagaggc | aagggttcta | ggcccttgag | aatccacagt | gccaaacaga | cccagatagc | 300 |
| tacgggggttg | gtacctgggg | aggccttagg | acaggcagaa | agtcccagag | gcagggcgt | 360 |
| tgcctgggga | cgttttttgct | ccctgtcctg | ctgacagagc | ataggaagtg | tgaatgtttt | 420 |
| ctaccccctc | ctctctcggc | tcagcagagc | tccagcgagc | caagtccttg | tctgtggaga | 480 |
| cgcatcagtc | cctggctcta | gggaataggg | agtcccacag | acaggggggt | gtcagcaagc | 540 |
| tgagagggtc | tgtaagtagg | tacggaattg | agtcaggaaa | cagtctgggt | gtggagtgag | 600 |

<210> SEQ ID NO 71
<211> LENGTH: 600
<212> TYPE: DNA
<213> ORGANISM: Homo sapiens
<220> FEATURE:
<221> NAME/KEY: misc_feature
<222> LOCATION: (65)..(83)
<223> OTHER INFORMATION: n is a, c, g, or t
<220> FEATURE:
<221> NAME/KEY: misc_feature
<222> LOCATION: (132)..(144)
<223> OTHER INFORMATION: n is a, c, g, or t

<400> SEQUENCE: 71

| | | | | | |
|---|---|---|---|---|---|
| tgcaaaaagc | caaaaaaagc | agcttttaac | attatatcat | tatatcacaa | ttttgaaaca | 60 |
| tgggnnnnnn | nnnnnnnnnn | nnnccattgt | gtggataaaa | tggtctccgt | gacattgagc | 120 |
| agagtgttat | cnnnnnnnnn | nnnnacatta | ttgcacagag | atttctcatc | aatgttcttc | 180 |
| agttttatg | tcttttccta | aatgtgaata | agtgctatgg | ataaaataca | aatgtagaaa | 240 |
| ataacagcag | catgatttgt | caagttaat | ccctataatt | tagtaagaaa | aaatggatat | 300 |
| aaacaaaata | agtgctcttt | ctaaactgta | ctaaattttc | aaaaatattg | ttttaatgca | 360 |
| gtgaaggtcc | tgaaaagcct | attgaaagcg | atgctgagtc | ctgttttcaa | aagtgtcctg | 420 |
| tttgggtttt | cttggtgaag | agcagaattt | caagtgaagt | aatcgacgga | ctaatttaaa | 480 |
| acaaaacagc | cctcggcttc | cctattggcc | tgtgagggca | ccggctccgg | gaccctgacc | 540 |
| tgggaggcag | cgagtggtgg | gggtgcctgg | cccccatcta | cacgtacaca | ggctggccaa | 600 |

<210> SEQ ID NO 72
<211> LENGTH: 600
<212> TYPE: DNA
<213> ORGANISM: Homo sapiens

<400> SEQUENCE: 72

| | | | | | |
|---|---|---|---|---|---|
| gcacgtctac | ggggctggac | agagtgtggt | taaccgggga | actgggcaag | ccggcgccga | 60 |
| gcctgcgtca | gccgtgcaag | ccgctcccttc | aggaacttcc | gcttgtcgct | ggtgtcgctc | 120 |
| cgctccttca | ggagccagct | gtaggtgtcc | ttgtcctgca | ggagctgcag | catggccttc | 180 |

| | |
|---|---|
| tgaagctgct ggccgtacgt ctggagcatg aagaactgga tgatcaaagg gatgtggctg | 240 |
| gagatgcgct tgctggcctc ctggtgatag gccatcaggt gctgaaagat ctcctccatg | 300 |
| gaagagtctg ttgccgagct ggactggaaa gccccaaaat cccaggattt cttcttcttt | 360 |
| tcttcttcca gctccttctc tctgaccttc tgcaatgcac ccctgtatac ctggtcctgg | 420 |
| cagtagacaa tctgttccat ctggaagtgg aggcggatca gcttctcacc ttctctctct | 480 |
| tgttctgctc taatgtcttc aattttggac ttggcggttc tgtggaggtt aaaaaactct | 540 |
| tcaaaatttt ttatcgccaa cttttttgta caaagttggc cttataaaga aagcattgct | 600 |

<210> SEQ ID NO 73
<211> LENGTH: 600
<212> TYPE: DNA
<213> ORGANISM: Homo sapiens
<220> FEATURE:
<221> NAME/KEY: misc_feature
<222> LOCATION: (1)..(261)
<223> OTHER INFORMATION: n is a, c, g, or t
<220> FEATURE:
<221> NAME/KEY: misc_feature
<222> LOCATION: (522)..(549)
<223> OTHER INFORMATION: n is a, c, g, or t

<400> SEQUENCE: 73

| | |
|---|---|
| nnnnnnnnnn nnnnnnnnnn nnnnnnnnnn nnnnnnnnnn nnnnnnnnnn nnnnnnnnnn | 60 |
| nnnnnnnnnn nnnnnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nctaaaaaaa tatgtactgc ttattttgtt agcatacttt | 300 |
| taattatatt cttattctttt ctaccctct caaaatgtat ttttccagct tgccatttaa | 360 |
| ttggtaaaca gctgtaaagt tcaaacgtga aattcttaaa gctccctaga gacatacaca | 420 |
| ataacttctg tggcatggac ttttctcggc attaaaaaaa tctagtacct ctcttggcca | 480 |
| gaaccccctaa ttttacactt tatggtgttg cgtcgttttt cnnnnnnnnn nnnnnnnnnn | 540 |
| nnnnnnnnnt tactggcaag ttttcctcc aaacagtttt ctaatcaagt ctaataagtt | 600 |

<210> SEQ ID NO 74
<211> LENGTH: 600
<212> TYPE: DNA
<213> ORGANISM: Homo sapiens
<220> FEATURE:
<221> NAME/KEY: misc_feature
<222> LOCATION: (1)..(44)
<223> OTHER INFORMATION: n is a, c, g, or t
<220> FEATURE:
<221> NAME/KEY: misc_feature
<222> LOCATION: (95)..(121)
<223> OTHER INFORMATION: n is a, c, g, or t
<220> FEATURE:
<221> NAME/KEY: misc_feature
<222> LOCATION: (144)..(172)
<223> OTHER INFORMATION: n is a, c, g, or t

<400> SEQUENCE: 74

| | |
|---|---|
| nnnnnnnnnn nnnnnnnnnn nnnnnnnnnn nnnnnnnnnn nnnngatgag ccaggcatgg | 60 |
| tggtatgtgc ctttagtccc agctatctgg gaatnnnnnn nnnnnnnnnn nnnnnnnnnn | 120 |
| ntgacggcaa gagcctgtct ctgnnnnnnn nnnnnnnnnn nnnnnnnnnn nntctgatca | 180 |
| gttaaatgaa tatggaaact taatcttgta ccccttacct cccaagcata cagccacagt | 240 |
| ttaccgttgg agggatcttt ccacggaggt aaacagtgct gttttctcca agtgccagaa | 300 |

```
caaaaacaca acagcacaca cacaatgaga tggtttggct ctgtgtcccc aaccaaatct    360
catctcaaat tgtgtttggc tctgtgtccc caaccaaatc tcatctcaaa ttgtgtttgg    420
ctctgtgtcc ccatccaaat ctcatctcaa attgtaatcc ccatgtgtca agagagcaac    480
ctggtgggag gtgactaggt catggggtg gttttctca tgctgctctc atgatggtaa      540
gtgagttctc acaggatctg atagtttaaa agtgtttagg ggctgggagc agtggctcat    600

<210> SEQ ID NO 75
<211> LENGTH: 600
<212> TYPE: DNA
<213> ORGANISM: Homo sapiens

<400> SEQUENCE: 75
gggtgaggac ccacagctct gatgtgggcg cttcaggcca tggtggagct gagattcagg     60
ttggcttttc ccctcagctc ccagctggct ggtgaaccca tcatcatagc caaaagtact    120
cagcagcagc acctccaggt ccagaggcac ctccagctgc atgcacacac aatgaatgaa    180
agactgccag gtgtccgaac cctggacatg cagcttgttg agttgcagga tgactctctg    240
ttcagggtcc aaggtctcgt tcctggaatc caggtccgtg ttggggagga agaacttcat    300
cttggcgttc agccattctg ggtctttggt gagcagcctc acaagacagc tccacaggtt    360
cttgttgccg agctggaggc caacggggtc catgaggagc cagccttggt ctcctcgttc    420
atgataggtg ctctagggtc cccacggaga gggtctcatg ggtgtctggg ctatgtgtgc    480
cttgagctgg attgacaggt tgtttccata gtgcagactc cctcagcgct cgcggctcct    540
ccgcgctctg cacgaaactg aaagtagaag ccgccgccta gagctgctcc gccagtgcat    600

<210> SEQ ID NO 76
<211> LENGTH: 600
<212> TYPE: DNA
<213> ORGANISM: Homo sapiens

<400> SEQUENCE: 76
tggcaaggac attgtttttg tctagtgtct caagcttctc taccaagaga gtcatatttc     60
ttatctccac ctccagctgg tcaacaattt ctgagcttcc accaaaactc tccttcagct    120
gtatgaccag ttttttccatc tccttcactt ctaccttgat cagctcgaag tccagttcag    180
tgtaagaaat ggtatccttc tccatgatgt caattcggac agttaggttt aacagtttct    240
tttcatacac actaattaat tggacatatt ccctcacttt agaaagttct ttctcaaact    300
tctgagaaag aacatgagct gtgaattcca agcgttccac tctgtccacg ggaaaggtgg    360
tgtctggcag ggaaacagag cactggcagg tcccacggtc atccacggag ccggtgaaat    420
tggaaaacaa ctgggacaca gaacctccgc tgcctaagct gcggctggag ctggagcccg    480
acctggagct ggagctgaag ctggagctgg agtcaacacc tgggaaagag ctgaagccgg    540
ggctgggaat tggaggtccc acatccccca atcccctgc agcttggcca aggaagccaa     600

<210> SEQ ID NO 77
<211> LENGTH: 600
<212> TYPE: DNA
<213> ORGANISM: Homo sapiens

<400> SEQUENCE: 77
tcttttattg aaagaaaaaa caatacaatg gactttaaaa agctacattt gttatggttc      60
ataaggacag aggtttacac aggttttata tatgtacaca ctgacaatac tatatcacaa    120
```

```
catcagaggc accattttg ccacagaatt aggtaatgaa taaaacttct ccaaattaat      180
ctgttttaaaa aatatctaaa atggtacagt atatttgagg attatataaa tatgtgagac    240
atatttagat atttttttaaa aatagtgttt atatatatgc atcacaatct tctctaattc    300
tcaaaatatt atggcaccaa aattctgttt gtcaaataaa acacaagatg ctgtaatatg    360
tatccaagca ccagcttagc acagtattta attctccccc aaactgaaag actgctaaca    420
ggtacaaact gaactgaata tttcacacaa ccattgaaat aatttaggcc ctcaaatttt    480
tttttttatta gctgattgtt tttagagaaa aaagagggag ctaaaccatt tacattaatg   540
ttgctctgtg tgatagaatc aatcctaggg ctcagagaag atattcctag gcactggaga   600

<210> SEQ ID NO 78
<211> LENGTH: 475
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n is a, c, g, or t

<400> SEQUENCE: 78
tcaaacttga atcntttaaa tttattttct gcttaagcag gtttgagttg ggttttctat     60
ttgcaatagc aaaagtcctg actggcaagg tttaaaagtt tgaagactct cacaggtaag    120
tgcagctcag gatcctgtga gtgcagcaga aagtcttaag aaatggcagg ggctggttga   180
acccagattt tccattggct gagcagatat ccccagaggc gtagaaaatt aaatttgttt   240
tatgttgttc caaagagga gaactgaggc cagaggagca cacttctgag acactcattt    300
ttgctgggta gaggaactct ctgggcaagc aggaccatcg atattagagc agctggcctc   360
aggaggggag taagagcccc atccctgaag gtacacaagt tgtggcagca accatctggc   420
ctgcagtttc cagaggggag tcaggcgtgg ggtgggactg gagtgaacgg gtacc         475

<210> SEQ ID NO 79
<211> LENGTH: 600
<212> TYPE: DNA
<213> ORGANISM: Homo sapiens

<400> SEQUENCE: 79
ttttttcttc tttcctcttt gggttttccc aaagtagagt tgtttgcaat atccacagta     60
tccatttttgc cacatgcttg gtcactttcc ttccttgctt ccgggctttc tgcacttct    120
ccttgtttaa gacttagttt gatgtcaggc ctctcttccc tttcttttcg atcactttct   180
tggaaagaca atttgtcttg gattgcattt ttgaagcttt tataaatgtg aattaaatcg   240
gggtattcct gcatgttgac ctcgctgaac agtgcttcca aaactgacag gttaaatgtc   300
ttctccagtt cactgagaac attgtacacc actctttgta cagggaccag gtttctacaa    360
gaatcttcag aatcttcaaa cattttattt gtgatgagtt cccgatcgcg gaggccctca   420
aggaatggaa atgtcttttt tattgcattt gatatctcca gcttatgtct tttgaagtgc    480
ttgaatacag tgtcatagac aagtccctca tctacatcct ggtcttccgt gaacagcctg   540
gctcggaagg tcctacgccc acggactctc actgattgct agcacagcag tctgagccaa   600

<210> SEQ ID NO 80
<211> LENGTH: 600
<212> TYPE: DNA
<213> ORGANISM: Homo sapiens

<400> SEQUENCE: 80
```

```
ccttccccat ttctcacttt ccacaggtgg gatgtggcag tcctcatgga agactcttga      60
acaagtgtcg caacagaaca gctcccctcc gtcccggcac acctcacact catccaagtt     120
tctcatctag aaggtaaaac agtgtccacg tcactgggaa tcacaagatt caggaaggcc     180
acccctctgg gcatctagaa cacactgctt atgtgtgagc ctgtatagac aggcatatgc     240
ttctccctgg gatatgaagg aaaaatatgg catggagatt tcagaacaaa tcctggtctg     300
cagtgaagtt caggaggaag gggtatatgt cagaataaaa acgttttcct tataaaacca     360
gagattatga cacagaaagc ctagcaacaa agcaagagga tgatcttata ggaatctgaa     420
taattgtatt atgctgcaga taaaaccagg ttttgaagta aaagtgttaa atccatttgt     480
ctatactaca aatcaactca tgaaagggag acccagagaa ttacatatga tggaataacc     540
ttctaagata tcatcacatc ccatattctt ggccataagt tccccatgag ttgaagacag     600
```

<210> SEQ ID NO 81
<211> LENGTH: 600
<212> TYPE: DNA
<213> ORGANISM: Homo sapiens
<220> FEATURE:
<221> NAME/KEY: misc_feature
<222> LOCATION: (445)..(456)
<223> OTHER INFORMATION: n is a, c, g, or t

<400> SEQUENCE: 81

```
gtggctgttg ctggccccac ctccgcttat gtccttaaca tgcctcaggt ggttcatccc      60
ttttggcact catggtgccc cctgtgggct gatacaggag tgagtctact gtgaaggcac     120
tcagtatagt ggaaaaaaca aatatcaacc tcctgctttt tttcagtgta aaaactataa     180
gctctatggg agtttctgca gatggtacca taatggcctg agggaggagt atcacagtca     240
cagagtattg gttctctcac tgcataagcc atggttttac ccaccttcac aggctaaagg     300
tgcttcataa ccttgttcat gtattgaggt tctgttggct cttgtaatgg taatttcaca     360
tgtgggcagt tgttcatatt gatgtttcta taggggtatg atagctggag aggtctgcgc     420
cactgtcttg ctctgccttg atcannnnnn nnnnnnaaca agaatttgtc tcctcctagt     480 ttttctttt ctcttaaccg acctaggttt agccttttaa tccttctccc tcctctgctt     540
ctaatgtcat tgtttctttg tatgcctatc atatctacat gctacatgac cttcagctgg     600
```

<210> SEQ ID NO 82
<211> LENGTH: 600
<212> TYPE: DNA
<213> ORGANISM: Homo sapiens

<400> SEQUENCE: 82

```
agttttaagg aaaaattgta tgatttaaaa gattataaaa ctttattact gggctattta      60
cacattttaa ttgtttctca taaaatatat aacattacaa tatttatgga agtaggatat     120
ttttgtatca tatgtacgat gataaattat agggtatttt aaatgatgtt ttttagcctc     180
cttaagtttt aagtggatct tgcaaatgaa aacaagtatt attgagtttg acatactcaa     240
attgcccaaa tatcagctgt ttaaacaacc aagtcatcat tgatacttta gtaaaggtta     300
gtaaatgtca tcaaaggctt atttgcagtt tacagttttt attacttagg agacttaagg     360
agtacctgcc aggtttgtcc atgctaatgc tacgattttg ttttgtagt tcaaccatat     420 tttgtatgga gatactttga ggctctgtaa atttctggtt actcctcaga acccactaga     480
tttagcattt catggatgac ttgtgtttga acaattatta ctataatggt tgccagatga     540
```
ttatttcctt attctcttct tgttctaca tggagaaata aaccaataa ataagggaga    600

<210> SEQ ID NO 83
<211> LENGTH: 276
<212> TYPE: DNA
<213> ORGANISM: Homo sapiens

<400> SEQUENCE: 83
gtgccaatgt gaagtctgga ttttaattgg catgttattg ggtatcaaga aaattaatgc    60
acaaaaccac ttattatcat ttgttatgaa atcccaatta tctttacaaa gtgtttaaag    120
tttgaacata gaaataatc tctctgctta attgttatct cagaagacta cattagtgag    180
atgtaagaat tattaaatat tccatttccg ctttggctac aattatgaag aagttgaagg    240
tacttctttt agaccaccag taaataatcc tccttc    276

<210> SEQ ID NO 84
<211> LENGTH: 184
<212> TYPE: DNA
<213> ORGANISM: Homo sapiens

<400> SEQUENCE: 84
aatgcttatg tctaaaagag ctcgctggca agctgcctct tgagtttgtt ataaaagcga    60
actgttcaca aaatgatccc atcaaggccc tcccataatt aacactcaaa actatttta    120 aaatatgcat ttgaagcatc tgttgattgt atggatgtaa gtgttcttac atagttagtt    180
atat    184

<210> SEQ ID NO 85
<211> LENGTH: 206
<212> TYPE: DNA
<213> ORGANISM: Homo sapiens

<400> SEQUENCE: 85
ctgggcacct ctgggacagc aaaaaaaact gcagaatgca tccctaaaac tcacgagaga    60
ggcagtaagg aacccagcac aaaagaaccc tcaacccata taccaccact ggattccaag    120
ggagccaact cggtctgaga gaggaggagg tatcttggga tcaagactgc agtttgggaa    180
tgcatggaca ccggatttgt ttctta    206

<210> SEQ ID NO 86
<211> LENGTH: 268
<212> TYPE: DNA
<213> ORGANISM: Homo sapiens

<400> SEQUENCE: 86
accatgttca tcttgtcctc caagttatgg gggatcttgt actgacaatc tgtgttttcc    60
aggagttacg tcaaactacc tgtactggtt taaataagtt tacctttcc tccaggaaat    120 ataatgattt ctgggaacat gggcatgtat atatatat ggagagagaa ttttgcacat    180
attatacata ttttgtgcta atcttgtttt cctcttagta ttccttttgta taaattagtg    240 tttgtctagc atgtttgttt aatccttt    268

<210> SEQ ID NO 87
<211> LENGTH: 234
<212> TYPE: DNA
<213> ORGANISM: Homo sapiens

<400> SEQUENCE: 87
gatggctggt ctgcccccta ggagactccg tcgctccaat tacttccgac ttcctccctg    60

```
tgaaaatgtg gatttgcaga gacccaatgg tctgtgatca ttgaaaaaga ggaaagaaga    120
aaaaatgtat gggtgagagg aaggaggatc tccttcttct ccaaccattg acagctaacc    180
cttagacagt atttcttaaa ccaatccttt tgcaatgtcc agcttttacc ccta          234
```

<210> SEQ ID NO 88
<211> LENGTH: 231
<212> TYPE: DNA
<213> ORGANISM: Homo sapiens

<400> SEQUENCE: 88

```
ggcatggagc atctgtacag catgaagtgc aagaacgtgg tgcccctcta tgacctgctg    60
ctggagatgc tggacgccca ccgcctacat gcgcccacta gccgtggagg ggcatccgtg   120
gaggagacgg accaaagcca cttggccact gcgggctcta cttcatcgca ttccttgcaa   180
aagtattaca tcacggggga ggcagagggt ttccctgcca cagtctgaga g            231
```

<210> SEQ ID NO 89
<211> LENGTH: 241
<212> TYPE: DNA
<213> ORGANISM: Homo sapiens

<400> SEQUENCE: 89

```
gaaattagag tcctatattc aactaaagtt acaacttcca taacttctaa aaagtgggga    60
accagagatc tacaggtaaa acctggtgaa tctctagaag ttatacaaac cacagatgac   120
acaaaagttc tctgcagaaa tgaagaaggg aaatatggtt atgtccttcg gagttaccta   180
gcggacaatg atggagagat ctatgatgat attgctgatg gctgcatcta tgacaatgac   240
t                                                                   241
```

<210> SEQ ID NO 90
<211> LENGTH: 199
<212> TYPE: DNA
<213> ORGANISM: Homo sapiens

<400> SEQUENCE: 90

```
ttagatttcc agcttgtcac cttcaaggtt accttgtgaa taggactttt ttgagctatt    60
tctatccagt tgactatgga ttttgcctgt tgctttgttt ccaccaactc tccctgaaga   120
tgaggcgcac agacagacaa ctcacaggca agaacagcct ggtccatctt gaaagattct   180
caagactatt ctccacaag                                                199
```

<210> SEQ ID NO 91
<211> LENGTH: 210
<212> TYPE: DNA
<213> ORGANISM: Homo sapiens
<220> FEATURE:
<221> NAME/KEY: misc_feature
<222> LOCATION: (70)..(70)
<223> OTHER INFORMATION: n is a, c, g, or t

<400> SEQUENCE: 91

```
tgtttaaaaa tgttgtgggt acatagtatg tgttgtgggt acatcgtatg tgttgtgggt    60
acatagtatn gtggggtcca tgagatgttt tgatacaggc atgcaatgtg aaataagcac   120
atcatgggga atggggtatc cctcccctca agcgtttatc cttcaagtta taaaaaattc   180
aattacagtc ttagttatgt caaaatgtac                                    210
```

<210> SEQ ID NO 92

<211> LENGTH: 148
<212> TYPE: DNA
<213> ORGANISM: Homo sapiens

<400> SEQUENCE: 92

```
accagaattt atggatgaac tgattgctta tattttagtc agggtttata aatgtagatg    60
gtcaaattta cattgcctag tgatggaaaa ttcaacttttt tttgattttt ttttccaata   120
ttaaaaaagg ctctgtatgc atggtggg                                       148
```

<210> SEQ ID NO 93
<211> LENGTH: 227
<212> TYPE: DNA
<213> ORGANISM: Homo sapiens

<400> SEQUENCE: 93

```
aagattcctg tgtactggtt tacatttgtg tgagtggcat actcaagtct gctgtgcctg    60
tcgtcgtgac tgtcagtatt ctcgctattt tatagtcgtg ccatgttgtt actcacagcg   120
ctctgacata ctttcatgtg gtaggttctt tctcaggaac tcagtttaac tattatttat   180
tgatatatca ttacctttga aaagcttcta ctggcacaat ttattat                 227
```

<210> SEQ ID NO 94
<211> LENGTH: 245
<212> TYPE: DNA
<213> ORGANISM: Homo sapiens

<400> SEQUENCE: 94

```
tctcctctca tctgcatttc tcagaaatgc cctccctgcc cagtggtgac tttccctcgt    60
cactcctatg gagttctacc tggagcccag ccatgtgtgg aactgtgaag tttactcctc   120
tgtaaagatg gtttaaagaa agtcagcttc tgaaatgtaa caatgctaac ccttgctgga   180
accctgtaag aaatagccct gctgatagtt ttctaggttt atcatgtttg attttttacac   240
tgaaa                                                                245
```

<210> SEQ ID NO 95
<211> LENGTH: 221
<212> TYPE: DNA
<213> ORGANISM: Homo sapiens

<400> SEQUENCE: 95

```
gaattttttct ctatttccag cacgctgatt tgatttaaaa atgtaataag accaagagtt    60
ggagtaaagg gatattcatt ccatgttaaa agtggcttca tagctactga caaatgtctg   120
aactattgtc gtgcccttca aaactggagt tttctaaaat aatcttattt ttatacttgt   180
atgttccagc aatttaagat ataccatt gaaagggaaa t                          221
```

<210> SEQ ID NO 96
<211> LENGTH: 176
<212> TYPE: DNA
<213> ORGANISM: Homo sapiens

<400> SEQUENCE: 96

```
ggctgagcaa ggcacatagt ctactcagtc tattcctaag tcctaactcc tccttgtggt    60
gttggatttg taaggcactt tatccctttt gtctcatgtt tcatcgtaaa tggcataggc   120
agagatgata cctaattctg catttgattg tcactttttg tacctgcatt aattta       176
```

<210> SEQ ID NO 97
<211> LENGTH: 219

<212> TYPE: DNA
<213> ORGANISM: Homo sapiens

<400> SEQUENCE: 97

```
aacgcaggcc gctttattcc tctgtactta gatcaacttg accgtactaa aatcccttc      60
tgttttaacc agttaaacat gcctcttcta cagctccatt tttgatagtt ggataatcca    120
gtatctgcca agagcatgtt gggtctcccg tgactgctgc ctcatcgata ccccatttag    180
ctccagaaag caaagaaaac tcgagtaaca cttgtttga                           219
```

<210> SEQ ID NO 98
<211> LENGTH: 171
<212> TYPE: DNA
<213> ORGANISM: Homo sapiens

<400> SEQUENCE: 98

```
tcatctccgt attcttcagc ttcatccaaa actgacttag aagcctccct tgaccctcac     60
ctgactattc acaggttata gcactttatg ttttcagtt ctgttatttt aattggtgcc    120
tctgtttgtg atctttaaga acataaaatt ctggcaagta actatttgct a             171
```

<210> SEQ ID NO 99
<211> LENGTH: 262
<212> TYPE: DNA
<213> ORGANISM: Homo sapiens

<400> SEQUENCE: 99

```
cactttgcag ccttgagagg tgcagaagag acaccgaggg gttcaccacc agagccacca     60
ttgtcagaga ggcgtccagc tgtgtccacc tgggactctg ccttcagggc ttcttgcctg   120
gctgggagct gcacaggcag actcctggga cggtgtgccg acagtctggg cacccccctt   180
ctaggatctg attcctgagg aatcacaatg tggatttcac aatcacttcc agtgtctttt   240
gccaacctct gtgaacagat gt                                             262
```

<210> SEQ ID NO 100
<211> LENGTH: 248
<212> TYPE: DNA
<213> ORGANISM: Homo sapiens

<400> SEQUENCE: 100

```
aagtttgcac agttctagac acgataaata catgtgaaat cacacaactc agaaaatgtc     60
ccttaaatta attgagccat tggtacttgt gaattagaag agacatctat gttctgatcc   120
actgttgaaa gctgtacaat gttacctatt tatttgcaga catcctttgg aaacaaatag   180
gtagatttgc aacaaataaa gagtggagta cagctgctga cattaccttg tatattcatg   240
cctttatg                                                             248
```

<210> SEQ ID NO 101
<211> LENGTH: 252
<212> TYPE: DNA
<213> ORGANISM: Homo sapiens
<220> FEATURE:
<221> NAME/KEY: misc_feature
<222> LOCATION: (123)..(124)
<223> OTHER INFORMATION: n is a, c, g, or t

<400> SEQUENCE: 101

```
gactgcacag cagcaagaca gattgccatg gagcatgttg tgcccaacta gggacagcgc     60
agatagattc tgtaatttgc ctaacaatgt ctataggatg atcccatttg tcaaaaaaaa   120
```

```
aanngaactg ggctttattg atgtcaccta aatgcaccta aacttctttt ttgccccatg      180
ctcttctgta ctcttgatct ttccccaaat ttttaaaaac atgacactca ttcccttatt      240
tttcctactt ag                                                          252

<210> SEQ ID NO 102
<211> LENGTH: 224
<212> TYPE: DNA
<213> ORGANISM: Homo sapiens

<400> SEQUENCE: 102
ttaattgctt tctctcacca gggaaggtgt gggaaggact tgtgaaatac atattcgagg       60
aaaaactatg cacaaggccg tgcatttaaa aataaactcc ctaaggctgg ggtgaaacct      120
gctacggtct gcgcaagttg actgttaatg aatttgattc tcaggtgtga gtgattaaaa      180
gaacactgat catgtcattt tcttttggt cactaattcc ctcc                         224

<210> SEQ ID NO 103
<211> LENGTH: 266
<212> TYPE: DNA
<213> ORGANISM: Homo sapiens

<400> SEQUENCE: 103
gtcatccaga gttataatgg cccattatct aatggtcaga gtttacttag gctttcacta       60
cttccactgc ccacttgaaa cagggaaaaa tattttcccc ccgcgctgtg agtgtgctat      120
ttagagctga ccacaagcgg ggggaagaga ggatggctcg gatgctgcat ttccactgag      180
aacacaaggc tggcaaagct tgtctgctgc ccagcaagca cttcaggctc acaccatttt      240
aggttcactt taagtagttt ctcaat                                            266

<210> SEQ ID NO 104
<211> LENGTH: 251
<212> TYPE: DNA
<213> ORGANISM: Homo sapiens

<400> SEQUENCE: 104
tggacagtgg acgtctgtca cccaagagag ttgtgggaga caagatcaca gctatgagca       60
cctcgcacgg tgtccaggat gcacagcaca atccatgatg cgttttctcc ccttacgcac      120
tttgaaaccc atgctagaaa agtgaataca tctgactgtg ctccactcca acctccagcc      180
tggatgtccc tgtctgggcc cttttttctgt tttttattct atgttcagca ccactggcac      240
caaatacatt t                                                            251

<210> SEQ ID NO 105
<211> LENGTH: 247
<212> TYPE: DNA
<213> ORGANISM: Homo sapiens
<220> FEATURE:
<221> NAME/KEY: misc_feature
<222> LOCATION: (55)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
```

<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (139)..(141)
<223> OTHER INFORMATION: n is a, c, g, or t

<400> SEQUENCE: 105
tccatggcaa cagtcccaac atgtttgaga cttcagctaa aggaatggat gtatnnnggn    60
gtgtagtctt cagtatatca ctgtatttcc gtaatactag actcnaagnt atgcnagatn   120
gnttattccc ttngtgaann nggagttgct cattacgttc ttgaaatatc gcacatcctg   180
ttggttcttc aaaggaagcc tttccaccag attagtgttc aagtctttgc agaggagacc   240
aactttt                                                            247

<210> SEQ ID NO 106
<211> LENGTH: 211
<212> TYPE: DNA
<213> ORGANISM: Homo sapiens

<400> SEQUENCE: 106
aaggctatgc tttcaatctc ctacacaaat tttacatctg gaatgatctg aaggttcttc    60
aaagacattc aaaattaggc ttttttatgt cctgttttaa gtgaaaatat ttattcttct   120
aagggtccat tttatttgta ttcattcttt tgtaaacctc tttacatttc tctttacatt   180
ttattctttg cccaaatcaa aagtgattcc t                                  211

<210> SEQ ID NO 107
<211> LENGTH: 187
<212> TYPE: DNA
<213> ORGANISM: Homo sapiens
<220> FEATURE:
<221> NAME/KEY: misc_feature
<222> LOCATION: (146)..(146)
<223> OTHER INFORMATION: n is a, c, g, or t

<400> SEQUENCE: 107
cttagcatta gaacactcag taatcatatg aattgtgcat tgtttgttt tgcttaactc     60 tttctgtttg tttatgtttg gggttttatt gttgttgttt cacttttctc ccatctcttc   120
ctgacttggt caaatccaaa ggaatnttcc aaattgtggg gagcaaggca tctgaaatgg   180
ctaaaac                                                            187

<210> SEQ ID NO 108
<211> LENGTH: 234
<212> TYPE: DNA
<213> ORGANISM: Homo sapiens
<220> FEATURE:
<221> NAME/KEY: misc_feature
<222> LOCATION: (120)..(120)
<223> OTHER INFORMATION: n is a, c, g, or t
<220> FEATURE:

```
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 108
atgctatatg ctgtatccca cctttctctg aatgttacat tttctcccct atcccaggct    60
gcatctaaga aaactcaaag ggaatatgct atctatcttt tccgagcaat gaaagctctn   120
gggttttttc cttgcttttc agggcacnat acttctcttt cttcctggtt agacaggata   180
agttctgagt cccntggtat catcagctta cttcttctct gttaaatatt caca         234

<210> SEQ ID NO 109
<211> LENGTH: 248
<212> TYPE: DNA
<213> ORGANISM: Homo sapiens

<400> SEQUENCE: 109
gtggtcttcc tctgaatatt agcagaagtt tcttattcaa aggcctcctc ccagaagaag    60
tcagtgggaa gagatggcca ggggaggaag tgggtttatt ttctgttgct attgatagtc   120
attgtattac tagaaatgaa ctgttgatga atagaatata ttcaggacaa tttggtcaat   180
tccaatgcaa gtacggaaac tgagttgtcc caaattgatg tgacagtcag gctgtttcat   240
cttttttg                                                            248

<210> SEQ ID NO 110
<211> LENGTH: 277
<212> TYPE: DNA
<213> ORGANISM: Homo sapiens

<400> SEQUENCE: 110
tatcctatta ctgtacttag ttggctatgc tggcatgtca ttatgggtaa aagtttgatg    60
gatttatttg tgagttattt ggttatgaaa atctagagat tgaagttttt cattagaaaa   120
taacacacat aacaagtcta tgatcatttt gcatttctgt aatcacagaa tagttctgca   180
atatttcatg tatattggaa ttgaagttca attgaatttt atctgtattt agtaaaaatt   240
aactttagct ttgatactaa tgaataaagc tgggttt                            277

<210> SEQ ID NO 111
<211> LENGTH: 245
<212> TYPE: DNA
<213> ORGANISM: Homo sapiens

<400> SEQUENCE: 111
gggattttga gctatcatct ctgcacatgc ttagtgagaa gactacacaa catttctaag    60
aatctgagat tttatattgt cagttaacca ctttcattat tcattcacct caggacatgc   120
agaaatattt cagtcagaac tgggaaacag aaggacctac attctgctgt cacttatgtg   180
tcaagaagca gatgatcgat gaggcaggtc agttgtaagt gagtcacatt gtagcattaa   240
attct                                                               245

<210> SEQ ID NO 112
<211> LENGTH: 284
<212> TYPE: DNA
<213> ORGANISM: Homo sapiens

<400> SEQUENCE: 112
```

```
ttgaatagat catcagtggc cactgatgta attaatcatg tctatgtaat gaagctgcca    60
taaaaaaccc aggaggacag tgttgagaga gcttctaggt tggtgaacac ttggggtgt    120 ctggaagaca gcccacctgg agaggacacg gaggctcttc gcaccttccc ccatacctgg   180
ctctctccat ctcttcattt gtccatctgt atctttttca ttatattatc cttgataata   240
aactggtaaa tataagtgtt tccctaagtt ctatgagcca ccat                    284
```

<210> SEQ ID NO 113
<211> LENGTH: 290
<212> TYPE: DNA
<213> ORGANISM: Homo sapiens

<400> SEQUENCE: 113

```
aggcctctga ttgcacttgt gtaggatgaa gctggtgggt gatgggaact cagcacctcc    60
cctcaggcag aaaagaatca tctgtggagc ttcaaaagaa ggggcctgga gtctctgcag   120
accaattcaa cccaaatctc gggggctctt tcatgattct aatgggcaac cagggttgaa   180
accttatttt ctagggtctt cagttgtaca agactgtggg tctgtaccag agcccccgtc   240
agagtagaat aaaaggctgg gtagggtaga gattcccatg tgcagtggag               290
```

<210> SEQ ID NO 114
<211> LENGTH: 270
<212> TYPE: DNA
<213> ORGANISM: Homo sapiens

<400> SEQUENCE: 114

```
atacgttttt cactttctga ccaggaccat gcctgtggag tagatgttga caagaaacac    60
tgaccagatc aaaatgtgtc tcaaggagaa tggcacaatt ttgtgcaaat gaatcaagga   120
agtcttattg cacaagagta tcctggaacc cagtgcaatt gattttttag aaaaatatat   180
cacatagggg aaaaaaactg gaatatgttg aaggagacgt atataatatt tagcatccag   240
attgatgact tctgccctaa ctatgcaatg                                     270
```

<210> SEQ ID NO 115
<211> LENGTH: 230
<212> TYPE: DNA
<213> ORGANISM: Homo sapiens

<400> SEQUENCE: 115

```
cgcttgaacc tggaaagtgg acattgcagt gagctgagat tgtgccactg cactccagcc    60
tgggcaacac agcgagactc tgtctcaaaa aaaaaaaaa aagaaagaaa aaaagagaa    120 aactcagaga ttcgtggaga ctggaaccac gggtgtggag agaggggtta gtagagacca   180
gattctgcag gtactataat gacattccca ggctaaggag tttagatctt               230
```

<210> SEQ ID NO 116
<211> LENGTH: 283
<212> TYPE: DNA
<213> ORGANISM: Homo sapiens

<400> SEQUENCE: 116

```
atctacaccc tcaggaataa gaaagtgaag ggggcagcga ggaggctgct gcggagtctg    60
gggagaggcc aggctgggca gtgagtagtt ggggagggga gaaagtatta agccagaacc   120
caaggatgga aataccccctt agtgagtcag tttagacttc aggctgttca ttttttgtatg  180 ataatctgca agatttgtcc taaggagtcc aatgggggat atgttttcct cccgtgagga   240
```
aatgtttagt tcttgaggga aaaatcccta aatcctctat ata        283

<210> SEQ ID NO 117
<211> LENGTH: 111
<212> TYPE: DNA
<213> ORGANISM: Homo sapiens

<400> SEQUENCE: 117
gggtagcaag ttcaccacag tgttaatggg ggtcccaagg tattcttccc ccaggcctag        60
gtatagggct attactcctc tctgctccag gtgtagacat acatttacat t        111

<210> SEQ ID NO 118
<211> LENGTH: 238
<212> TYPE: DNA
<213> ORGANISM: Homo sapiens

<400> SEQUENCE: 118
tggagggtga aattctgata gacttgaggc tttgagatgt ggtcctgggg tggagcaaga        60
caagaaaagt actggagatt ggggtttgag gagtctatgc aattattttt atttttaaaa        120
atctttgtgg ctacatagca ggtgtatata tttatgtggt aagtgagata tttcgataca        180
gacatacaat gtataatcac aggcatacaa tgtagacagg cataaagtgt atagtcac        238

<210> SEQ ID NO 119
<211> LENGTH: 299
<212> TYPE: DNA
<213> ORGANISM: Homo sapiens

<400> SEQUENCE: 119
aatgtgaaac tgctccatga accccaaaga attatgcaca tagatgcgat cattaagatg        60
cgaagccatc gagttaccac ctggcatgct taaactgtaa agagtgggtc aaagtaaact        120
gaattggaaa atccaaagtt atgcagaaaa acaataaagg atatagtaaa aagggttaac        180
gagccagtcc aggggaagcg aagaagacaa aaagagtcct tttctgggcc aagtttgata        240
aattaggcct cccgacccct tgctctgttg ctttatcaac tctactcggc aataacaat        299

<210> SEQ ID NO 120
<211> LENGTH: 294
<212> TYPE: DNA
<213> ORGANISM: Homo sapiens

<400> SEQUENCE: 120
gattaagaac agttttttca acaaatagtg ttgggacaat gggtgtccac atgcaaaaga        60
ataaagttgt ccccttacct tacaccatct ccaaaaatta actcaaaata tgtcaaagac        120
ataaacgtaa gagctaaaac tgtaaaactc ctagaataaa acataggagt aaatcttcat        180
gaccttggat taggccattg tgtcttaaat ataacaccaa aagaataagt aataaaaaaa        240
tagataaatt gaactccatc aaaattaaaa gcctttgtgc ttcataggac acca        294

<210> SEQ ID NO 121
<211> LENGTH: 269
<212> TYPE: DNA
<213> ORGANISM: Homo sapiens

<400> SEQUENCE: 121
tctcaagcta tgatcagaag actttaatta tatattttca tcctataagc ttaaatagga        60
aagtttcttc aacaggatta cagtgtagct acctacatgt tgaaaatatat agcctttaaa        120 tcattttttat attataactc tgtataatag agataagtcc attttttaaa aatgtttcc        180

```
ccaaaccata aaaccctata caagttgttc tagtaacaat acatgagaaa gatgtctatg    240
tagctgaaaa taaaatgacg tcacaagac                                      269
```

<210> SEQ ID NO 122
<211> LENGTH: 287
<212> TYPE: DNA
<213> ORGANISM: Homo sapiens

<400> SEQUENCE: 122

```
tctttcttt  ccagacaact ttgaatggag aggagcaaat tagtcttttg gtttaattct    60
gtctcagttt gcttatctaa agaaaggaaa acagagtggc tacacttgtt tagaaccata    120
tgcatactcc agagaaagat gctctattaa tccaaaaaaa tacagccact tgaaaccagc    180
caaagcgaaa gtgtaaggga cttcatggaa aggaggcagt tcaccaaagt attgaggggt    240
tttatatttt aaactccgcc agtgaattga cgtgttatgt cacttac                  287
```

<210> SEQ ID NO 123
<211> LENGTH: 275
<212> TYPE: DNA
<213> ORGANISM: Homo sapiens

<400> SEQUENCE: 123

```
gaatttattg gagcatgacc acggaggata gtatgagccc taaaaatcca gactctttcg    60
atacccagga ccaagccaca gcaggtcctc catcccaaca gccatgcccg cattagctct    120
tagacccaca gactggtttt gcaacgttta caccgactag ccaggaagta cttccacctc    180
gggcacattt tgggaagttg cattcctttg tcttcaaact gtgaagcatt tacagaaacg    240
catccagcaa gaatattgtc cctttgagca gaaat                               275
```

<210> SEQ ID NO 124
<211> LENGTH: 276
<212> TYPE: DNA
<213> ORGANISM: Homo sapiens

<400> SEQUENCE: 124

```
tccccggtta ctacctctta tccatccccg gccaccacct catacccatc ccctgtgccc    60
acctccttct cctctcccgg ctcctcgacc tacccatccc ctgtgcacag tggcttcccc    120
tccccgtcgg tggccaccac gtactcctct gttccccctg ctttcccggc ccaggtcagc    180
agcttccctt cctcagctgt caccaactcc ttcagcgcct ccacagggct ttcggacatg    240
acagcaacct tttctcccag gacaattgaa atttgc                              276
```

<210> SEQ ID NO 125
<211> LENGTH: 292
<212> TYPE: DNA
<213> ORGANISM: Homo sapiens

<400> SEQUENCE: 125

```
atgaagactt ggctgattca gatgccaggg ccttgtatga agcaggagaa aggagaaagg    60
ggacagacgt aaacgtgttc aataccatcc ttaccaccag aagctatcca caacttcgca    120
gagtgtttca gaaatacacc aagtacagta agcatgacat gaacaaagtt ctggacctgg    180
agttgaaagg tgacattgag aaatgcctca cagctatcgt gaagtgcgcc acaagcaaac    240 cagcttctt tgcagagaag cttcatcaag ccatgaaagt atgtaccatt ct             292
```

<210> SEQ ID NO 126

```
<211> LENGTH: 237
<212> TYPE: DNA
<213> ORGANISM: Homo sapiens

<400> SEQUENCE: 126
tgccttgtgt cttccgtttg acggaagaga atggattctg gtatctagac caaatcagaa      60
gggaacagta cattccaaat gaagaatttc ttcattctga tctcctagaa gacagcaaat     120
accgaaaaat ctactccttt actcttaagc ctcgaacaat tgaagatttt gagtctatga     180
atacatacct gcagacatct ccatcatctg tgtttactag taatcatttt gttcctt        237

<210> SEQ ID NO 127
<211> LENGTH: 285
<212> TYPE: DNA
<213> ORGANISM: Homo sapiens

<400> SEQUENCE: 127
ggtatagcat atgtggcctt gcttactaaa gtggatgatt gcagtgaggt tcttcaagac      60 aacttttttaa acatgagtag atctatgact tctcaaagcc gggtcatgaa tgtccataaa    120
atgctaggca ttcctatttc caatattttg atggttggaa attatgcttc agatttggaa    180
ctggacccca tgaaggatat tctcatcctc tctgcactga ggcagatgct gcgggctgca    240
gatgattttt tagaagattt gcctcttgag gaaactggtg cattt                   285

<210> SEQ ID NO 128
<211> LENGTH: 233
<212> TYPE: DNA
<213> ORGANISM: Homo sapiens

<400> SEQUENCE: 128
tgcttatccg ttagccgtgg tgatttagca ggaagctgtg agagcagttt ggtttctagc     60
atgaagacag agccccaccc tcagatgcac atgagctggc gggattgaaa gatgctgtct   120
tcgtactggg aaagggattt tcagcccctca gaatcgctcc accttgcagc tctcccctc    180 tctgtattcc tagaaactga cacatgctga acatcacagc ttatttcctc att           233

<210> SEQ ID NO 129
<211> LENGTH: 270
<212> TYPE: DNA
<213> ORGANISM: Homo sapiens

<400> SEQUENCE: 129
taggcaccac atgggatcct tgttcttcct ccttgtaagc agtaattgaa atcagtttgg     60
cagcctggtt tacagtgacc atggtggctt gtctcccgtg ctcttacctc actctgttga   120
tgttgtaaaa cctccagcta acttcatggg gtggctgacc cacgttgctc atttattcat   180
tcaacacata ttcattgacc atctactcta tgccaggtat tgttatcagc actgggaata   240
gatcagtgaa ctattgatct atttgtctaa                                    270

<210> SEQ ID NO 130
<211> LENGTH: 79
<212> TYPE: DNA
<213> ORGANISM: Homo sapiens

<400> SEQUENCE: 130
ctcagttctg gtccttcaag cctgtatggt ttggattttc agtaggggac agttgatgtg     60
gagtcaatct ctttggtac                                                 79
```

<210> SEQ ID NO 131
<211> LENGTH: 256
<212> TYPE: DNA
<213> ORGANISM: Homo sapiens

<400> SEQUENCE: 131

```
ctgaggtgct atgttcttag tggatgttct gaccctgctt caaatatttc cctcaccttt      60
cccatcttcc aagggtataa ggaatctttc tgctttgggg tttatcagaa ttctcagaat     120
ctcaaataac taaaaggtat gcaatcaaat ctgcttttta agaatgctc tttacttcat      180 ggacttccac tgccatcctc ccaaggggcc caaattcttt cagtggctac ctacatacaa     240
ttccaaacac atacag                                                    256
```

<210> SEQ ID NO 132
<211> LENGTH: 94
<212> TYPE: DNA
<213> ORGANISM: Homo sapiens

<400> SEQUENCE: 132

```
taacaaatca tcaacttcca ctggtcaata tatagatttt gggtgtctga ggccccaaga      60
ttagatgcca ctaatctcca aagattccct ccaa                                  94
```

<210> SEQ ID NO 133
<211> LENGTH: 254
<212> TYPE: DNA
<213> ORGANISM: Homo sapiens

<400> SEQUENCE: 133

```
gcagggtctt gggataacac tgtcatcaga acaaggctg ggggctgatt tcggggtggg       60
gagccttagg aggccagaaa ttccaatcag agccagtttt tctggagggg agtggctaga    120
cagtcaagga aggacgttca catttcaaaa gaagtcgggt gggggggatga gattattcta    180 gggggggcatc gaattccctt taaggggggg gctcacttct gcccagagta aagaggatct    240
cacaccatgg aaat                                                      254
```

<210> SEQ ID NO 134
<211> LENGTH: 298
<212> TYPE: DNA
<213> ORGANISM: Homo sapiens

<400> SEQUENCE: 134

```
tagttatact tacacactcc tctcatgttg tctatggagt ggtggatgct gcagggaggg      60
tgacatccta gttagtccta agagccagac tgcctgaagc tcactataac aagtcctgcc    120
ttggggaaga aggaagtgtg tctctgtgaa cctcccacct gggccgaaag ggaggccact    180
ctctctgctg cctctcccca accttggcct tctgtgctcc tagtgaacct ctcaccccct    240
gcctacagcc tcgaatctca gaccatgatg acctctggtc accctgaatc agagcttt      298
```

<210> SEQ ID NO 135
<211> LENGTH: 292
<212> TYPE: DNA
<213> ORGANISM: Homo sapiens

<400> SEQUENCE: 135

```
gtaaaattcc tatgtcagca ccctaatgag acaaatgaca tcctaattct tcccttggc      60 ttgccagttt gtaggtacta gttttcaga agttactcta aaatatttct gattgcagct     120
ccttcctaaa gagcagtatg agcagcatgt ggttatttat gtattcactc ttttctccta    180
```

```
cttctgtggt gacctggaac aaattctctt atgtatgtaa agattggaca gcccacctga    240
ttccgatgtc acttagatac actgttttg tatcagcctc ttctcttaga aa            292
```

```
<210> SEQ ID NO 136
<211> LENGTH: 180
<212> TYPE: DNA
<213> ORGANISM: Homo sapiens

<400> SEQUENCE: 136
gattgttggc caatagacct tccactccag tagagaggga ggacttggct ctgagaacct    60
ccatctgacc taagaggaaa cctcctctcc tatggccatc tcctcctcct gtcctttaag   120
tcctctgtgg ttactatatc tccttttccc tttcttaccc tttcgcttag caatttcaat   180
```

```
<210> SEQ ID NO 137
<211> LENGTH: 141
<212> TYPE: DNA
<213> ORGANISM: Homo sapiens

<400> SEQUENCE: 137
aagttctttg ggatagaggg tgaagaactt gggacatggg ctgtttcagg gcagctgaag    60
ttcaaagggg aataggtaat tgggggaag ggggaagtt gggcagaaa gggattgttg      120 ggccaatagg acctttccac t                                              141
```

```
<210> SEQ ID NO 138
<211> LENGTH: 248
<212> TYPE: DNA
<213> ORGANISM: Homo sapiens
<220> FEATURE:
<221> NAME/KEY: misc_feature
<222> LOCATION: (161)..(200)
<223> OTHER INFORMATION: n is a, c, g, or t

<400> SEQUENCE: 138
aggattatac ttcagtccct gctttacatt tatttcttaa agaagcttct ggtaaattag    60
agcaatagca tcggcttagt ttagtgttgt tctgttggac taaggatatc agttctatcc   120
gtatggtcgg gcctaaagcc tgggaaatat ttaatgaagg nnnnnnnnnn nnnnnnnnnn   180
nnnnnnnnnn nnnnnnnnnn ataacaaata acaaaacaaa aaccaagcca tttcccttta   240
tagtaaga                                                              248
```

```
<210> SEQ ID NO 139
<211> LENGTH: 259
<212> TYPE: DNA
<213> ORGANISM: Homo sapiens

<400> SEQUENCE: 139
acagaagcca ttgcctccct tgtttacctt gggtccacct ccaccaaaac ccaacagacc    60
accaaatgtt gacctgacga aattccacaa aacctcttct ggaaacagta ctagcaaagg   120
ccagacgtct tactcaacaa cttccctgcc accacctcca ccatcccatc cggccagcca   180
accaccattg ccagcatctc acccatcaca accaccagtc ccaagcctac ctcccagaaa   240
cattaaacct ccgtttgac                                                 259
```

```
<210> SEQ ID NO 140
<211> LENGTH: 199
<212> TYPE: DNA
<213> ORGANISM: Homo sapiens

<400> SEQUENCE: 140
```

```
gcacagctca gcacaacatt ccaagctcaa aatagaagcc ttctcagtga gctccagcac    60
gcccagagga ctgttaataa cgatgatcca tgtgttttac tctaaagtgc taaatatggg   120
agtttccttt ttttactct  ttgtcactga tgacacaaca gaaaagaaac tgtagacctt   180
gggacaatca acatttaaa                                                199

<210> SEQ ID NO 141
<211> LENGTH: 279
<212> TYPE: DNA
<213> ORGANISM: Homo sapiens

<400> SEQUENCE: 141
cctgccctgg aagtaatctt gctgtcctgg aatctcctcg gggatgaggc agctgccgag    60
ctggcccagg tgctgccgaa gatgggccgg ctgaagagag tggacctgga aagaatcag   120 atcacagctt tgggggcctg gctcctggct gaaggactgg cccaggggtc tagcatccaa   180
gtcatccgcc tctggaataa ccccattccc tgcgacatgg cccagcacct gaagagccag   240
gagcccaggc tggactttgc cttctttgac aaccagccc                          279

<210> SEQ ID NO 142
<211> LENGTH: 198
<212> TYPE: DNA
<213> ORGANISM: Homo sapiens

<400> SEQUENCE: 142
gcacagctca gcacaacatt ccaagctcaa aatagaagcc ttctcagtga gctccagcac    60
gcccagagga ctgttaataa cgatgatcca tgtgttttac tctaaagtgc taaatatggg   120
agtttccttt ttttactctt tgtcactgat gacacaacag aaaagaaact gtagaccttg   180
ggacaatcaa catttaaa                                                 198

<210> SEQ ID NO 143
<211> LENGTH: 183
<212> TYPE: DNA
<213> ORGANISM: Homo sapiens

<400> SEQUENCE: 143
gagagttcaa ctaagaaagg tcacatatgt gaaagcccaa ggacactgtt tgatatacag    60
caggtattca atcagtgtta tttgaaacca aatctgaatt tgaagtttga atcttctgag   120
ttggaatgaa ttttttttcta gctgagggaa actgtatttt tctttcccca agaggaatg   180 taa                                                                 183

<210> SEQ ID NO 144
<211> LENGTH: 294
<212> TYPE: DNA
<213> ORGANISM: Homo sapiens

<400> SEQUENCE: 144
ctcgattatt ccctgtacaa tatttaaaat ttattgcttg atacttttga caacaaatta    60
ggttttgtac aattgaactt aaataaatgt cattaaaata aataaatgca atatgtatta   120
atattcattg tataaaaata gaagaataca aacatatttg ttaaatatt  acatatgaaa   180 tttaatatag ctattttat ggaattttc attgatatga aaaatatgat attgcatatg   240
catagttccc atgttaaatc ccattcataa cttctcattaa agcatttact ttga         294

<210> SEQ ID NO 145
```

<211> LENGTH: 231
<212> TYPE: DNA
<213> ORGANISM: Homo sapiens

<400> SEQUENCE: 145

```
gcaaataaat tcatacatag tacatacaaa ataagagaaa aaattaaatt gcagatggtt      60
aaatatcaca tcacttaact gatgttactg aaaatgtatt ttcctgcata atcatatggt     120
tgacagtatg cattaagaag gtaagtaaaa caatgaagac aattttgatt taatatggta     180
atgcacaatt ccaactaacg tacattcaac agatcatgaa attgggttat t              231
```

<210> SEQ ID NO 146
<211> LENGTH: 175
<212> TYPE: DNA
<213> ORGANISM: Homo sapiens

<400> SEQUENCE: 146

```
ttgccttcta aatatactga aatgatttag atatgtgtca acaattaatg atctttatt      60
caatctaaga aatggtttag tttttctctt tagctctatg gcatttcact caagtggaca    120
ggggaaaaag taattgccat gggctccaaa gaatttgctt tatgttttta gctat          175
```

<210> SEQ ID NO 147
<211> LENGTH: 192
<212> TYPE: DNA
<213> ORGANISM: Homo sapiens

<400> SEQUENCE: 147

```
cctggccact cgcaagacct tttatctgaa aaccagccaa gctttattca cgacacactt      60
cttcccttca ctctcccact tctgtggtca actccctgca gaactcccaa actgccgttc    120
ttttcgatag ctcacgatgg tgtatgagtg tcaatcatct gacccttctt ggagtctcat    180
atttcgtgga ac                                                         192
```

<210> SEQ ID NO 148
<211> LENGTH: 187
<212> TYPE: DNA
<213> ORGANISM: Homo sapiens

<400> SEQUENCE: 148

```
ctgaggaccg gctgcagacc tcactctgag tggcaggcag agaaccaaag ctgcttcgct      60
gctctccagg gagaccctcc tgggatgggc ctgagaggcc ggggctcagg gaaggggctg    120
ggatcggaac ttcctgctct tgtttctgga caactttccc cttctgcttt aaaggttgtc    180
gattatt                                                               187
```

<210> SEQ ID NO 149
<211> LENGTH: 254
<212> TYPE: DNA
<213> ORGANISM: Homo sapiens

<400> SEQUENCE: 149

```
agtgtgatgg atccccttta ggttatttag gggtatatgt cccctgcttg aaccctgaag      60
gccaggtaat gagccatggc cattgtcccc agctgaggac caggtgtctc taaaaaccca    120
aacatcctgg agagtatgcg agaacctacc aagaaaaaca gtctcattac tcatatacag    180
caggcaaaga gacagaaaat taactgaaaa gcagtttaga gactggggga ggccggatct    240
ctagagccat cctg                                                       254
```

```
<210> SEQ ID NO 150
<211> LENGTH: 192
<212> TYPE: DNA
<213> ORGANISM: Homo sapiens

<400> SEQUENCE: 150
gcgttacaga tggacgtagc tgccttggtt ttccagtcct caagggaata ctgaagatgc      60
tgactgaagg ggattggatg ttgattttag aagatggaga actccagcca cctttgtaaa     120
gcactagtgt ttgtcattta tgtaagtcag gtcggctcag gtcttgatag tccgtcttgg     180
tgtgaggcat gc                                                         192

<210> SEQ ID NO 151
<211> LENGTH: 157
<212> TYPE: DNA
<213> ORGANISM: Homo sapiens

<400> SEQUENCE: 151
cacagtaatg tcgaaactag gcctttgaac caaggcagtc tagggtaaaa tatagtttca      60
aagtatgaat aagaattggt atttgtgtta tctttgagta agaaactgtc cgatatgaat     120
cacaacgtgg gtgaatgtag tattttcctg aagtgtg                              157

<210> SEQ ID NO 152
<211> LENGTH: 187
<212> TYPE: DNA
<213> ORGANISM: Homo sapiens

<400> SEQUENCE: 152
ggccatgaac atcacctgca caggacgggg accagacaac tgtatccagt gtgcccacta      60
cattgacggc ccccactgcg tcaagacctg cccggcagga gtcatgggag aaaacaacac     120
cctggtctgg aagtacgcag acgccggcca tgtgtgccac ctgtgccatc caaactgcac     180
ctacggg                                                               187

<210> SEQ ID NO 153
<211> LENGTH: 102
<212> TYPE: DNA
<213> ORGANISM: Homo sapiens

<400> SEQUENCE: 153
atcacaggtt tgagctgaat tatcacatga atataaatgg gaaatcagtg ttttagagag      60 agaactttc gacatatttc ctgttccctt ggaataaaaa ca                        102

<210> SEQ ID NO 154
<211> LENGTH: 203
<212> TYPE: DNA
<213> ORGANISM: Homo sapiens

<400> SEQUENCE: 154
agtttcagac aaatgttcag tgtgagtgag gaaaacatgt tcagtgagga aaaacattc      60 agacaaatgt tcagtgagga aaaaagggg aagttgggga taggcagatg ttgacttgag     120
gagttaatgt gatctttggg gagatacatc ttatagagtt agaaatagaa tctgaatttc     180
taaagggaga ttctggcttg gga                                             203

<210> SEQ ID NO 155
<211> LENGTH: 273
<212> TYPE: DNA
<213> ORGANISM: Homo sapiens
```

<400> SEQUENCE: 155

```
aacttaagct gaatgtgtaa tggatttgtc tatagtttta catatttgga agcattttaa      60
aataggtttt aatcttacat aaaattactt ttatacttgt gttaacattt tcttctgtgc     120
cttttgggta atttaatttc tgttatgaat ttctggtgcc tatgagctag ctatcaccta     180
cctgaaaggt gcttagaggt gaaggtactg tttctaaaaa cacatcactg tgacaccttt     240
ctatcctcac attttcaagc ttgcctcttt tct                                  273
```

<210> SEQ ID NO 156
<211> LENGTH: 135
<212> TYPE: DNA
<213> ORGANISM: Homo sapiens

<400> SEQUENCE: 156

```
gtgactgctt atgaagggtt attgctcagc taagtatttc tgaatgagtc ttaggtctgt      60
tggccttcaa tctctaccga aaccctgaga acttgatgat gcttttgttt tctgagaatc     120
gtttcagtgt gctgg                                                      135
```

<210> SEQ ID NO 157
<211> LENGTH: 218
<212> TYPE: DNA
<213> ORGANISM: Homo sapiens

<400> SEQUENCE: 157

```
catttgctgc aactctcagt ggtaagaatg attaagtgca gctataggag aatacttcca      60
ttggcatgcc acctgcgtaa acacacaat tttgttaaga tatacaataa aattattatg     120
ctaatagcaa atattttatg tagctcacta tgttccatgt agtcttctaa gtgcttcatg     180
ttagtcccca gttaaacacc tggttttgga aggctgag                             218
```

<210> SEQ ID NO 158
<211> LENGTH: 132
<212> TYPE: DNA
<213> ORGANISM: Homo sapiens

<400> SEQUENCE: 158

```
gtgagcctgc cagcgtttgc gacgtccccg cacgacaggc tcatactttc tgaggatcgt      60
gcatagcata ggacgtctga acctttgtac aaatgtgtag atgacatctt gctacagctt     120
ttatttgtga at                                                         132
```

<210> SEQ ID NO 159
<211> LENGTH: 129
<212> TYPE: DNA
<213> ORGANISM: Homo sapiens

<400> SEQUENCE: 159

```
gtaaattcaa tacaatgtca gttttttaaaa gtcaaagtta gatcaagaga atatttcaga      60
gttttggttt acacatcaag aaacagacac acatacctag gaaagattta cacaatagat     120
aatcatctt                                                             129
```

<210> SEQ ID NO 160
<211> LENGTH: 229
<212> TYPE: DNA
<213> ORGANISM: Homo sapiens

<400> SEQUENCE: 160

```
actgtacaaa gtataagtct tagatgtata tatttcctat attgttttca gtgtacatgg      60
```

```
aataacatgt aattaagtac tatgtatcaa tgagtaacag gaaaatttta aaaatacaga    120
tagatatatg ctctgcatgt tacataagat aaatgtgctg aatggttttc aaataaaaat    180
gaggtactct cctggaaata ttaagaaaga ctatctaaat gttgaaaga                229
```

<210> SEQ ID NO 161
<211> LENGTH: 181
<212> TYPE: DNA
<213> ORGANISM: Homo sapiens

<400> SEQUENCE: 161

```
gaggaccgag cacagaaatc ttagagattt cttgtcccct ctcaggtcat gtgtagatgc     60
gataaatcaa gtgattggtg tgcctgggtc tcactacaag cagcctatct gcttaagaga    120
ctctggagtt tcttatgtgc cctggtggac acttgcccac catcctgtga gtaaaagtga    180
a                                                                    181
```

<210> SEQ ID NO 162
<211> LENGTH: 280
<212> TYPE: DNA
<213> ORGANISM: Homo sapiens

<400> SEQUENCE: 162

```
tctgaactct caaaagtcta ttttttaac tgaaaatgta aatttataaa tatattcagg     60
agttggaatg ttgtagttac ctactgagta ggcggcgatt tttgtatgtt atgaacatgc    120
agttcattat tttgtggttc tatttactt tgtacttgtg tttgcttaaa caaagtgact    180
gtttggctta taaacacatt gaatgcgctt tattgcccat gggatatgtg gtgtatatcc    240
ttccaaaaaa ttaaaacgaa aataaagtag ctgcgattgg                          280
```

<210> SEQ ID NO 163
<211> LENGTH: 166
<212> TYPE: DNA
<213> ORGANISM: Homo sapiens

<400> SEQUENCE: 163

```
attcctgtca ttacccattg taacagagcc acaaactaat actatgcaat gttttaccaa     60
taatgcaata caaagaccct caaaatacct gtgcatttct tgtaggaaaa caacaaaagg    120
taattatgtg taattatact agaagttttg taatctgtat cttatc                   166
```

<210> SEQ ID NO 164
<211> LENGTH: 136
<212> TYPE: DNA
<213> ORGANISM: Homo sapiens

<400> SEQUENCE: 164

```
caggacccat cacgcctgtg cagtggcccc cacagaaaga ctgagctcaa ggtgggaacc     60
acgtctgcta acttggagcc ccagtgccaa gcacagtgcc tgcatgtatt tatccaataa    120
atgtgaaatt ctgtcc                                                    136
```

<210> SEQ ID NO 165
<211> LENGTH: 237
<212> TYPE: DNA
<213> ORGANISM: Homo sapiens

<400> SEQUENCE: 165

```
aaagtggcat tttcttgatt ggaaagggg aaggatctta ttgcacttgg gctgttcaga     60
```

```
atgtagaaag gacatatttg aggaagtatc tatttgagca ctgatttact ctgtaaaaag      120
caaaatctct ctgtcctaaa ctaatggaag cgattctccc atgctcatgt gtaatggttt      180
taacgttact cactggagag attggacttt ctggagttat ttaaccacta tgttcag         237

<210> SEQ ID NO 166
<211> LENGTH: 86
<212> TYPE: DNA
<213> ORGANISM: Homo sapiens

<400> SEQUENCE: 166
tttataatgt cccttcacaa acccagtgtt ttaggagcat gagtgccgtg tgtgtgcgtc       60
ctgtcggagc cctgtctcct ctctct                                           86

<210> SEQ ID NO 167
<211> LENGTH: 159
<212> TYPE: DNA
<213> ORGANISM: Homo sapiens

<400> SEQUENCE: 167
caccctcaga tgcacatgag ctggcgggat tgaaggatgc tgtcttcgta ctgggaaagg       60
gattttcagc cctcagaatc gctccacctt gcagctctcc ccttctctgt attcctagaa      120
actgacacat gctgaacatc acagcttatt tcctcattt                             159

<210> SEQ ID NO 168
<211> LENGTH: 175
<212> TYPE: DNA
<213> ORGANISM: Homo sapiens

<400> SEQUENCE: 168
aaatttaatt ttctacgcct ctggggatat ctgctcagcc aatggaaaat ctgggttcaa       60
ccagcccctg ccatttctta agactttctg ctgcactcac aggatcctga gctgcactta      120
cctgtgagag tcttcaaact tttaaacctt gccagtcagg acttttgcta ttgca           175

<210> SEQ ID NO 169
<211> LENGTH: 191
<212> TYPE: DNA
<213> ORGANISM: Homo sapiens

<400> SEQUENCE: 169
ctactcctta cagtctctag aattaaatgt actcatttag acaacatatt aaatgcatat       60
tttagccact ttagagaaac ctcataggca cagagtttcc aagattaatt ttaagaatat      120
cttcacgaac ttgaccctcc tactccacat tgcaacattt ccatcagaca gcatttcaat      180
tccagtatta t                                                           191

<210> SEQ ID NO 170
<211> LENGTH: 172
<212> TYPE: DNA
<213> ORGANISM: Homo sapiens

<400> SEQUENCE: 170
gtcatcatat ataattaaac agcttttaa agaaacataa ccacaaacct tttcaaataa        60
taataataat aataataaaa aatgtatttt aaagatggcc tgtggttatc ttggaaattg      120
gtgatttatg ctagaaagct tttaatgttg gtttattgtt gaattcctag aa              172

<210> SEQ ID NO 171
<211> LENGTH: 239
```

```
<212> TYPE: DNA
<213> ORGANISM: Homo sapiens

<400> SEQUENCE: 171
catggattag ctggaagatc tgtatttgat ggaagacctt gaaattattg gaagacatgg      60
atttcctgga agacgtggat tttcctggaa gatctggatt tggtggaaga ccagtaattg     120
ctggaagact ggatttgctg gaagacttga tttactggaa gacttggagc ttcttggaag     180
acatggattg tccggaagac atggattgtc tggaagatgt ggattttctg gaagctcag     239

<210> SEQ ID NO 172
<211> LENGTH: 255
<212> TYPE: DNA
<213> ORGANISM: Homo sapiens

<400> SEQUENCE: 172
gtggaggaaa ctaaacattc ccttgatggt ctcaagctat gatcagaaga ctttaattat      60
atattttcat cctataagct aaataggaa agtttcttca acaggattac agtgtagcta     120
cctacatgct gaaaaatata gcctttaaat cattttata ttataactct gtataataga     180
gataagtcca tttttaaaa atgttttccc caaaccataa accctatac aagttgttct     240 agtaacaata catga                                                      255

<210> SEQ ID NO 173
<211> LENGTH: 238
<212> TYPE: DNA
<213> ORGANISM: Homo sapiens

<400> SEQUENCE: 173
tcaataaggg cgttcttcct tgcaagttga acattattg tgctaggatt gctctctaga      60
caagccagaa gtgacttatt aaactattga aggaaaagga ctcaagaaaa ataataaaag     120
accataaata agggcgaaaa cattaccatg tgaaaagaat gtatttcacc tgcaagttac     180
aaaaaaatag tttgtgcatt gcaaataagc aaagacttgg attgacttta cattcatc      238

<210> SEQ ID NO 174
<211> LENGTH: 230
<212> TYPE: DNA
<213> ORGANISM: Homo sapiens

<400> SEQUENCE: 174
aagctgtgtt gttgcttctt gtgaaggcca tgatattttg ttttcccca attaattgct      60 attgtgttat tttactactt ctctctgtat tttttcttgc attgacatta tagacattga     120
ggacctcatc caaacaattt aaaaatgagt gtgaagggg aacaagtcaa atatttta     180 aaagatcttc aaaaataatg cctctgtcta gcatgccaac aagaatgcat                230

<210> SEQ ID NO 175
<211> LENGTH: 166
<212> TYPE: DNA
<213> ORGANISM: Homo sapiens

<400> SEQUENCE: 175
tgcctgttgt agaccacagt cacacactgc tgtagtcttc cccagtcctc attcccagct      60
gcctcttcct actgcttccg tctatcaaaa agccccttg gcccaggttc cctgagctgt     120
gggattctgc actggtgctt tggattccct gatatgttcc ttcaaa                    166

<210> SEQ ID NO 176
```

```
<211> LENGTH: 137
<212> TYPE: DNA
<213> ORGANISM: Homo sapiens

<400> SEQUENCE: 176
gtcagacaga tgtggttgca tcctaactcc atgtctctga gcattagatt tctcatttgc      60
caataataat acctccctta gaagtttgtt gtgaggatta ataatgtaa ataaagaact     120 agcataacac tcaaaaa                                                    137

<210> SEQ ID NO 177
<211> LENGTH: 227
<212> TYPE: DNA
<213> ORGANISM: Homo sapiens

<400> SEQUENCE: 177
tctgtgtgtg ccctgtaacc tgactggtta acagcagtcc tttgtaaaca gtgttttaaa      60
ctctcctagt caatatccac cccatccaat ttatcaagga gaaatggtt cagaaaatat     120 tttcagccta cagttatgtt cagtcacaca cacatacaaa atgttccttt tgcttttaaa     180 gtaattttg actcccagat cagtcagagc ccctacagca ttgttaa                    227

<210> SEQ ID NO 178
<211> LENGTH: 218
<212> TYPE: DNA
<213> ORGANISM: Homo sapiens

<400> SEQUENCE: 178
gtttaagcct ggaacttgta agaaaatgaa aatttaattt tttttctag gacgagctat      60 agaaaagcta ttgagagtat ctagttaatc agtgcagtag ttggaaacct tgctggtgta     120
tgtgatgtgc ttctgtgctt ttgaatgact ttatcatcta gtctttgtct attttttcctt    180 tgatgttcaa gtcctagtct ataggattgg cagtttaa                             218

<210> SEQ ID NO 179
<211> LENGTH: 243
<212> TYPE: DNA
<213> ORGANISM: Homo sapiens

<400> SEQUENCE: 179
gactgaggga tcgtagattt ttacaatctg tatctttgac aattctgggt gcgagtgtga      60
gagtgtgagc agggcttgct cctgccaacc acaattcaat gaatccccga ccccctacc     120 ccatgctgta cttgtggttc tctttttgta ttttgcatct gaccccgggg ggctgggaca     180
gattggcaat gggccgtccc ctctcccctt ggttctgcac tgttgccaat aaaaagctct     240
taa                                                                   243

<210> SEQ ID NO 180
<211> LENGTH: 267
<212> TYPE: DNA
<213> ORGANISM: Homo sapiens

<400> SEQUENCE: 180
ggagggaagg caagattctt tcccctccc tgctgaagca tgtggtacag aggcaagagc       60
agagcctgag aagcgtcagg tcccacttct gccatgcagc tactatgagc cctcggggcc    120
tcctcctggg cctcagcttg cccagataca tacctaaata tatatatata tatgtgaggg    180
agaacgcctc acccagattt tatcatgctg gaaagagtgt atgtatgtga agatgcttgg    240
tcaacttgta cccagtgaac acacaaa                                         267
```

<210> SEQ ID NO 181
<211> LENGTH: 267
<212> TYPE: DNA
<213> ORGANISM: Homo sapiens

<400> SEQUENCE: 181
ggagggaagg caagattctt tcccctccc tgctgaagca tgtggtacag aggcaagagc      60
agagcctgag aagcgtcagg tcccacttct gccatgcagc tactatgagc cctcggggcc     120
tcctcctggg cctcagcttg cccagataca tacctaaata tatatatata tatgtgaggg    180
agaacgcctc acccagattt tatcatgctg gaaagagtgt atgtatgtga agatgcttgg    240
tcaacttgta cccagtgaac acacaaa                                        267

<210> SEQ ID NO 182
<211> LENGTH: 206
<212> TYPE: DNA
<213> ORGANISM: Homo sapiens

<400> SEQUENCE: 182
tattcttcta taacactcta tatagagcta tgtgagtact aatcacattg aataatagtt     60
ataaaattat tgtatagaca tctgcttctt aaacagattg tgagttcttt gagaaacagc    120
gtggatttta cttatctgtg tattcacaga gcttagcaca gtgcctggta atgagcaagc    180
atacttgcca ttacttttcc ttccca                                         206

<210> SEQ ID NO 183
<211> LENGTH: 264
<212> TYPE: DNA
<213> ORGANISM: Homo sapiens

<400> SEQUENCE: 183
cctaatttga gggtcagttc ctgcagaagt gcccttttgcc tccactcaat gcctcaattt     60
gttttctgca tgactgagag tctcagtgtt ggaacgggac agtatttatg tatgagtttt    120
tcctatttat tttgagtctg tgaggtcttc ttgtcatgtg agtgtggttg tgaatgattt    180
cttttgaaga tatattgtag tagatgttac aattttgtcg ccaaactaaa cttgctgctt    240
aatgatttgc tcacatctag taaa                                           264

<210> SEQ ID NO 184
<211> LENGTH: 226
<212> TYPE: DNA
<213> ORGANISM: Homo sapiens

<400> SEQUENCE: 184
ggacactttt gaaaacagga ctcagcatcg ctttcaatag gcttttcagg accttcactg      60
cattaaaaca atatttttaa aaatttagta cagtttagaa agagcactta ttttgtttat    120
atccattttt tcttactaaa ttatagggat taactttgac aaatcatgct gctgttattt    180
tctacatttg tattttatcc atagcactta ttcacattta ggaaaa                   226

<210> SEQ ID NO 185
<211> LENGTH: 275
<212> TYPE: DNA
<213> ORGANISM: Homo sapiens

<400> SEQUENCE: 185
cagtttctgt tctctcacag gtgataaaca atgcttttttg tgcactacat actcttcagt     60

```
gtagagctct tgttttatgg gaaaaggctc aaatgccaaa ttgtgtttga tggattaata      120
tgcccttttg ccgatgcata ctattactga tgtgactcgg ttttgtcgca gctttgcttt      180
gtttaatgaa acacacttgt aaacctcttt tgcactttga aaaagaatcc agcgggatgc      240
tcgagcacct gtaaacaatt ttctcaacct atttg                                 275

<210> SEQ ID NO 186
<211> LENGTH: 275
<212> TYPE: DNA
<213> ORGANISM: Homo sapiens

<400> SEQUENCE: 186
cagtttctgt tctctcacag gtgataaaca atgcttttg tgcactacat actcttcagt       60
gtagagctct tgttttatgg gaaaaggctc aaatgccaaa ttgtgtttga tggattaata      120
tgcccttttg ccgatgcata ctattactga tgtgactcgg ttttgtcgca gctttgcttt      180
gtttaatgaa acacacttgt aaacctcttt tgcactttga aaaagaatcc agcgggatgc      240
tcgagcacct gtaaacaatt ttctcaacct atttg                                 275

<210> SEQ ID NO 187
<211> LENGTH: 114
<212> TYPE: DNA
<213> ORGANISM: Homo sapiens

<400> SEQUENCE: 187
agcaagtgta gacaccttcg agggcagaga tcgggagatt taagatgtta cagcatattt      60
ttttttcttg ttttacagta ttcaattttg tgttgattca gctaaattat gaaa            114

<210> SEQ ID NO 188
<211> LENGTH: 205
<212> TYPE: DNA
<213> ORGANISM: Homo sapiens

<400> SEQUENCE: 188
gtctcacata tttatataat cctcaaatat actgtaccat tttagatatt ttttaaacag      60
attaatttgg agaagtttta ttcattacct aattctgtgg caaaaatggt gcctctgatg      120
ttgtgatata gtattgtcag tgtgtacata tataaaacct gtgtaaacct ctgtccttat      180
gaaccataac aaatgtagct tttta                                            205

<210> SEQ ID NO 189
<211> LENGTH: 158
<212> TYPE: DNA
<213> ORGANISM: Homo sapiens

<400> SEQUENCE: 189
cagccccacc cctgtaaatg gaatttacca gatgaaggga atgaagtccc tcactgagcc      60
tcagatttcc tcacctgtga atgggctga ggcaggaaat gggaaaaagt gttagtgctt       120
ccaggcggca ctgacagcct cagtaacaat aaaaacaa                              158

<210> SEQ ID NO 190
<211> LENGTH: 254
<212> TYPE: DNA
<213> ORGANISM: Homo sapiens

<400> SEQUENCE: 190
tcagctgccc tgaaacagcc catgtcccaa gttcttcacc tctatccaaa gaacttgatt      60
tgcatggatt ttgataaaat catttcagta tcatctccat catatgcctg acccttgct       120
```

```
cccttcaatg ctagaaaatc gagttggcaa aatggggttt gggcccctca gagccctgcc      180
ctgcacccct gtacagtgtc tgtgccatgg atttcgtttt tcttggggta ctcttgatgt      240
gaagataatt tgca                                                        254
```

<210> SEQ ID NO 191
<211> LENGTH: 235
<212> TYPE: DNA
<213> ORGANISM: Homo sapiens

<400> SEQUENCE: 191

```
gagtgtctca gaagtgtgct cctctggcct cagttctcct cttttggaac aacataaaac      60
aaatttaatt ttctacgcct ctggggatat ctgctcagcc aatggaaaat ctgggttcaa      120
ccagcccctg ccatttctta agactttctg ctccactcac aggatcctga gctgcactta      180
cctgtgagag tcttcaaact tttaaacctt gccagtcagg acttttgcta ttgca           235
```

<210> SEQ ID NO 192
<211> LENGTH: 296
<212> TYPE: DNA
<213> ORGANISM: Homo sapiens

<400> SEQUENCE: 192

```
gagggacgtc agaaaatcag tgcattgtgg agtcactttt ctgataaagg gcacatcaga      60
ctgcaaatgg tccagacagc cagattcagg acactgatga gtttctgggg tcaccatagc      120
atccctggag tcagctgctc tgcagcctga aggagggctg acagtgtgga gtcactgcta      180
ttacttaatg aaattatata gaattctat atgattatg taattgcata atgaaaactc         240
tccatatcag agttcagaat atctcccaat ttccagtaca gaatattatc cataac           296
```

<210> SEQ ID NO 193
<211> LENGTH: 290
<212> TYPE: DNA
<213> ORGANISM: Homo sapiens

<400> SEQUENCE: 193

```
gacagcaata acttcgtttt agaaacattc aagcaatagc tttatagctt caacatatgg      60
tacgttttaa ccttgaaagt tttgcaatga tgaaagcagt atttgtacaa atgaaaagca      120
gaattctctt ttatatggtt tatactgttg atcagaaatg ttgattgtgc attgagtatt      180
aaaaaattag atgtatatta ttcattgttc tttactcatg agtaccttat aataataata      240
atgtattctt tgttaacaat gccatgttgg tactagttat taatcatatc                 290
```

<210> SEQ ID NO 194
<211> LENGTH: 269
<212> TYPE: DNA
<213> ORGANISM: Homo sapiens

<400> SEQUENCE: 194

```
ggcaggatat tgtaagcctt gaaaaagaat taggcaggat atcggaagcc ctgattagat      60
tctatcctaa gagcaacaga agatcactga cagtgtttta aatagataga ctagtttatt      120
agatttgcag tttagaagtt ccctttttt gtaattattg gacagtgtag agaccggatg       180
gtgagagatg agttaggaag ttgtgacagc tctctatacc taccgctaat gtagaggatt      240
atttattttc atttcattac cattcgtgt                                        269
```

<210> SEQ ID NO 195

```
<211> LENGTH: 215
<212> TYPE: DNA
<213> ORGANISM: Homo sapiens

<400> SEQUENCE: 195
gtaatatgtt tataatcctt tagatcttat aaatatgtgg tataaggaat gccatataat    60
gtgccaaaaa tctgagtgca tttaatttaa tgcttgctta tagtgctaaa gttaaatgat   120
cttaattctt tgcaattata tatgaaaaat gactgatttt tcttaaaata tgtaacttat   180
ataaatatat ctgtttgtac agattttaac cataa                              215

<210> SEQ ID NO 196
<211> LENGTH: 269
<212> TYPE: DNA
<213> ORGANISM: Homo sapiens

<400> SEQUENCE: 196
gtatccttga actggaaacc atccacgatc gagtatcgag tcattcaaca ctatcaattc    60
ctgggtgact ttttgaaaaa gtagtatctc ttgttgcaag aaatgctcca tctgtgagtc   120
catgtctctc actggaattg gatggaagtg gtgaatttca gccaaagtgg ccaaagaaat   180
cctgttcctg tgattctgac gtcatcagcc tctgcacctc tgtcttccct tctgccacat   240
gttgcctgtt ctccgtgact ttggtaaga                                     269

<210> SEQ ID NO 197
<211> LENGTH: 268
<212> TYPE: DNA
<213> ORGANISM: Homo sapiens

<400> SEQUENCE: 197
gagagagtga tcacgctgct gtgcccacct atgcggtaga ccttgttcct gggttgggag    60
atgttttatg atcagggtgc agtagaaaga gcacactagt agcagtaaag agaggtgacc   120
ctggctgcag ttctgcctct aacttcctga gtgacctcag gctagtcaca cagtgactgc   180
tccccacatt tctttttgta agctgcaagg attgaatcag acaatagcct ctaagtttct   240
tctgaactct catactcagg gatgccaa                                      268

<210> SEQ ID NO 198
<211> LENGTH: 258
<212> TYPE: DNA
<213> ORGANISM: Homo sapiens

<400> SEQUENCE: 198
ttccctccca ctaatttgtt ggcctttaac agcaattttg aaaactgggt cttctggtta    60 tgttttgtt ttaaaatctt taattagag gatgctgtgc cattgagtac tttaagttaa    120
tatgaggttc tggttcaagg aaaacttacg ttggatctga accaatgagc agatattttg   180
atatgtgcca ctcttgcata tacatctcag tcctaactaa aggttctagt ggcatccagg   240
acctttaggg aggcattt                                                 258

<210> SEQ ID NO 199
<211> LENGTH: 147
<212> TYPE: DNA
<213> ORGANISM: Homo sapiens

<400> SEQUENCE: 199
cactgcgtct ggcaataatg taactttgaa gcttaaaaat taatcccagt ttgtagcaat    60
aacagaagac tatctacaac ggaagaaaga agcaactgcc ttacagttct gtaaagaatt   120
```

```
<210> SEQ ID NO 200
<211> LENGTH: 274
<212> TYPE: DNA
<213> ORGANISM: Homo sapiens

<400> SEQUENCE: 200
cccttactta catactagct tccaaggaca ggtggaggta gggccagcct ggcgggagtg      60
gagaagccca gtctgtccta tgtaagggac aaagccaggt ctaatggtac tgggtagggg     120
gcactgccaa gacaataagc taggctactg ggtccagcta ctactttggt gggattcagg     180
tgagtctcca tgcacttcac atgttaccca gtgttcttgt tacttccaag gagaaccaag     240
aatggctctg tcacactcga agccaggttt gatc                                 274

<210> SEQ ID NO 201
<211> LENGTH: 155
<212> TYPE: DNA
<213> ORGANISM: Homo sapiens

<400> SEQUENCE: 201
cctcctttct aaatgcagcg acctgtgttc ttcagcccta tccctttcta ttcctctgac      60
cccgcctcct ttctaaatgc agcgacctct gttcttcagc cctatccctt tctattcctc     120 tgacccccgcc tcctttctaa atgcagcgac ctctg                               155

<210> SEQ ID NO 202
<211> LENGTH: 275
<212> TYPE: DNA
<213> ORGANISM: Homo sapiens

<400> SEQUENCE: 202
ggcgtcggcg cctagggcga agtgagccag ggtgcagtcg ggaagctcca ggacgaagcg      60
gcgcggcgga gccatggccc cagcgcagac cccgcgccgc ccgagcagcg gccccgacag     120
tggcccgcgc aggagccggc gggcgaaggc catgggcgcc tcagcgacgc cgccctcggc     180
cccgcctcgg aaacgaaacc tggcgggagc caggcgccgg cgggaaacga aacccggagg     240
gagccaggcg ccagcgggaa acgaaagcga agcgt                                275
```